US012381009B2

(12) United States Patent  
Soori-Arachi

(10) Patent No.: US 12,381,009 B2  
(45) Date of Patent: Aug. 5, 2025

(54) SYSTEMS AND METHODS FOR ARTIFICIAL INTELLIGENCE BASED STANDARD OF CARE SUPPORT

(71) Applicant: O/D Vision Inc., Sanibel, FL (US)

(72) Inventor: Marcus Charles Bernard Soori-Arachi, Fort Myers, FL (US)

(73) Assignee: O/D Vision INC., Sanibel, FL (US)

( * ) Notice: Subject to any disclaimer, the term of this patent is extended or adjusted under 35 U.S.C. 154(b) by 0 days.

(21) Appl. No.: 18/885,516

(22) Filed: Sep. 13, 2024

(65) Prior Publication Data

US 2025/0006376 A1 Jan. 2, 2025

Related U.S. Application Data

(60) Continuation-in-part of application No. 18/409,744, filed on Jan. 10, 2024, now abandoned, which is a
(Continued)

(51) Int. Cl.
*G06K 9/00* (2022.01)
*G16H 10/60* (2018.01)
(Continued)

(52) U.S. Cl.
CPC ............ *G16H 50/20* (2018.01); *G16H 10/60* (2018.01); *G16H 20/00* (2018.01); *G16H 80/00* (2018.01)

(58) Field of Classification Search
CPC ........ G16H 50/20; G16H 10/60; G16H 20/00; G16H 80/00; G06T 7/0012–0016;
(Continued)

(56) References Cited

U.S. PATENT DOCUMENTS

D326,521 S 5/1992 Sawada
5,360,010 A 11/1994 Applegate et al.
(Continued)

FOREIGN PATENT DOCUMENTS

CA 2827523 A1 8/2012
CA 3049901 A1 8/2012
(Continued)

OTHER PUBLICATIONS

Ashrafuzzaman, Md, et al. "Heart attack detection using smart phone." International journal of technology enhancements and emerging engineering research 1.3 (2013): 23-27.
(Continued)

*Primary Examiner* — Atiba O Fitzpatrick
(74) *Attorney, Agent, or Firm* — Outlier Patent Attorneys, PLLC

(57) ABSTRACT

An AI-based system and method for supporting differential diagnosis and standard of care in healthcare. The method involves receiving patient information from various sources, including patient-reported symptoms, physician notes, and sensor data from medical devices. The patient information is preprocessed and analyzed using deep learning models to generate a ranked list of potential diagnoses, each associated with likelihood scores and key contributing factors. The potential diagnoses are provided to physicians via an interactive interface, and physician feedback is collected to fine-tune the AI models using reinforcement learning. The method aims to enhance physician decision-making, improve diagnostic efficiency, and ensure adherence to the standard of care by leveraging AI's ability to analyze vast amounts of data more effectively than human physicians.

19 Claims, 29 Drawing Sheets

Related U.S. Application Data continuation-in-part of application No. 18/183,932, filed on Mar. 14, 2023, now Pat. No. 11,877,831, which is a division of application No. 29/830,662, filed on Mar. 14, 2022, now Pat. No. Des. 1,064,287.

(60) Provisional application No. 63/424,048, filed on Nov. 9, 2022, provisional application No. 63/319,738, filed on Mar. 14, 2022.

(51) Int. Cl.
   *G16H 20/00* (2018.01)
   *G16H 50/20* (2018.01)
   *G16H 80/00* (2018.01)

(58) Field of Classification Search
   CPC ............ G06T 2207/10064–10136; G06T 2207/30004–30104; G06T 2207/20081; G06T 2207/20084; G06T 9/002; G06T 5/60; G06V 2201/03–034; G06V 10/70; G06V 10/82; G06V 10/774–7796; G06V 10/454; G06K 9/6256; G06K 9/6257; G06K 9/6259; G06N 3/02–126; G06N 20/00–20; G06N 3/092; G06N 3/096; G06F 18/214–2155; G06F 7/023; G06F 40/16; G06F 18/2178; G01N 29/4481; G05B 2219/40499; G05B 2219/33056
   See application file for complete search history.

(56) References Cited

U.S. PATENT DOCUMENTS

| | | | |
|---|---|---|---|
| 5,724,348 A | 3/1998 | Basso et al. | |
| D430,812 S | 9/2000 | Levin et al. | |
| 6,411,839 B1 | 6/2002 | Okinishi | |
| 7,327,860 B2 | 2/2008 | Derakhshani et al. | |
| D595,415 S | 6/2009 | Fukuzawa | |
| 8,279,042 B2 | 10/2012 | Beenau et al. | |
| 8,353,842 B2 | 1/2013 | Al-Ali et al. | |
| D682,718 S | 5/2013 | Azuma | |
| 8,733,933 B2 | 5/2014 | Hirose et al. | |
| 8,768,014 B2 | 7/2014 | Du et al. | |
| 8,953,837 B2 | 2/2015 | Gilad-Gilor | |
| 9,015,008 B2 | 4/2015 | Geva et al. | |
| 9,351,650 B2 | 5/2016 | Uji et al. | |
| 9,443,343 B2 | 9/2016 | Rhee et al. | |
| 9,575,723 B2 | 2/2017 | Sofia et al. | |
| 9,636,023 B2 | 5/2017 | Geesbreght et al. | |
| 10,039,445 B1 | 8/2018 | Torch | |
| 10,074,148 B2 | 9/2018 | Cashman et al. | |
| D833,624 S | 11/2018 | DeJong et al. | |
| 10,117,568 B2 | 11/2018 | Reisman et al. | |
| 10,143,373 B2 | 12/2018 | Gilad-Gilor | |
| 10,149,614 B2 | 12/2018 | Privitera et al. | |
| 10,226,217 B2 | 3/2019 | Dubin et al. | |
| 10,314,485 B2 | 6/2019 | Kiderman et al. | |
| 10,346,601 B2 | 7/2019 | Yun et al. | |
| D874,007 S | 1/2020 | Chang et al. | |
| D908,894 S | 1/2021 | Eslava et al. | |
| 11,013,455 B2 | 5/2021 | Teicher et al. | |
| 11,013,467 B2 | 5/2021 | Dubin et al. | |
| 11,020,015 B2 | 6/2021 | Rege et al. | |
| D930,163 S | 9/2021 | Turkieltaub et al. | |
| 11,363,952 B2 | 6/2022 | Venkatraman et al. | |
| 11,452,446 B2 | 9/2022 | Karargyris et al. | |
| 11,478,142 B2 | 10/2022 | Jackson et al. | |
| D982,759 S | 4/2023 | Qian et al. | |
| 12,073,930 B1* | 8/2024 | Alperin | G16H 10/60 |
| 2005/0033185 A1 | 2/2005 | Danen | |
| 2006/0253002 A1 | 11/2006 | Kolanko et al. | |
| 2010/0104168 A1 | 4/2010 | Dobbe | |
| 2011/0119212 A1* | 5/2011 | De Bruin | A61B 5/369 |
| | | | 706/12 |
| 2012/0140170 A1 | 6/2012 | Hirose et al. | |
| 2012/0257164 A1 | 10/2012 | Zee et al. | |
| 2013/0023741 A1 | 1/2013 | Ayanruoh | |
| 2013/0070201 A1 | 3/2013 | Shahidi et al. | |
| 2013/0324810 A1 | 12/2013 | Gelland | |
| 2013/0331664 A1 | 12/2013 | Gilad-Gilor | |
| 2013/0338447 A1 | 12/2013 | Gilad-Gilor | |
| 2014/0018779 A1 | 1/2014 | Worrell et al. | |
| 2014/0044321 A1 | 2/2014 | Derakhshani et al. | |
| 2014/0073880 A1 | 3/2014 | Boucher et al. | |
| 2014/0358011 A1 | 12/2014 | Jiang et al. | |
| 2015/0199783 A1 | 7/2015 | Cashman et al. | |
| 2015/0324568 A1 | 11/2015 | Publicover et al. | |
| 2016/0012292 A1 | 1/2016 | Perna et al. | |
| 2016/0117544 A1 | 4/2016 | Hoyos et al. | |
| 2016/0220112 A1 | 8/2016 | Schmoll | |
| 2016/0335512 A1 | 11/2016 | Bradski | |
| 2017/0032092 A1 | 2/2017 | Mink et al. | |
| 2017/0112439 A1 | 4/2017 | Dubin et al. | |
| 2017/0235931 A1 | 8/2017 | Publicover et al. | |
| 2017/0238798 A1 | 8/2017 | Isogai et al. | |
| 2017/0329916 A1 | 11/2017 | Bychkov et al. | |
| 2018/0000336 A1 | 1/2018 | Gilad-Gilor et al. | |
| 2018/0113988 A1 | 4/2018 | Desgranges et al. | |
| 2018/0140180 A1 | 5/2018 | Coleman | |
| 2018/0144244 A1* | 5/2018 | Masoud | G06N 3/105 |
| 2018/0146911 A1 | 5/2018 | Teicher et al. | |
| 2018/0160887 A1 | 6/2018 | Hefez et al. | |
| 2018/0256087 A1 | 9/2018 | Al-Ali et al. | |
| 2018/0303343 A1 | 10/2018 | Dubin et al. | |
| 2018/0315193 A1 | 11/2018 | Paschalakis et al. | |
| 2019/0059728 A1 | 2/2019 | Gilad-Gilor | |
| 2019/0065722 A1 | 2/2019 | Kaehler | |
| 2019/0150762 A1 | 5/2019 | Chan et al. | |
| 2019/0189263 A1* | 6/2019 | Stoval, III | G16H 40/67 |
| 2019/0189266 A1* | 6/2019 | Stoval, III | G06N 3/08 |
| 2019/0189267 A1* | 6/2019 | Stoval, III | G06N 20/00 |
| 2019/0189268 A1* | 6/2019 | Stoval, III | G16H 50/70 |
| 2019/0279748 A1 | 9/2019 | Bychkov et al. | |
| 2019/0348178 A1* | 11/2019 | Eleftherou | G16H 50/50 |
| 2019/0387983 A1 | 12/2019 | Script | |
| 2020/0027210 A1* | 1/2020 | Haemel | G06F 9/547 |
| 2020/0029837 A1 | 1/2020 | Joudi | |
| 2020/0097080 A1 | 3/2020 | Kaehler | |
| 2020/0211692 A1* | 7/2020 | Kalafut | G16H 30/20 |
| 2020/0243200 A1* | 7/2020 | Ghouri | G06N 3/08 |
| 2020/0281534 A1 | 9/2020 | Geva et al. | |
| 2020/0305708 A1 | 10/2020 | Krueger | |
| 2020/0323427 A1 | 10/2020 | Gharib et al. | |
| 2020/0342245 A1 | 10/2020 | Lubin et al. | |
| 2020/0359971 A1 | 11/2020 | Zhao et al. | |
| 2020/0405148 A1 | 12/2020 | Tran | |
| 2021/0030275 A1 | 2/2021 | Gilad-Gilor | |
| 2021/0073845 A1 | 3/2021 | Kaehler | |
| 2021/0161378 A1 | 6/2021 | Mowrey et al. | |
| 2021/0183498 A1* | 6/2021 | Kalafut | G06T 7/0012 |
| 2021/0202094 A1 | 7/2021 | Bychkov et al. | |
| 2021/0236048 A1 | 8/2021 | Teicher et al. | |
| 2021/0236056 A1 | 8/2021 | Dubin et al. | |
| 2021/0393155 A1 | 12/2021 | Rogers et al. | |
| 2021/0393184 A1 | 12/2021 | Gallagher | |
| 2022/0005601 A1 | 1/2022 | Cox et al. | |
| 2022/0044454 A1* | 2/2022 | Gao | G06T 7/0012 |
| 2022/0059221 A1* | 2/2022 | Zhu | G16H 50/80 |
| 2022/0068154 A1 | 3/2022 | Breed et al. | |
| 2022/0160309 A1 | 5/2022 | Poltorak | |
| 2022/0160991 A1 | 5/2022 | Craig et al. | |
| 2022/0165418 A1 | 5/2022 | Li et al. | |
| 2022/0175325 A1 | 6/2022 | Fukushima et al. | |
| 2022/0198831 A1 | 6/2022 | Coleman et al. | |
| 2022/0254500 A1 | 8/2022 | El-Baz et al. | |
| 2022/0351377 A1 | 11/2022 | Ehlers et al. | |
| 2022/0400989 A1 | 12/2022 | Myers | |
| 2022/0405933 A1* | 12/2022 | Tajbakhsh | G06N 3/0895 |
| 2023/0013271 A1 | 1/2023 | Siminou et al. | |
| 2023/0029585 A1 | 2/2023 | Chono et al. | |
| 2023/0052691 A1* | 2/2023 | Thiruvenkatanathan | |
| | | | G06N 20/20 |
| 2023/0084637 A1 | 3/2023 | Matos | |

(56) References Cited

U.S. PATENT DOCUMENTS

| | | | |
|---|---|---|---|
| 2023/0162359 A1* | 5/2023 | Choi | G16H 50/20 |
| | | | 382/128 |
| 2023/0186686 A1 | 6/2023 | Hamid et al. | |
| 2023/0187056 A1 | 6/2023 | Atkinson et al. | |
| 2023/0215532 A1 | 7/2023 | Fung | |
| 2023/0230232 A1 | 7/2023 | Liu et al. | |
| 2023/0350996 A1 | 11/2023 | O'Connor et al. | |
| 2023/0352134 A1* | 11/2023 | Hasan | G16H 20/00 |
| 2024/0029901 A1* | 1/2024 | Ezhov | G16H 10/60 |
| 2024/0037990 A1 | 2/2024 | Chono et al. | |
| 2024/0164688 A1* | 5/2024 | Asirvatham | G06N 3/045 |
| 2024/0257967 A1* | 8/2024 | Sandler | G16H 15/00 |
| 2024/0296954 A1* | 9/2024 | Pagi | G16H 50/20 |
| 2024/0331136 A1* | 10/2024 | Valles Leon | G06V 10/70 |

FOREIGN PATENT DOCUMENTS

| | | | |
|---|---|---|---|
| CA | 2986363 A1 | 11/2016 | |
| CA | 2988683 A1 | 12/2016 | |
| CA | 3041237 A1 | 4/2017 | |
| CA | 3023829 A1 | 11/2017 | |
| CN | 300699451 A | 10/2007 | |
| CN | 101460097 A | 6/2009 | |
| CN | 101411607 B | 5/2010 | |
| CN | 109124686 A | 1/2019 | |
| CN | 307246637 A | 4/2022 | |
| EP | 3297517 B1 | 3/2018 | |
| EP | 3307142 B1 | 4/2018 | |
| EP | 2675345 B1 | 3/2019 | |
| EP | 3813074 A1 | 4/2021 | |
| EP | 2675351 B1 | 6/2021 | |
| EP | 3834713 A1 | 6/2021 | |
| EP | 3838111 A1 | 6/2021 | |
| IN | 202111060104 A | 12/2021 | |
| IN | 202141057189 A | 2/2022 | |
| IN | 202241006220 A | 11/2022 | |
| WO | 2010131550 A1 | 11/2010 | |
| WO | 2011016029 A2 | 2/2011 | |
| WO | 2011066546 A1 | 6/2011 | |
| WO | 2012111012 A1 | 8/2012 | |
| WO | 2012111013 A1 | 8/2012 | |
| WO | 2013163443 A2 | 10/2013 | |
| WO | 2016108229 A1 | 7/2016 | |
| WO | 2016157173 A1 | 10/2016 | |
| WO | 2016159523 A1 | 10/2016 | |
| WO | 2016185463 A1 | 11/2016 | |
| WO | 2016199134 A1 | 12/2016 | |
| WO | 2017068573 A1 | 4/2017 | |
| WO | 2017195203 A2 | 11/2017 | |
| WO | 2019103912 A2 | 5/2019 | |
| WO | 2020161709 A1 | 8/2020 | |
| WO | 2020161710 A1 | 8/2020 | |
| WO | 2020198154 A1 | 10/2020 | |
| WO | 2021140503 A1 | 7/2021 | |
| WO | 2021144790 A1 | 7/2021 | |
| WO | 2022153320 A1 | 7/2022 | |
| WO | 2023150229 A1 | 8/2023 | |

OTHER PUBLICATIONS

Brennan, Paul F., et al. "Assessment of the conjunctival microcirculation for patients presenting with acute myocardial infarction compared to healthy controls." Scientific Reports 11.1 (2021): 7660.

Brennan, Paul F., et al. "Assessment of the conjunctival microcirculation in adult patients with cyanotic congenital heart disease compared to healthy controls." Microvascular Research 136 (2021): 104167.

Jo, Hang-Chan, et al. "Quantification of blood flow velocity in the human conjunctival microvessels using deep learning-based stabilization algorithm." Sensors 21.9 (2021): 3224.

Karanam, Veena C., et al. "Functional slit lamp biomicroscopy metrics correlate with cardiovascular risk." The ocular surface 17.1 (2019): 64-69.

Landi, Heather, "AI startup that captures vital signs via phone cameras launches new corporate wellness solution," Jan. 11, 2021, Retrieved from the Internet: https://www.fiercehealthcare.com/tech/ai-health-startup-captures-vital-signs-via-phone-cameras-launches-new-corporate-wellness, pp. 1-2.

Marcus C.B. Soori, Tricoder.Zero Linked In Post, Published on: Jul. 2023, LinkedIn.com, Retrieved from Internet: https://www.linkedin.com/posts/marcussoori_ tricorderzero-tricorder -health-activity-706357805437 517 4144-Ssi i?trk=public_profile_share_view (Year: 2023).

Mayrovitz, Harvey N., Donald Larnard, and Gloria Duda. "Blood velocity measurement in human conjunctival vessels." Cardiovascular diseases 8.4 (1981): 509.

Nicole Sorkin, Tricorder.Zero Set to Revolutionize Telehealth & Telefitness, Published on: Mar. 25, 2023, Medium.com Retrieved from Internet: https://medium.com/@nicolesorkin/tricorder-zero-326a69a87f0 (Year: 2023.

PCT International Search Report and Written Opinion dated Jun. 28, 2023, PCT International Application No. PCT/US23/64353.

Phelan, Ryan, "How the Courts treat Artificial Intelligence (AI) Patent Inventions: Through the Years since Alice," Mar. 12, 2021, Retrieved from the Internet: https://www.patentnext.com/2021/03/how-the-courts-treat-artificial-intelligence-ai-patent-inventions-through-the-years-since-alice/?utm_source=Mondaq&utm_medium=syndication&utm_campaign=LinkedIn-integration#, pp. 1-16.

Shieh-Newton, Terri, et al., "Patenting Considerations for Artificial Intelligence in Biotech and Synthetic Biology—Part 2: Key Issues in Patent Subject Matter Eligibility," Jan. 30, 2020, Retrieved from the Internet: https://www.mintz.com/insights-center/viewpoints/2231/2020-01-30-patenting-considerations-artificial-intelligence-biotech, pp. 1-5.

* cited by examiner

SYSTEMS AND METHODS FOR ARTIFICIAL INTELLIGENCE BASED STANDARD OF CARE SUPPORT

CROSS-REFERENCE TO RELATED APPLICATIONS

This application is a continuation-in-part of U.S. patent application Ser. No. 18/409,744, filed Jan. 10, 2024, titled "SYSTEMS AND METHODS FOR BIOMETRIC IDENTIFICATION USING PATTERNS AND BLOOD FLOW CHARACTERISTICS OF THE OUTER EYE", which is a continuation-in-part of U.S. patent application Ser. No. 18/183,932, filed Mar. 14, 2023, titled "SYSTEMS AND METHODS FOR ARTIFICIAL INTELLIGENCE BASED BLOOD PRESSURE COMPUTATION BASED ON IMAGES OF THE OUTER EYE", which claims the benefit of: U.S. Provisional Application 63/319,738, filed Mar. 14, 2022, titled "SYSTEMS AND METHODS FOR REMOTE AND AUTOMATED MEDICAL DIAGNOSIS," which is herein incorporated by reference in its entirety, U.S. Design application Ser. No. 29/830,662, filed Mar. 14, 2022, titled "CONSUMER ELECTRONICS DEVICE," which is herein incorporated by reference in its entirety, and U.S. Provisional Application 63/424,048, filed Nov. 9, 2022, titled "SYSTEMS AND METHODS FOR REMOTE AND AUTOMATED MEDICAL DIAGNOSIS," which is herein incorporated by reference in its entirety.

BACKGROUND

Field of Art

This invention pertains to the field of medical devices, with a specific focus on a hand-held multi-functional medical diagnostic device that integrates various health monitoring sensors in a compact and user-friendly form.

Discussion of the State of the Art

Biometric identification technologies generally rely on the principle that each individual has distinguishing characteristic(s) unique to that particular individual. In many cases this involves some sort of identifiable pattern (e.g. fingerprints, iris patterns, etc.) associated with a physical or biological characteristic of the individual. A problem with these patterns is that they can be artificially generated in order to fool biometric identification systems. For example, through advances in 3D printing technology, these patterns can be reproduced in 3D with the precision necessary to fool biometric scanners (e.g. via 3D models, contact lenses, etc.).

Currently available medical diagnostic devices are large, bulky devices with poor portability and usability. For example, devices like MRI machines, CT scanners, and research grade ECG/EEG equipment lack portability outside hospitals and dedicated facilities. Significant expertise is also required to operate them and interpret their results, limiting accessibility for general healthcare use.

Some have tried to condense the form factor of medical diagnostic devices, but these devices are severely limited with regards to their accuracy, reliability, and functionality. Additionally, these portable devices focus on a single diagnostic function because it is challenging to maintain the accuracy and reliability of each sensor while ensuring the device remains portable and easy to use. For example, it is challenging to minimize interference between sensor components, leading to inaccurate or skewed readings. Additionally, managing power efficiently to extend battery life is very difficult, particularly in a device that incorporates several sensors and functions. Broadly, the computation, connectivity, and sensor components required strain typical battery capacities, severely limiting run time between charges. This not only inconveniences end-users but also leads to gaps in health measurement data. Additionally, the complexity of synchronizing data from multiple sensors, running analysis algorithms, and providing user-friendly interfaces has often exceeded the processing capabilities that can be integrated given size and power constraints. Insufficient processing resources can lead to latency and errors in displaying important diagnostic results to end-users when they need it.

As a result, individuals seeking a comprehensive health assessment are required to use large and expensive machines, which provide high accuracy, but at the expense of inconvenience and cost, or portable devices with poor accuracy and reliability, and the use of multiple devices, which can be cumbersome and costly.

Additionally, many such medical devices lack the ability to provide real-time, personalized insights and recommendations to patients and healthcare providers. This may be possible by using AI systems, however, the computational requirements of AI algorithms often exceed the processing power and storage capacity available on small, portable devices. This limitation has posed a significant challenge in the development of AI-enabled medical devices.

Traditionally, developers have attempted to address this issue by relying on either on-device processing or cloud computing. On-device processing involves running simple, lightweight algorithms directly on the medical device itself. While this approach provides fast response times and can operate independently of network connectivity, it severely limits the complexity and sophistication of the AI algorithms that can be employed. On the other hand, cloud computing offloads all AI processing to remote servers, which can handle more advanced algorithms but introduces issues related to latency, network dependence, and data privacy concerns.

These conventional approaches to integrating AI into medical devices have proven suboptimal due to their inherent trade-offs and limitations. On-device processing sacrifices AI performance for local computation, while cloud computing introduces delays and relies on constant network availability. Moreover, both approaches raise concerns regarding the security and privacy of sensitive medical data, as it must be either stored on the device or transmitted to remote servers.

Another problem addressed by the present invention relates to the field of targeted advertising and personalized interaction in public or semi-public spaces using recognition systems. Current technologies in this field include various methods of identifying and analyzing individuals as they move through such spaces to deliver personalized content, including advertisements and interactive experiences. These technologies typically utilize cameras and sensors combined with AI-driven software to detect and recognize individuals based on facial features, movements, and sometimes even biometric data.

Previous attempts to solve the problem of delivering personalized content effectively have included the use of facial recognition technologies, voice recognition systems, and motion sensors that track the movements of individuals. These systems collect data and analyze it to tailor advertisements or informational content displayed on digital signage or broadcasted through audio systems. However, these solutions have several limitations.

These existing technologies often struggle with accuracy in diverse environmental conditions. For instance, poor lighting or crowded spaces can significantly decrease the reliability of facial recognition systems. Additionally, these systems generally require a direct line of sight to the individual, limiting their effectiveness in dynamic environments where obstructions are common.

Additionally, the adaptability of current systems is often lacking. Many are not equipped to learn or evolve based on interaction outcomes or environmental changes. This results in a static system that does not improve over time or adjust to new types of data or changes in user behavior, thereby diminishing the potential for truly personalized interactions.

While there are existing methods and technologies aimed at identifying individuals and delivering personalized content in public spaces, these methods are often hindered by issues of accuracy, privacy concerns, and lack of adaptability.

Diagnosing medical conditions and determining appropriate treatments can be a complex and time-consuming process for providers. Doctors must consider a wide range of information, including patient-reported symptoms, physical examination findings, sensor data and test results, as well as the provider's own knowledge and experience. Based on this information, the doctor must narrow down the list of potential diagnoses and decide on next steps, which may include ordering additional tests, prescribing treatments and/or medications, or referring the patient to a specialist.

Failing to consider all relevant information or appropriately weigh different factors can lead to misdiagnosis or suboptimal care. Even experienced providers may occasionally overlook a potential diagnosis or order unnecessary tests. Such mistakes can negatively impact patient outcomes, increase healthcare costs, and potentially expose doctors to malpractice liability if the standard of care was not followed.

Some tools exist to help doctors with the diagnostic process, such as reference books, online symptom checkers, and clinical decision support software. However, these tools have significant limitations. Reference materials contain a huge volume of information that a human cannot memorize or quickly sort through. Symptom checkers used by patients are very general and do not consider the full scope of information available to the provider. Existing clinical decision support systems are often rule-based, do not learn or improve over time, and/or are limited in the types and quantity of data used to generate the rule.

Therefore, there is a need for improved systems and methods to assist providers with medical diagnosis in a way that considers all available patient information, compares it to an extensive knowledge base, provides data-driven recommendations, and becomes more accurate and capable over time. The development of such a system faces technical challenges in processing multi-modal data, representing medical knowledge in a structured way, analyzing information in real-time during a patient encounter, and enabling the system to learn from feedback and additional data. Overcoming these challenges could significantly enhance the efficiency and accuracy of diagnosis.

Current health and fitness tracking devices, whether wearable or non-wearable, typically collect and display various sensor readings to the user. However, these devices face significant technical limitations in their ability to meaningfully interpret the data for the user. The devices lack the necessary algorithms and computational power to analyze the complex, multi-factorial sensor data in real-time to accurately identify potential health concerns.

Existing devices are often restricted to comparing each individual sensor reading to a predefined, generic range. However, these ranges fail to account for the numerous personal factors that impact a user's health such as age, race, height, pre-existing conditions, diet, exercise habits, and medications. The devices lack the technical capability to integrate and analyze these multiple data streams to generate personalized, dynamic ranges tailored to each specific user.

Moreover, current tracking devices operate in isolation, only analyzing the data collected by their own sensors. They are not configured to send and receive data from other sources such as the user's medical records, past lab results, or symptom logs. This siloed approach prevents the development of a comprehensive picture of the user's health required for accurate identification of potential concerns. The devices lack the interoperability and security features needed to gather sensitive medical data from disparate sources.

Even if existing devices could collect and integrate the necessary data streams, they do not possess the machine learning capabilities to identify complex patterns and relationships indicative of health issues. Conventional rule-based algorithms are insufficient to handle the intricacies and variability of human health across diverse populations. The devices lack the adaptive AI technologies required to refine their analysis over time based on cumulative user data.

Assuming the technical challenges of data integration and analysis could be overcome, current devices would still face difficulties in communicating results to the user. Providing a binary "healthy" or "unhealthy" determination based on sensor data risks crossing the line into impermissible diagnosis. The devices lack the technical means to present a non-diagnostic yet actionable assessment to the user, such as a graded warning system, to empower informed decision-making.

Therefore, there is a need for a technically sophisticated system to collect and synthesize sensor data, medical records, and user-inputted information in real-time. The system requires advanced machine learning algorithms to identify user-specific patterns and generate personalized health assessments. Critically, the system must possess the technical capacity to present meaningful feedback to the user in a format that encourages appropriate action without offering a diagnosis. Overcoming these challenges requires an integrated, adaptive platform beyond the scope of current health tracking devices.

In the digital landscape, there is an increasing interest in the creation and expansion of virtual environments, specifically within the concept known as the metaverse. The metaverse is anticipated to offer an expansive, interconnected digital space, where individuals can interact, perform tasks, work, and even receive healthcare services through avatars. However, the transition from real-world activities into their digital counterparts poses several challenges, particularly in the realm of personal tasks such as healthcare appointments, within the metaverse.

One of the primary issues is the ability to receive healthcare services in a virtual environment without sacrificing the privacy and security of sensitive personal information. Traditional telehealth services often require the disclosure of private information, which can be susceptible to theft or misuse. These services do not always capitalize on the potential for anonymity, an aspect that can alleviate the discomfort some individuals feel when seeking certain types of healthcare.

Additionally, the seamless integration of real-world tasks, such as healthcare appointments, into the virtual environment confronts obstacles. While participants in the metaverse may desire the convenience of completing these tasks without departing from the virtual space, solutions that encompass the complex interplay between virtual activities and physical consequences are limited. This challenge accentuates the need for innovative approaches to embed real-world functionalities within the metaverse, all while maintaining a user-friendly and secure interface.

Another problem is the lack of sufficient security measures within virtual spaces, particularly concerning healthcare services. The current telehealth models do not fully exploit technologies like blockchain, which can offer enhanced security through data encryption and secure tokens. This inadequacy opens avenues for potential data breaches and identity theft, underscoring the necessity for improved security mechanisms in the crossover between healthcare and virtual environments.

Additionally, existing telehealth approaches in the real world suffer from inefficiencies due to a lack of multisensor based devices operable to provide sensor data transmitted from the patient to a provider to facilitate healthcare consultations. The same problem arises in virtual environments such as the metaverse which currently lack the ability for a patient to provide real-time sensor data from a compatible multisensor device.

Attempts to address these concerns within the nascent framework of the metaverse have been scarce, primarily due to its embryonic state and the technological limitations of current virtual reality systems. Existing virtual environments, such as those accessible through devices like the Oculus Quest, offer only rudimentary capabilities, limiting interactions to basic social and gaming activities without the complexity or scale envisioned for the metaverse. As such, the foundational technologies and approaches to facilitate comprehensive healthcare services, secure data exchange, and the integration of real-world tasks in these emerging digital universes remain underdeveloped.

The lack of precedent and existing solutions further complicates efforts to bridge the gap between the traditional execution of tasks and their virtual analogs. While virtual reality technologies have laid the groundwork for simulated environments, they fall short of creating a fully immersive, secure, and integrated metaverse experience that encompasses complex interactions, such as healthcare, in a seamless and privacy-preserving manner. These shortcomings highlight the gap in current digital capabilities and underscore the necessity for innovative solutions tailored to the unique emerging demands of life within the metaverse.

SUMMARY

The present invention relates, in part, to biometric identification using a combination of static biological or physiological characteristics and active or dynamic biological or physiological characteristics of an individual. In particular, an identity of an individual is determined using a combination of a pattern characteristic unique to an individual and a measure of a dynamically changing blood flow characteristic. For example, the microvasculature of the outer eye (e.g. in the scleral region) presents a unique pattern for each individual which can be detected as described herein and combined with blood velocity characteristics through at least a portion of the same microvasculature of the outer eye. This combination of measures allows for identification of an individual without being able to be faked by current technology. That is, while patterns alone are becoming increasingly reproducible by artificial means, the actual blood flow characteristics of a living individual cannot be faked.

One novel approach to biometric identification described herein includes obtaining a first image, from a first camera, of the vasculature of the outer eye of an individual, obtaining a series of second images at a higher magnification than the first image, from a second camera, of the vasculature of the outer eye of the individual, applying a first AI algorithm to analyze the images from the first camera to determine at least one pattern characteristic associated with the eye vasculature, applying a second AI algorithm to analyze the images from the second camera to determine at least one blood flow characteristic (e.g. velocity) within the eye vasculature, and applying a third AI algorithm to determine an identity of the individual based on the combination of the analysis of the at least one pattern characteristic and the at least one blood flow characteristic. In one aspect, the third AI algorithm is operable to compare the at least one pattern characteristic and the at least one blood flow characteristic with a database of previously established pattern characteristics and blood flow characteristics for a plurality of individuals in order to determine identity.

Currently, there are no known conventional approaches to biometric identification techniques or systems which rely on the combination of eye vasculature patterns and dynamic blood flow characteristics. The present approaches allow for contactless, real-time biometric identification from computer vision and AI processing of images of the outer eye which is not known to exist in the prior art.

The present invention is for a hand-held medical diagnostic device that integrates multiple health monitoring sensors in a compact and user-friendly design. This approach overcomes the limitations of both large, stationary medical equipment as well as less reliable, single-function portable devices.

The handheld medical diagnostic device incorporates novel techniques and components for balanced integration. Multiple physiological sensors are combined to measure a wide range of health parameters, while proprietary calibration methods and sensor shielding maintain accuracy of and isolate potential interference between components. Complex yet efficient analysis algorithms are implemented in application-specific integrated circuits tailored for low-power parallel processing. These specially designed circuits synchronize output from the sensors, run diagnostics tests, and translate raw data into easy-to-understand health insights for the user. Power management is optimized between custom battery components and power-efficient hardware to enable extended operation times from a single charge. Additionally, an intuitive user interface with the ability to display instructions and diagnostic data that has been processed, for example, on board or in a connected cloud server. The total aggregation of custom engineered sensors, hardware, software, and power components enables comprehensive and accurate diagnostic capabilities within a compact, reliable, and accessible device.

Broadly, in accordance with an embodiment of the invention, the inventive device is composed of multiple sensor modalities into a single compact housing with the housing shaped to comfortably position the sensors against a user during operation. The sensor functions include, but are not limited to, otoscopy, high magnification skin and outer eye imaging, infrared thermometry, pulse oximetry, auscultation, electrocardiography, and body composition analysis. The measured results display on an integrated screen to provide diagnostic data and/or analytics in a single device.

An aspect of the inventive design is minimizing interference between these sensors. This is achieved through careful circuit design and the use of shielding techniques, which help maintain the accuracy and reliability of readings.

To address power management challenges, the device is equipped with a high-capacity battery and an intelligent power distribution system. This system dynamically allocates power to different sensors based on their current usage, optimizing overall battery life and maintaining consistent sensor performance.

The inventive device also incorporates an energy-efficient microprocessor, capable of handling the demands of processing data from multiple sensors. This processor, alongside optimized software algorithms, allows for swift and accurate data processing, reducing latency and potential errors in displaying diagnostic results.

The device also features a straightforward, high-resolution display interface, designed for case of use. This interface simplifies navigation and understanding of health data, making the device accessible to a broad range of users, regardless of their technical expertise.

The present invention provides a novel architecture for integrating artificial intelligence (AI) capabilities into handheld medical devices. The system leverages a distributed computing approach, partitioning AI processing tasks across on-device, edge, and cloud resources. This innovative architecture enables medical devices to deliver real-time, personalized insights and recommendations while overcoming the limitations of traditional on-device or cloud-only solutions.

The inventive system and process disclosed herein offers several improvements over existing approaches. By incorporating an edge processing layer, the architecture reduces latency, optimizes bandwidth usage, enhances data privacy and security, and improves overall system resiliency and scalability. The edge nodes, situated close to the medical devices, can perform intermediate AI computations, such as running machine learning models for pattern detection on sensor data streams. This allows for faster response times and reduces the amount of raw data transmitted to the cloud, ensuring efficient use of network resources and minimizing privacy risks.

One of the novel aspects of the invention lies in the intelligent partitioning of AI tasks across the three processing layers. The system employs a dynamic task allocation algorithm that considers factors such as computational complexity, data privacy requirements, and network conditions to determine the optimal distribution of AI workloads. For instance, the algorithm may assign simple rule-based algorithms and signal preprocessing tasks to the on-device layer, while offloading more complex pattern recognition and anomaly detection tasks to the edge nodes. The cloud layer is reserved for computationally intensive tasks, such as training deep learning models on large, diverse biomedical datasets and performing long-term data analysis.

Another novel feature of the invention is the use of a secure, hybrid communication protocol that ensures end-to-end encryption of sensitive medical data. The protocol employs a combination of lightweight cryptographic algorithms and hardware-based security modules to protect data at rest and in transit. When transmitting data from the device to the edge nodes, the system uses short-range, low-power communication technologies like Bluetooth Low Energy (BLE) or Wi-Fi Direct, while data exchange between the edge nodes and the cloud relies on cellular networks or Wi-Fi with robust security measures, such as Transport Layer Security (TLS) and Virtual Private Networks (VPNs). This hybrid approach guarantees the confidentiality and integrity of patient data throughout the distributed AI processing pipeline.

By leveraging a distributed computing approach and intelligently partitioning AI tasks across on-device, edge, and cloud resources, the system delivers real-time, secure, and scalable AI performance while addressing the shortcomings of traditional solutions, the disclosed architecture is an improvement in the technical field of AI and medical data processing system. It improves patient outcomes by improving the speed and efficacy of delivery of personalized healthcare services. Specifically, multisensor device-enhanced telehealth allows current telehealth (just an audio or audio/video call) to reach its full potential and become the entry point for every patient journey, saving patients time & money (avoiding unnecessary in-office follow-ups), increasing efficiency for providers, and increasing profits for insurers.

The disclosed invention presents a novel system for delivering personalized advertisements and interactions in public spaces using an integrated multi-sensor and AI-driven approach. This system is designed to enhance accuracy, address privacy concerns, and improve adaptability compared to existing technologies.

At a high level, the inventive solution incorporates an advanced array of imaging and sensing technologies, including cameras capable of high-resolution imaging across varying light conditions and sensors that can detect and analyze a broader range of biometric markers, such as gait and voice, beyond traditional facial recognition, and/or scleral microvasculature pattern detection. The AI component of the system utilizes machine learning algorithms optimized for real-time data processing and capable of dynamic learning. This enables the system to adapt to new data inputs and environmental changes over time, enhancing the personalization of content delivery.

The use of diverse sensors and associated AI algorithms, as disclosed in various embodiments of the invention, allows for high accuracy in individual recognition even in challenging environments. This addresses one of the limitations of prior art, which often fails in crowded spaces or in poor lighting conditions. By broadening the types of biometric markers and environmental factors it can process, the system is less likely to misidentify individuals, thereby improving the relevance and effectiveness of targeted content.

Furthermore, the various embodiments improve privacy safeguards by implementing advanced data handling protocols that anonymize personal data at the point of collection. This system design mitigates privacy concerns significantly by ensuring that personal data is not stored or processed in a manner that could lead to unauthorized access or misuse, making it a substantial improvement over prior solutions that involve storing and processing potentially sensitive biometric data.

The inventive embodiments provide an improved method for delivering personalized content in public spaces that is more accurate, respects user privacy to a greater extent, and is more adaptable to varying environmental conditions and data types than existing solutions is an improvement in the technical field of data processing and data analytics.

The present invention is a system and method for assisting providers (e.g. clinicians, physicians, nurses, etc.) with standard of care using artificial intelligence (AI). This AI based approach is designed to augment provider diagnosis by integrating patient statements, sensor data, and/or health records to suggest potential diseases and/or treatment steps. The AI system has the capacity to analyze large volumes of data more efficiently than human providers. This may assist a provider in reaching a diagnosis more efficiently and help to ensure that a given standard of care is being met. The system takes as input at least one of patient-reported symptoms, provider notes separate from and/or beyond patient-reported symptoms, and sensor data from medical and/or health/wellness devices. This information is processed and analyzed by at least one AI model to generate a list of potential diagnoses along with the likelihood of each diagnosis, and could include recommended next steps for a provider to take based on the relevant standard of care.

The AI model is trained on a large dataset comprised of at least one of patient-reported symptoms across a plurality of patients, provider notes associated with a plurality of patients, sensor data from medical devices, medical records associated with a plurality of patients, scientific literature, and expert provider knowledge. As such, it encapsulates a broad range of medical information that would be infeasible for an individual provider to memorize or reference in real-time. The model also learns from feedback provided by providers, allowing it to improve its performance over time.

For each potential diagnosis, the system may provide recommendations on next steps, such as additional tests to order and/or treatments to prescribe, based on accepted standards of care. This serves to remind providers of best practices and reduce variability in care.

By considering a comprehensive set of patient information and medical knowledge, and providing data-driven diagnostic support, the invention helps providers arrive at accurate diagnoses, and/or narrow down a list of potential diagnoses, more efficiently and with greater certainty. This has the potential to improve patient outcomes by reducing diagnostic errors and delays in treatment. It can also lower healthcare costs by avoiding unnecessary tests and procedures caused by misdiagnosis or inefficiently narrowing down potential diagnoses.

The invention improves upon existing solutions in several ways. First, it uses state-of-the-art AI and natural language processing techniques to analyze both structured and unstructured data, providing more holistic decision support. Second, it is designed to integrate seamlessly into a provider's workflow and provide real-time assistance during patient encounters. Third, the continuous learning capability allows the system to stay up-to-date with the latest medical knowledge, adapt to each provider's individual practice patterns that fit within an acceptable standard of care, and become more capable and accurate as it is trained on ever-expanding patient data (in type and volume). Together, these enhancements make the invention a powerful tool for augmenting and enhancing providers' diagnostic capabilities, leading to an improvement in speed and quality of patient care while reducing the cost of care.

The present invention is a system and method for providing users with personalized health assessments and warnings based on real-time analysis of sensor data, medical records, and user-inputted information. The system employs advanced machine learning algorithms to identify user-specific patterns and generate easily understandable feedback indicating potential health concerns.

The invention addresses the technical limitations of current health tracking devices by integrating and analyzing data from multiple sources in real-time. The system is configured to collect sensor readings from various wearable and non-wearable devices, as well as retrieve relevant medical records, lab results, and user-provided symptom information. By synthesizing these disparate data streams, the invention creates a comprehensive picture of the user's health, enabling more accurate identification of potential issues.

The machine learning algorithms employed by the invention are specifically designed to handle the complexity and variability of human health data across diverse populations. Unlike conventional rule-based systems, the invention's adaptive algorithms continuously refine their analysis based on cumulative user data, improving accuracy over time. The algorithms are capable of identifying subtle, user-specific patterns that may be indicative of health concerns, even when individual sensor readings fall within generic population-based ranges.

A key feature of the invention is its ability to provide meaningful, actionable feedback to users without crossing the line into diagnosis. The system generates a graded warning system, such as a color-coded scale or numerical rating, to indicate the severity of potential health concerns. This non-diagnostic yet informative approach empowers users to make informed decisions about seeking medical attention, reducing the risk of both unnecessary doctor visits and dangerous delays in care. This is not to say that the invention is incapable of diagnostics, but that one key application comprises use as a warning tool.

The invention represents a significant improvement over prior art solutions by overcoming their technical limitations in data integration, analysis, and user communication. The system's ability to collect and synthesize data from multiple sources in real-time, coupled with its advanced machine learning capabilities, allows for the generation of highly personalized and accurate health assessments. The invention's graded warning system provides users with easily understandable and actionable information, promoting proactive health management without encroaching on the domain of licensed medical professionals.

In summary, the present invention addresses the technical shortcomings of existing health tracking devices by providing an integrated, adaptive platform for real-time data analysis and personalized health feedback. By empowering users to make informed decisions about their health based on comprehensive, user-specific data analysis, the invention represents a significant advancement in the field of personal health monitoring.

The invention pertains to a system and method for integrating real-world functionalities, such as healthcare services, into a virtual environment known as the metaverse. This is achieved by utilizing digital avatars and enhanced security measures such as those based on digital ledgers and/or blockchain technology. The invention addresses the issue of maintaining anonymity and security while accessing healthcare and other services within the metaverse, without the need for users to leave the virtual environment to complete tasks that require interaction with the real world.

The invention involves creating avatars that users can customize to either closely resemble their real-world appearance or significantly differ from it to maintain anonymity, particularly during sensitive health consultations. Healthcare services are provided in a virtual setting that the user can access from their virtual residence or at a designated virtual healthcare facility. This virtual healthcare access eliminates the discomfort associated with traditional telehealth encounters, where the exchange of sensitive information or physical and/or psychological embarrassment presents privacy concerns.

The invention incorporates security measures, such as digital ledgers and/or blockchain technology, secure tokens, and the like, to securely manage and verify user identity without exposing sensitive personal information. This is accomplished by using secure tokens and possibly integrating IP history and/or behavioral analysis and/or previously stored health data to authenticate the user's identity further. These measures aim to enhance security and privacy in telehealth services.

The invention allows for seamless integration of real-world tasks within the metaverse. For example, users can complete healthcare visits and optionally have physical treatment items delivered to their real-world location. This feature leverages the blend of real-world and virtual-world functionalities, enhancing user convenience and time efficiency by allowing them to stay within the immersive experience of the metaverse.

The invention addresses the need for privacy, security, and functionality within the space of the metaverse. Existing virtual reality technologies and telehealth systems do not offer the level of integration, security, and user immersion provided by this invention. By facilitating a secure, convenient, and integrated approach to accessing healthcare and completing daily tasks in a virtual environment, this invention enables a more realistic and seamless transition between real-world activities and their digital counterparts in the metaverse.

The present invention relates to a system and method for integrating real-world functionalities into a virtual environment, such as the metaverse, by utilizing digital avatars and enhanced security measures based on digital ledger and/or blockchain technology. The system allows users to access various services, including healthcare services, within the metaverse without the need to leave the virtual environment to complete tasks that require interaction with the real world.

The system comprises a virtual environment, such as the metaverse, where users are represented by digital avatars. These avatars serve as a means for users to interact with the virtual environment and access various services, including healthcare services. The system also includes a digital ledger and/or blockchain-based security framework that ensures the anonymity and security of user data and transactions within the virtual environment.

When a user wishes to access a real-world service, such as healthcare, within the metaverse, they can do so through their digital avatar. The avatar may be one they created for the metaverse environment, or an altered version specifically for their healthcare interaction. The avatar interacts with a virtual representation of the service provider, such as a virtual clinic or hospital. The user can then request specific services, such as medical consultations, diagnostic tests, or treatment plans, through their avatar.

The system securely transmits the user's request and any relevant data, such as medical history or symptoms, to the real-world service provider using digital ledger and/or blockchain technology. This ensures that the user's data remains confidential and tamper-proof throughout the process. The service provider can then review the user's request and provide the necessary services or feedback within the virtual environment.

The digital ledger and/or blockchain-based security framework also facilitates secure payment transactions between the user and the service provider. The user can authorize payments using their digital avatar, and the transactions are recorded on the digital ledger and/or blockchain, ensuring transparency and immutability.

Throughout the process, the user's anonymity is maintained, as their real-world physical identity is not revealed to the service provider (however, all information regarding their identity and eligibility to receive appropriate treatment is validated during the interaction while the maximum amount of anonymity legally possible is maintained) unless explicitly authorized by the user. This allows users to access real-world services within the metaverse without compromising their privacy or security and while avoiding unnecessary embarrassment.

The invention also enables the integration of other real-world functionalities into the metaverse, such as education, commerce, and social services. By utilizing digital avatars and digital ledger and/or blockchain-based security measures, the system creates a seamless and secure interface between the virtual environment and the real world, enhancing the functionality and utility of the metaverse.

In summary, the present invention provides a system and method for integrating real-world services, such as healthcare, into a virtual environment, while maintaining user anonymity and data security through the use of digital avatars and digital ledger and/or blockchain technology. This innovation enhances the capabilities of the metaverse and enables users to access a wide range of services without leaving the virtual environment.

BRIEF DESCRIPTION OF THE DRAWING FIGURES

The accompanying drawings illustrate several embodiments and, together with the description, serve to explain the principles of the invention according to the embodiments. It will be appreciated by one skilled in the art that the particular arrangements illustrated in the drawings are merely exemplary and are not to be considered as limiting of the scope of the invention or the claims herein in any way.

DETAILED DESCRIPTION OF EMBODIMENTS

Figure 1:
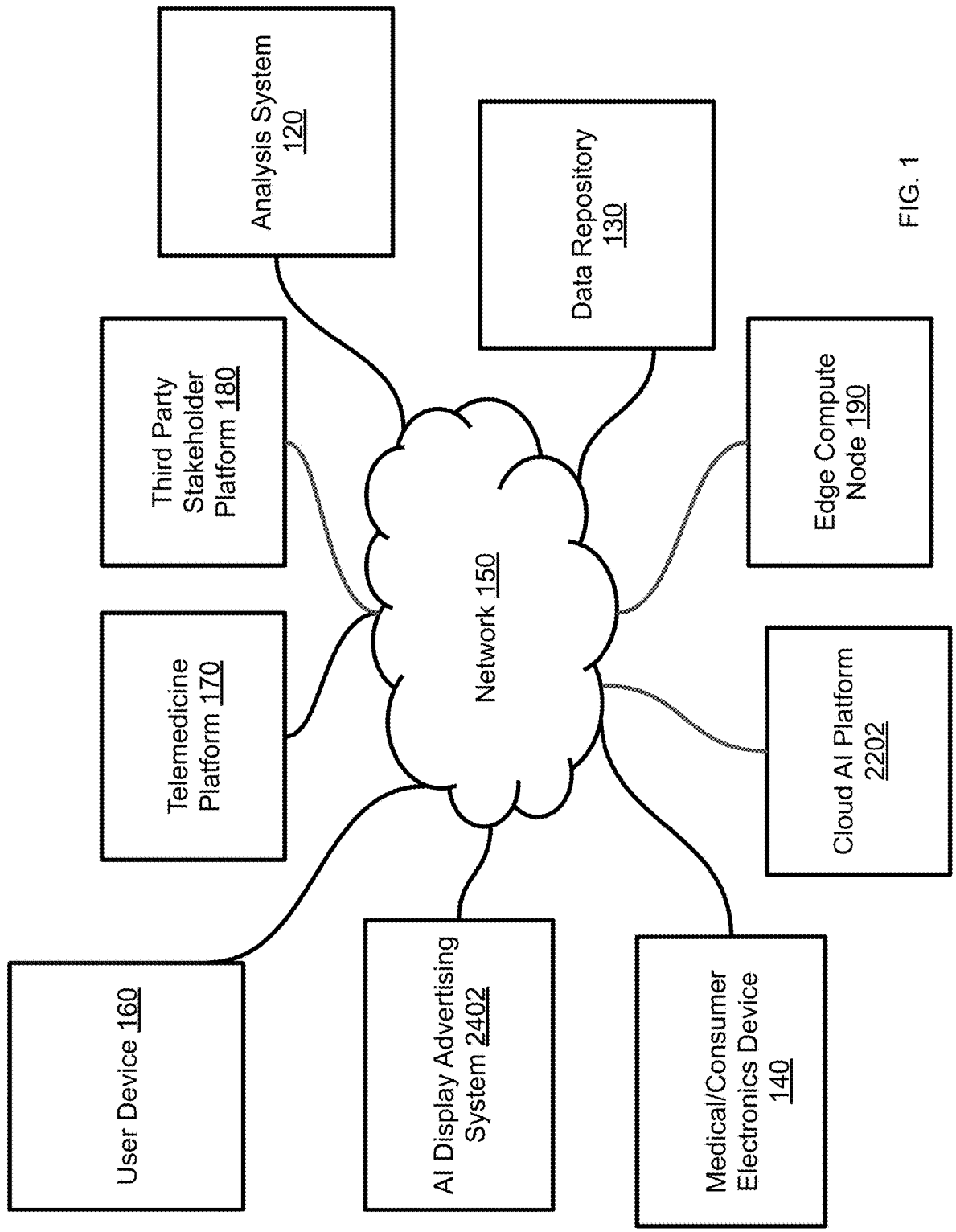
FIG. 1 illustrates an environment for remote and/or automated medical diagnosis in accordance with an exemplary embodiment of the invention.

The present invention is for a hand-held medical diagnostic device that integrates multiple health monitoring sensors in a compact and user-friendly design. The invention is described by reference to various elements herein. It should be noted, however, that although the various elements of the inventive apparatus are described separately below, the elements need not necessarily be separate. The various embodiments may be interconnected and may be cut out of a singular block or mold. The variety of different ways of forming an inventive apparatus, in accordance with the disclosure herein, may be varied without departing from the scope of the invention.

Generally, one or more different embodiments may be described in the present application. Further, for one or more of the embodiments described herein, numerous alternative arrangements may be described; it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices and parts that are connected to each other need not be in continuous connection with each other, unless expressly specified otherwise. In addition, devices and parts that are connected with each other may be connected directly or indirectly through one or more connection means or intermediaries.

A description of an aspect with several components in connection with each other does not imply that all such components are required. To the contrary, a variety of optional components may be described to illustrate a wide variety of possible embodiments and in order to more fully illustrate one or more embodiments. Similarly, although process steps, method steps, or the like may be described in a sequential order, such processes and methods may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, or method is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Alternate implementations are included within the scope of various embodiments in which, for example, functions may be executed out of order from that shown or discussed, including substantially concurrently or in reverse order, depending on the functionality involved, as would be understood by those having ordinary skill in the art.

The disclosed invention provides a system for delivering personalized advertisements and interactive content to individuals in public spaces through a combination of imaging and sensing technologies, supported by advanced artificial intelligence (AI). The system includes several components designed to work in concert to achieve accurate and efficient identification and personalization.

The system employs multiple high-resolution cameras strategically positioned to capture images across various light conditions. These cameras are capable of high magnification and are equipped with software that utilizes AI for the recognition of individuals based on facial features, even in low light or crowded settings. To enhance recognition capabilities, the system also integrates additional sensors that detect other biometric markers such as gait patterns and voice frequencies.

The AI components incorporate machine learning algorithms that process data collected in real time. The algorithms are designed to learn dynamically from ongoing interactions and environmental inputs, which allows the system to adapt its responses based on changing conditions and accumulated data over time.

Data privacy is maintained through a protocol that anonymizes personal data at the point of collection. This is achieved by processing personal data locally on the device to determine relevant content to be displayed or interacted with, after which the data is immediately anonymized before any form of storage or further processing takes place. This ensures that personal data is not stored or handled in any identifiable form, thereby safeguarding user privacy.

In practice, the system uses its capabilities to deliver targeted advertisements and content by analyzing the recognized data and selecting content that is tailored to the perceived preferences and behaviors of the individual. This content is then displayed on integrated screens or communicated via speakers, which are part of the system, enhancing the engagement and experience of the passerby.

Through these mechanisms, the invention provides a method for interacting with individuals in public spaces in a way that is both personalized and respectful of privacy considerations, while being adaptable to a wide range of environmental conditions and individual behaviors. The system represents an advancement in the field by integrating comprehensive data collection with robust real-time processing and privacy management.

The inventive systems and methods (hereinafter sometimes referred to more simply as "system" or "method") described herein facilitate remote and/or automated medical diagnosis. Specifically, a medical/consumer electronics device, comprising a plurality of sensors, may receive information from at least two sensors. The medical/consumer electronics device may transmit the information received from the at least two sensors over a network to a user device, which may further transmit the data to a remote server hosting a remote analysis platform. The remote server may use artificial intelligence (AI) and the information received from the at least two sensors to determine a diagnosis, an urgency level, and/or a recommendation and transmit a signal indicative of the determined diagnosis, urgency level, and/or recommendation over the network to the medical/consumer electronics device. The medical/consumer electronics device may display the determined diagnosis, urgency level, and/or recommendation. The present invention reduces time and expense associated with getting a medical diagnosis. The present invention facilitates medical diagnosis without exposing medical personnel to possibly contagious patients, and without users of the invention being exposed to possibly contagious patients or environments in public healthcare settings.

One or more different embodiments may be described in the present application. Further, for one or more of the embodiments described herein, numerous alternative arrangements may be described; it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural, logical, software, electrical and other changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible embodiments and in order to more fully illustrate one or more embodiments. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order or step). Moreover, the illustration of a ractical. Further, some steps may be performed simultaneously despite being described or implied as occurring non-simultaneously (e.g., because one step is described after the other process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, method, or algorithm is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various embodiments in which, for example, functions may be executed out of order from that shown or discussed, including substantially concurrently or in reverse order, depending on the functionality involved, as would be understood by those having ordinary skill in the art.

Conceptual Architecture

FIG. 1 illustrates an environment for remote and/or automated medical diagnosis in accordance with an exemplary embodiment of the invention. The environment comprises a medical/consumer electronics device 140, an analysis system 120, a data repository 130, a network 150, a user device 160, a telemedicine platform 170, and a third party stakeholder platform 180. The various computing devices described herein are exemplary and for illustration purposes only. The system may be reorganized or consolidated, as understood by a person of ordinary skill in the art, to perform the same tasks on one or more other servers or computing devices without departing from the scope of the invention.

The medical/consumer electronics device 140 may comprise a plurality of sensors. The medical/consumer electronics device 140 may comprise a browser for accessing a web application hosted on the analysis system 120. The medical/consumer electronics device 140 may comprise an application for interacting with a web application hosted on the analysis system 120. The medical/consumer electronics device 140 may comprise an application obtained from the analysis system 120. The medical/consumer electronics device 140 may transmit data collected from the plurality of sensors to the analysis system 120 via the network 150. The medical/consumer electronics device 140 may receive a diagnosis, an urgency level, and/or a recommendation from the analysis system 120 via the network 150. The medical/consumer electronics device 140 may comprise a device a consumer uses at home. The medical/consumer electronics device 140 may comprise sensors as attachments to a user device, such as a laptop or smartphone. The medical/consumer electronics device 140 may comprise a device used at a medical office. For example, the medical/consumer electronics device 140 may suggest to a doctor drugs to prescribe to a patient, specialists to refer a patient to, imaging or other diagnosis procedures to suggest for a patient, admittance of a patient to a hospital or emergency room, etc. The medical/consumer electronics device 140 may comprise a device for collecting biometrics to determine if access to an area should be given to an individual. The medical/consumer electronics device 140 may transfer data to a remote security server (not shown) for biometric matching. The medical/consumer electronics device 140 may retrieve data from the remote security server for biometric matching. The medical/consumer electronics device 140 may be used in advertising to determine that a user is positioned in front of a digital billboard (not shown). The medical/consumer electronics device 140 may identify the user and/or characteristics of the user and facilitate targeted ads to the user based on the identified user and/or identified characteristics. The medical/consumer electronics device 140 may transfer data to a remote ad server (not shown) for targeted advertising. The medical/consumer electronics device 140 may retrieve data from the remote ad server for targeted advertising. The medical/consumer electronics device 140 may cause the digital billboard to display a targeted advertisement for the user. The medical/consumer electronics device 140 will be described in greater detail in reference to FIG. 2. The medical device/consumer electronics 140 device may comprise sensors as wired or wireless attachments to a user device, such as a laptop, tablet, or smartphone. The medical/consumer electronics/advertising/security device may comprise a device for collecting biometrics to determine if access to an area should be given to an individual. The medical/consumer electronics/advertising/security device may be used in advertising to determine that a user is positioned in front of a digital billboard.

The analysis system 120 may comprise a remote server. The analysis system 120 may comprise one or more computing devices. The analysis system 120 may comprise a cloud computing environment. The analysis system 120 may host a website. The analysis system 120 may host a web application. The analysis system 120 may provide applications, such as mobile applications, for download by the medical/consumer electronics device 140 via the network 150. The analysis system 120 may receive information from sensors from the medical/consumer electronics device 140 via the network 150. The analysis system 120 may determine a diagnosis, an urgency level, and/or a recommendation based on the received information from sensors. The analysis system 120 may transmit the determined diagnosis, urgency level, and/or recommendation to the medical/consumer electronics device 140 via the network 150. The analysis system 120 may use data, such as artificial intelligence (AI) training data, from the data repository 130 via the network 150. The analysis system 120 may store data, such as data received from a particular medical/consumer electronics device and associated determined diagnoses, urgency levels, and/or recommendations, in the data repository 130 via the network 150. The analysis system 120 will be described in greater detail in reference to FIG. 3. The analysis system may send or receive data, such as artificial intelligence training or analyzed data or results (for example and without limitation, diagnosis, urgency level, and/or recommendation), to or from the data repository via the network. The analysis system may transmit the determined diagnosis, urgency level, and/or recommendation to the medical device or a device connected to it (wired or wirelessly) via the network.

The data repository 130 may comprise data storage. The data repository 130 may comprise AI training data. The data repository 130 may comprise data sets. The data sets may associate information received from particular medical/consumer electronics devices 140, such as information from sensors. The data sets may comprise a diagnosis, urgency level, and/or recommendation associated with information received from a particular medical/consumer electronics device 140. The data repository 130 may comprise biometric data. The data repository 130 may comprise information for targeting advertising. The data repository may comprise one or more AI engines and/or algorithms.

The network 150 may facilitate communication between the medical/consumer electronics device 140, the analysis system 120, the data repository 130, the user device 160, the telemedicine platform 170, and the third party stakeholder platform 180, as well as other devices, as would be understood by a person of ordinary skill in the art.

The network 150 generally represents a network or collection of networks (such as the Internet or a corporate intranet, or a combination of both) over which the various components illustrated in FIG. 1 (including other components that may be necessary to execute the system described herein, as would be readily understood to a person of ordinary skill in the art). In particular embodiments, network 150 is an intranet, an extranet, a virtual private network (VPN), a local area network (LAN), a wireless LAN (WLAN), a wide area network (WAN), a metropolitan area network (MAN), a portion of the Internet, or another network 150 or a combination of two or more such networks 150. One or more links connect the systems and databases described herein to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable network 150, and any suitable link for connecting the various systems and databases described herein.

The network 150 connects the various systems and computing devices described or referenced herein. In particular embodiments, network 150 is an intranet, an extranet, a virtual private network (VPN), a local area network (LAN), a wireless LAN (WLAN), a wide area network (WAN), a metropolitan area network (MAN), a portion of the Internet, or another network or a combination of two or more such networks 150. The present disclosure contemplates any suitable network 150.

One or more links couple one or more systems, engines or devices to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable links coupling one or more systems, engines or devices to the network 150.

In particular embodiments, each system or engine may be a unitary server or may be a distributed server spanning multiple computers or multiple datacenters. Systems, engines, or modules may be of various types, such as, for example and without limitation, web server, news server, mail server, message server, advertising server, file server, application server, exchange server, database server, or proxy server. In particular embodiments, each system, engine or module may include hardware, software, or embedded logic components or a combination of two or more such components for carrying out the appropriate functionalities implemented or supported by their respective servers. For example, a web server is generally capable of hosting websites containing web pages or particular elements of web pages. More specifically, a web server may host HTML files or other file types, or may dynamically create or constitute files upon a request, and communicate them to one or more computing device(s) or other devices in response to HTTP or other requests from one or more computing device(s) or other devices. A mail server is generally capable of providing electronic mail services to various one or more computing device(s) or other devices. A database server is generally capable of providing an interface for managing data stored in one or more data stores.

In particular embodiments, one or more data storages may be communicatively linked to one or more servers via one or more links. In particular embodiments, data storages may be used to store various types of information. In particular embodiments, the information stored in data storages may be organized according to specific data structures. In particular embodiments, each data storage may be a relational database. Particular embodiments may provide interfaces that enable servers or clients to manage, e.g., retrieve, modify, add, or delete, the information stored in data storage.

The system may also contain other subsystems and databases, which are not illustrated in FIG. 1, but would be readily apparent to a person of ordinary skill in the art. For example, the system may include databases for storing data, storing features, storing outcomes (training sets), and storing models. Other databases and systems may be added or subtracted, as would be readily understood by a person of ordinary skill in the art, without departing from the scope of the invention.

A first user may feel warm, have shortness of breath, a cough, and chest pains. The first user may use a thermometer of a first medical/consumer electronics device to take a body temperature. The first user may use a pulse oximeter of the first medical/consumer electronics device to take a heart rate and an oxygen saturation level. The first user may use a stethoscope of the first medical/consumer electronics device to listen to chest sounds. The body temperature may be 102 degrees Fahrenheit. The heart rate may be 92 beats per minute. The oxygen saturation level may be 89%. The chest sounds may comprise congested sounds. The first medical/consumer electronics device may transmit the body temperature, heart rate, oxygen saturation level, and chest sounds over a network to a telemedicine platform. The telemedicine platform may use artificial intelligence (AI) to determine a possible infection, likely related to a respiratory system. The telemedicine platform may determine that the possible causes comprise bacterial pneumonia, viral pneumonia, COVID-19, exacerbation of COPD, etc. The telemedicine platform may assign an urgency level of 4, on a scale of 1-5, 5 being the most urgent. The telemedicine platform may recommend contacting physician urgently and if unable to do so, proceed to urgent medical care facility. In one embodiment, the data repository may comprise an AI server/system/platform that analyzes the data and sends the results to the telemedicine platform and/or the medical/ consumer electronics/security/advertising device and/or any device connected to it (wired or wireless).

A second user may develop pains over the chest with numbness in the left arm, be sweating, feel very weak and have shortness of breath. The second user may use a thermometer of a second medical/consumer electronics device to take a body temperature. The second user may use a pulse oximeter of the second medical/consumer electronics device to take a pulse and an oxygen saturation level. The second user may use a high-magnification camera of the second medical/consumer electronics device to determine a blood pressure. The second user may use an electrocardiogram (EKG) to take heart measurements. The body temperature may be 80 degrees Fahrenheit. The pulse may be 106 beats per minute. The oxygen saturation level may be 90%. The blood pressure may be 90/60. The EKG heart measurements may reveal a heart rate of 92 beats per minute, an irregular heart beat, and an abnormal EKG pattern. The second medical/consumer electronics device may transmit the body temperature, pulse, oxygen saturation level, blood pressure, and EKG heart measurements over a network to a telemedicine platform. The telemedicine platform may use artificial intelligence (AI) to determine possible conditions comprise a heart attack, blood clots in lungs, pericarditis, etc. The telemedicine platform may assign an urgency level of 5, on a scale of 1-5, 5 being the most urgent. The telemedicine platform may recommend contacting a doctor urgently, proceeding to an urgent care facility promptly, or calling 911. In one embodiment, the data repository may comprise an AI server/system/platform that analyzes the data and sends the results to the telemedicine platform and/or the medical/consumer electronics/security/advertising device and/or any device connected to it (wired or wireless).

A third user may feel nausea and have vomiting, pains in the abdomen, very dark urine, and yellow skin. The third user may use a thermometer of a third medical/consumer electronics device to take a body temperature. The third user may use a pulse oximeter of the third medical/consumer electronics device to take a pulse and an oxygen saturation level. The third user may use a high-magnification camera of the third medical/consumer electronics device to take one or more eye images. The body temperature may be 99 degrees Fahrenheit. The pulse may be 92 beats per minute. The oxygen saturation level may be 96%. The blood pressure may be 90/60. The one or more eye images may reveal yellow sclera. The telemedicine platform may use artificial intelligence (AI) to determine possible conditions comprise gallbladder inflammation, gallstones, pancreatic tumor causing bile blockage, etc. The telemedicine platform may assign an urgency level of 3, on a scale of 1-5, 5 being the most urgent. The telemedicine platform may recommend contacting a telemedicine physician. The telemedicine platform may initiate a call with a telemedicine physician. In one embodiment, the data repository may comprise an AI server/system/platform that analyzes the data and sends the results to the telemedicine platform and/or the medical/consumer electronics/security/advertising device and/or any device connected to it (wired or wireless).

A fourth user may work in a secure area of an office building or seek access to a virtual secure area. In order to access the secure area, a fourth medical/consumer electronics device may be on an adjustable stand, such that a height of a high-magnification camera of the fourth medical/consumer electronics device may be adjusted to an eye level of the fourth user, or may be part of a network-connected wearable headset. The high-magnification camera may take a picture or video of the unique, individualized pattern of conjunctival vessels, and/or white space between conjunctival vessels, within a predefined area of at least 0.25 millimeter squared and maximum 4 inches squared, of the fourth user to identify the fourth user as a user with access credentials to the physical or virtual secure area and allow the fourth user to have access to the secure area.

A fifth user may stand in front of a digital billboard. A fifth medical/consumer electronics device associated with the digital billboard may comprise a variety of sensors for a user, including one or more microphones for detecting noise a user makes, a thermometer to detect a user's body temperature, a barometer to detect a change in atmospheric pressure due to the presence of a user, a bluetooth receiver for detecting and/or identifying a user device a user may carry, and/or multiple cameras for identifying users and/or user features and/or user object features, such as a vehicle license plate, if the user is driving towards of a digital billboard. In one embodiment, conjunctival vasculature and/or white space between conjunctival vasculature may be measured. Additionally, data from digital billboard sensors may be combined from data on in-house and/or affiliated and/or non-affiliated servers from the applicant and/or other providers related to the user (with whom the user has previously shared data), which the user has previously provided permission for 3rd parties to access for the purpose of targeted advertising. The variety of sensors may be used to identify the fifth user and/or characteristics of the fifth user. Based on the identity of the fifth user and/or identified characteristics of the fifth user, a targeted advertisement for the fifth user may be selected and displayed on the digital billboard. Speakers associated with the digital billboard may call out to the fifth user by name to get the attention of the fifth user.

User devices 160 refers to computing devices that may be used to display user interface elements associated that may be generated by the relational database engine 102. The user device 160 (herein referred to as user input device, user device, or client device) may include, generally, a computer or computing device including functionality for communicating (e.g., remotely) over the network 150, user devices 160 may be a server, a desktop computer, a laptop computer, personal digital assistant (PDA), an in- or out-of-car navigation system, a smart phone or other cellular or mobile phone, or mobile gaming device, among other suitable computing devices, user devices 160 may execute one or more client applications, such as a web browser (e.g., Microsoft Windows Internet Explorer, Mozilla Firefox, Apple Safari, Google Chrome, and Opera, etc.), or a dedicated application to submit user data, or to make prediction queries over the network 150.

In particular embodiments, each user device 160 may be an electronic device including hardware, software, or embedded logic components or a combination of two or more such components and capable of carrying out the appropriate functions implemented or supported by the user device 160. For example and without limitation, user device 160 may be a desktop computer system, a notebook computer system, a netbook computer system, a handheld electronic device, or a mobile telephone. The present disclosure contemplates any user device as the user device 160. The user device 160 may enable a network user at the user device 160 to access network 150. The user device 160 may enable its user to communicate with other users at other client devices.

The user device 160 may have a web browser, such as MICROSOFT INTERNET EXPLORER, GOOGLE CHROME or MOZILLA FIREFOX, and may have one or more add-ons, plug-ins, or other extensions, such as TOOL-BAR or YAHOO TOOLBAR. The user device 160 may enable a user to enter a Uniform Resource Locator (URL) or other address directing the web browser to a server, and the web browser may generate a Hyper Text Transfer Protocol (HTTP) request and communicate the HTTP request to server. The server may accept the HTTP request and communicate to the user device 160 one or more Hyper Text Markup Language (HTML) files responsive to the HTTP request. The user device 160 may render a web page based on the HTML files from server for presentation to the user. The present disclosure contemplates any suitable web page files. As an example and not by way of limitation, web pages may render from HTML files, Extensible Hyper Text Markup Language (XHTML) files, or Extensible Markup Language (XML) files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a web page encompasses one or more corresponding web page files (which a browser may use to render the web page) and vice versa, where appropriate.

The user device 160 may also include an application that is loaded onto the user device 160. The application obtains data from the network 150 and displays it to the user within the application interface.

This disclosure contemplates any suitable number of user devices 160, including computing systems taking any suitable physical form. As example and not by way of limitation, computing systems may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, or a combination of two or more of these. Where appropriate, the computing system may include one or more computer systems; be unitary or distributed; span multiple locations; span multiple machines; or reside in a cloud, which may include one or more cloud components in one or more networks. Where appropriate, one or more computing systems may perform without substantial spatial or temporal limitation one or more steps of one or more methods described or illustrated herein. As an example, and not by way of limitation, one or more computing systems may perform in real time or in batch mode one or more steps of one or more methods described or illustrated herein. One or more computing systems may perform at different times or at different locations one or more steps of one or more methods described or illustrated herein, where appropriate. In one embodiment, the user device 150 communicates and/or interfaces with the medical/consumer electronics device to obtain data from the device via a communication channel disclosed herein, and may transmit that data to the analysis system 120 via a communication channel disclosed herein.

The telemedicine platform 160 enables communication between a patient and a provider such as a physician, nurse practitioner, etc. The telemedicine platform 160 may enable communication amongst any user associated with any of the devices described herein.

All of the devices described herein may include a communication module for communicating with other devices described herein as well as devices that are not disclosed herein. The communication module may communicate via a wired connection (e.g., including a physical connection such as a cable with a suitable connection interface such as USB, mini-USB, etc.) and/or a wireless network (e.g., through NFC, Bluetooth, WiFi, RFID, or any type of digital network that is not connected by cables). For example, devices may directly communicate with each other in pairwise connection (1:1 relationship), or in a hub-spoke or broadcasting connection ("one to many" or 1: m relationship). As another example, the devices may communicate with each other through mesh networking connections (e.g., "many to many", or m: m relationships), such as through Bluetooth mesh networking. Wireless communication may use any of a plurality of communication standards, protocols, and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), or any other suitable communication protocol. Some wireless network deployments may combine networks from multiple cellular networks (e.g., 3G, 4G, 5G) and/or use a mix of cellular, WiFi, and satellite communication.

The third party stakeholder platform 180 may comprise third parties such as, but not limited to, insurance companies, hospitals, pharmacies, etc. In one embodiment, the third party stakeholder platform 180 may receive information from the medical/consumer electronics device 140, telemedicine platform 170, analysis system 120, and/or data repository 130 for preventive health purposes, overall healthcare cost savings, and reduced deductibles/premiums, etc.

The edge compute node (190) is a computing device that acts as an intermediary between the handheld medical device and the cloud computing platform (120). Its primary function is to offload computationally intensive tasks from the handheld device's onboard processor (222), providing rapid processing and analysis of time-sensitive data.

The edge node (190) features a system-on-chip (SoC) processor (192) with a heterogeneous architecture that includes multiple high-performance CPU cores, GPU cores, and dedicated AI accelerators. This enables the edge node to efficiently handle complex workloads such as real-time image enhancement, signal processing, and machine learning inference.

The edge node (190) is equipped with a range of connectivity options, including Wi-Fi 6 (802.11ax), 5G cellular, and Ethernet, allowing it to communicate with the handheld device and other network resources. When the handheld device's onboard processor (222) determines that a task should be offloaded, it establishes a secure connection with the edge node (190) using WPA3 encryption over the Wi-Fi 6 link.

Upon receiving a task from the handheld device, the edge node's (190) processor allocates the necessary compute resources and begins processing the data. The edge node (190) has access to a local high-speed storage system, which it uses to cache frequently accessed data and intermediate results. This minimizes the need for repeated data transfers and improves overall system performance.

The edge node (190) also includes a dedicated security module (196) that provides hardware-based encryption and secure key management. This ensures that all data processed by the edge node remains confidential and tamper-proof. The security module (196) works in conjunction with the onboard processor's (222) security features to create an end-to-end secure environment.

One of the advantages of the edge compute node (190) is its ability to process data with low latency. By being located in close proximity to the handheld device, the edge node can receive, process, and return results quickly, enabling real-time diagnostics and rapid user feedback. This is particularly important for applications like real-time image enhancement from the high-magnification camera (202) or noise reduction algorithms for the digital stethoscope (206).

In addition to processing tasks offloaded by the handheld device, the edge node (190) can also communicate with the cloud computing platform (120) to access additional resources or update its machine learning models. The edge node (190) intelligently manages the flow of data between the handheld device, itself, and the cloud, ensuring optimal resource utilization and minimizing network congestion.

The edge compute node (190) is designed to be flexible and scalable, allowing it to adapt to the changing needs of the handheld medical device and its users. It can be easily upgraded with new hardware and software components to support additional functionality or improved performance.

In various embodiments, the edge compute node (190) and the cloud computing platform (120) collaborate to provide a comprehensive, efficient, and secure healthcare solution. In one embodiment, the edge node preprocesses and filters data, while the cloud platform aggregates and analyzes data from multiple sources, enabling advanced insights and personalized recommendations. This distributed computing architecture leverages the respective strengths of the edge node (190) and the cloud platform (500) to enhance the handheld medical device's diagnostic capabilities and user experience.

The ai display advertising system 2402 comprises an integrated system of sensors, processors, and displays designed to provide personalized advertising experiences based on biometric data captured from individuals. In one embodiment, the system utilizes an array of hardware and software to detect, analyze, and respond to the physical and behavioral characteristics of passersby to serve advertisements.

At a high level, the device includes a set of high-resolution cameras and specialized sensors aimed at capturing a wide range of biometric data. The cameras are positioned to take facial images from multiple angles, which aids in accurate facial recognition across different lighting conditions and movements and/or scleral microvasculature pattern detection. Complementing the visual data, gait sensors such as pressure-sensitive floor mats or depth cameras analyze the walking patterns of individuals, providing another layer of behavioral biometrics. Additionally, near-infrared (NIR) cameras may be utilized to enhance biometric data collection by capturing vein patterns, which are unique to each individual and visible under NIR light due to the differential absorption rates between veins and surrounding tissues.

The audio component of the system is handled by high-quality microphones that capture voice samples. These samples are used for voice signature analysis, adding a further personalized dimension to the data collection process. This comprehensive sensor suite feeds data into the system's processors where advanced AI algorithms analyze the collected biometrics to identify individuals and tailor advertisements specifically designed for them.

Once the data is processed and an appropriate advertisement is selected, it is displayed to the individual through one or more digital displays and/or speakers. These displays and/or speakers are strategically placed to ensure maximum visibility to the targeted individual, enhancing the likelihood of engagement with the advertised content.

Alternative configurations of the ai display advertising system 2402 could utilize different types of biometric sensors or data collection methodologies. For example, instead of pressure-sensitive mats for gait analysis, alternative systems might employ accelerometer-based wearable devices that provide data on body movement and dynamics. Similarly, instead of NIR cameras for vein pattern recognition, thermal imaging could be used as an alternative method to capture unique biometric identifiers based on body heat signatures. In terms of voice recognition, alternatives might include using advanced signal processing tools to filter and analyze background noise, enhancing voice capture accuracy in noisy environments. Each of these alternatives offers different approaches to capturing biometric data, which can be utilized depending on specific application needs or environmental constraints.

Medical/Consumer Electronics Device

Figure 2:
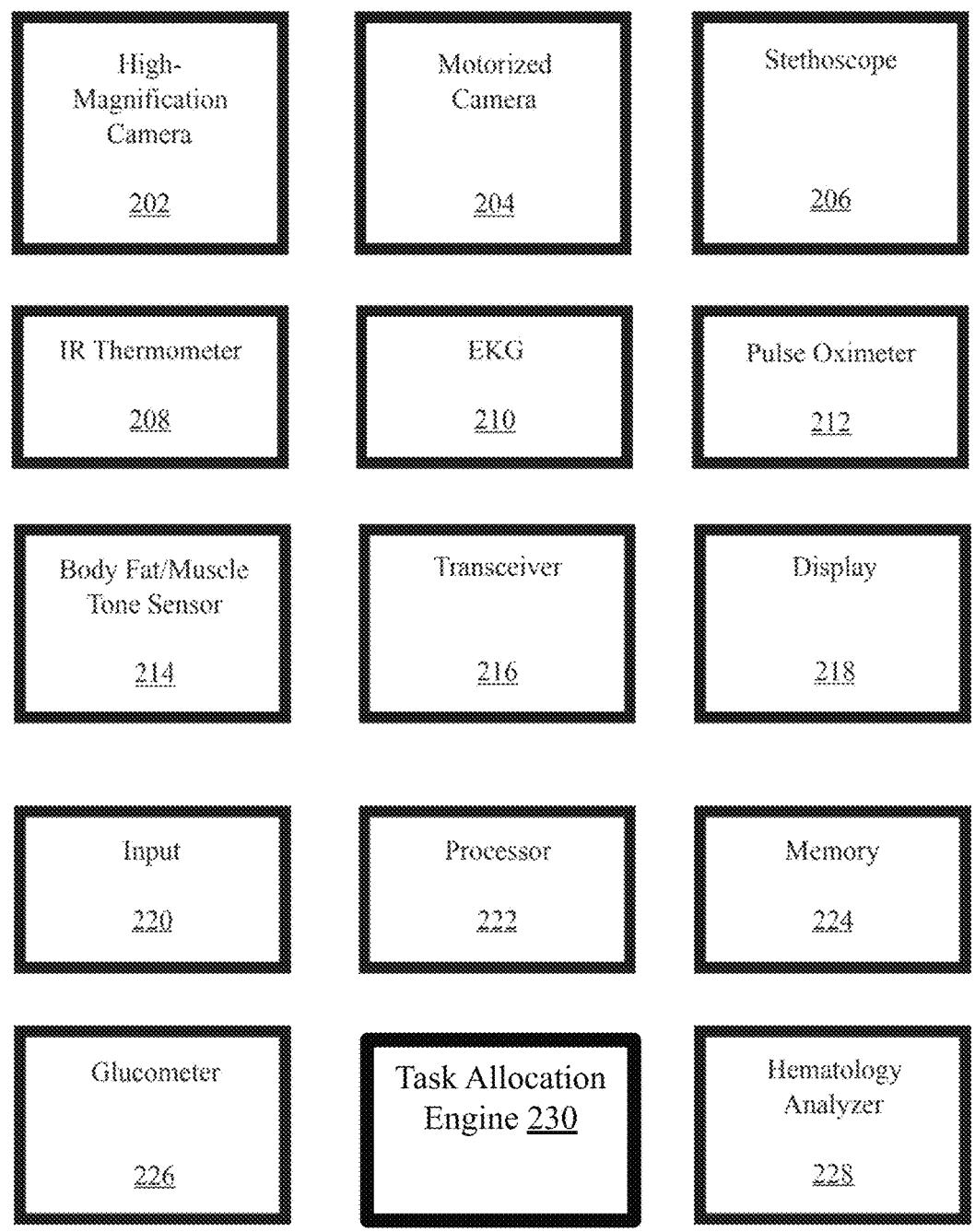
FIG. 2 illustrates an example medical/consumer electronics device in accordance with an exemplary embodiment of the invention.

FIG. 2 illustrates an example medical/consumer electronics device 200 in accordance with an exemplary embodiment of the invention. The example medical/consumer electronics device 200 may receive information about a user from sensors. The example medical/consumer electronics device 200 may receive information about a user from the sensors for medical diagnosis purposes. The example medical/consumer electronics device 200 may receive information about a user from the sensors for identification purposes. The example medical/consumer electronics device 200 may receive information about a user from the sensors for targeted advertisement purposes. The example medical/consumer electronics device 200 may be the same or similar to the medical/consumer electronics device 140 in FIG. 1. The example medical/consumer electronics device 200 comprises a high-magnification camera 202, a motorized camera 204, a stethoscope 206, an infrared (IR) thermometer 208, an electrocardiogram (EKG) 210, a pulse oximeter 212, a body fat and/or muscle tone sensor 214, a transceiver 216, a display 218, an input device 220, a processor 222, memory 224, a glucometer 226, and a hematology analyzer 228. Although not shown, an exemplary medical/consumer electronics device may also comprise one or more microphones for detecting noise a user makes, one or more speakers for providing audio to a user, a barometer to detect a change in atmospheric pressure due to the presence of a user, a tongue depressor to clear a user's mouth for throat images and/or video, a urine analyzer to detect and/or quantify a number of analytes including bilirubin, protein, glucose and red blood cells in a user's urine, and/or a bluetooth receiver for detecting and/or identifying a user device a user may carry. Although only one of each sensor is shown in the example medical/consumer electronics device 200, an exemplary medical/consumer electronics device may comprise multiple types of a particular sensor. For example, an exemplary medical/consumer electronics device may comprise multiple high-magnification cameras. Other systems and databases may be used, as would be readily understood by a person of ordinary skill in the art, without departing from the scope of the invention. The example medical device may receive information about a user from the sensors for informational and/or entertainment purposes. In one embodiment, the sensors may include one or more speakers and/or one or more microphones, in addition to the ones described herein.

The high-magnification camera 202 may comprise one or more light-emitting diodes (LEDs). The high-magnification camera 202 may capture high quality images and/or video of a patient's eye and/or skin. The high-magnification camera 202 may zoom in on vessels (veins/venules and/or arteries/arterioles) and/or the space in between such vessels in a patient's eye and capture video of blood flowing through eye vessels (veins/venules and/or arteries/arterioles) and/or the space in between such vessels to be used to calculate a blood pressure for the user. The high-magnification camera 202 may capture a user's conjunctival vasculature to be used for identification of the user and/or advertising. The high-magnification camera 202 may capture an object associated with a user, such as a vehicle license plate, to be used for identification of the user. The high-magnification camera module (202) comprises an image sensor with a high resolution paired with an integrated multi-element spherical and/or aspherical glass lens system providing optical magnification for skin and ocular inspection, and an annular LED array with adjustable brightness and/or color temperature surrounding the magnification stack. Other configurations of one or more LEDs and lenses may also be used as would be apparent to a person of ordinary skill in the art. . . . The high-magnification camera module (202) further comprises an embedded encryption engine for securing captured images and videos, and a physically unclonable function (PUF) circuit for generating unique cryptographic keys. The motorized camera 204 may comprise one or more LEDs. The motorized camera 204 may extend or retract as needed to get a clear position for image and/or video capturing. The motorized camera 204 may capture high quality images and/or video of a patient's ear, nose, and/or throat. The motorized camera may also be used as a tongue depressor. The motorized camera module (204) comprises an extension/retraction mechanism, a tilt mechanism, a camera sensor, a camera, a lighting element, and a microcontroller for visual inspection inside bodily cavities. The motorized camera module (204) further comprises a custom application-specific integrated circuit (ASIC) for controlling the extension/retraction and tilt mechanisms, and a configurable LED driver for adjusting the lighting element's brightness and color temperature. The stethoscope 206 may be used to capture audio from a patient's heart. The stethoscope 206 may be used to capture audio from a patient's lungs. The stethoscope 206 may be used to capture audio from a patient's arteries. The stethoscope 206 may be used to capture audio from a patient's vessels (veins/venules and/or arteries/arterioles) and/or the space in between such vessels. In one embodiment, the stethoscope module (206) comprises a digital MEMS microphone with a capacitive sensing element fitted behind an acoustically transparent port on a contoured rear surface of the device, and an integrated application-specific integrated circuit (ASIC) that performs bandpass filtering and amplification of the captured audio signals, and an analog encryption circuit for securing the audio data prior to digitization. The IR temperature 208 may capture a user's body temperature. In one embodiment, the infrared thermometer sensor module (208) comprises a precision thermistor for on-board thermal stabilization, an optical bandpass filter for optimal response convergence and immunity to environmental optical noise, and a metallic shield for electromagnetic isolation. The EKG 210 may comprise diodes. The EKG 210 may capture electrical signals in a patient's heart. In one embodiment, the electrocardiogram (EKG) sensor module (210) comprises multiple surface electrodes and supporting electronics customized for personal use, an instrumentation amplifier with high input impedance and low noise characteristics, and an analog encryption circuit for securing the EKG data prior to digitization. The pulse oximeter 212 may capture a patient's pulse. The pulse oximeter 212 may capture a patient's oxygen saturation level. In one embodiment, the pulse oximeter module (212) comprises a dual emitter light source combining peaks at 660 nm and 905 nm paired with a wide area silicon photodiode detector for determining arterial oxygen saturation and pulse rate, a time-multiplexed LED driver for alternating the red and infrared illumination sources, a transimpedance amplifier for converting the photodetector current to a voltage signal, and a lock-in amplifier for extracting the pulsatile signal components. The body fat and/or muscle tone sensor 214 may capture a patient's body fat. The body fat and/or muscle tone sensor 214 may capture a patient's muscle tone. In one embodiment, the body composition monitor module (214) comprises bioimpedance analysis circuitry customized for personal use to characterize body fat percentage and muscle mass distribution, a multi-frequency signal generator for applying excitation currents to the user's skin, a set of instrumentation amplifiers for measuring the voltage responses, and a machine learning model for estimating body fat percentage and muscle mass distribution from the bioimpedance data. The glucometer 226 may receive strips containing a blood sample. The glucometer 226 may determine a concentration of glucose in a blood sample. In one embodiment, the glucometer module (226) comprises a test strip port with an integrated strip ejection mechanism, an electrochemical sensor for measuring the glucose concentration in the blood sample, and a secure non-volatile memory for storing sensor calibration data. The hematology analyzer 228 may receive a blood sample. The hematology analyzer 228 may analyze cells in a blood sample. In one embodiment, the hematology analyzer module (228) comprises a microfluidic circuit for sample dilution and flow control, a multi-wavelength laser source for cell excitation, a set of photomultiplier detectors for measuring the scattered light intensities, and a digital signal processor for cell classification and counting.

Figure 27:
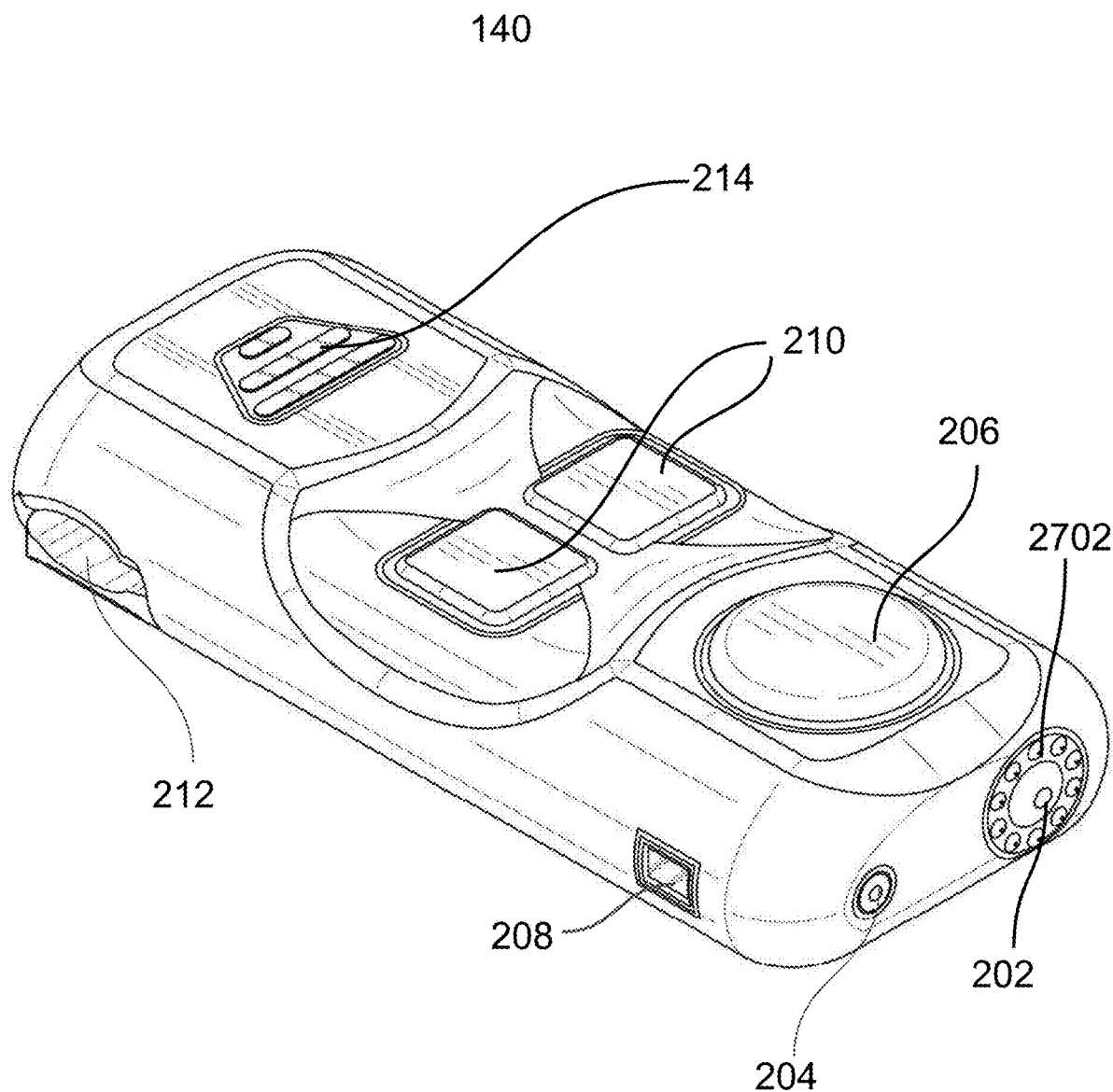
FIG. 27 illustrates an exemplary multi sensor handheld medical diagnostic device.

The integrated high-magnification camera module (202) enables detailed dermatological analysis and microscopic vascular visualization for advanced diagnostics in a compact form. The module centers around an image sensor with a high resolution (including, for example, but not limited to 2592×1944 resolution) paired with an integrated multi-element spherical and/or aspherical glass lens system providing optical magnification (including, for example, but not limited to 60-120× magnification) for skin and ocular inspection. The high-magnification camera module 202 is exemplarily illustrated as integrated into medical/consumer electronics device 140 in FIG. 27 and as 1103 in FIG. 11A In one embodiment, an annular LED array with adjustable color temperature may surround the lens stack as illustrated in FIG. 27 in element 2702. The LED array may provide adjustable front-facing illumination for shadow reduction and enhanced image quality regardless of ambient lighting conditions. This allows clear capture of tissue surfaces, lesions, blood capillaries, and other microstructures.

For blood pressure measurement, in accordance with an embodiment of the invention, real-time video magnification of minute blood vessel diameter changes in the retinal vasculature when paired with dedicated algorithms provides non-invasive indications of artery stiffness. In some embodiments, dual-wavelength illumination also enables conjunctival vascular mapping for user identification.

In accordance with an embodiment, an integrated microcontroller manages the image sensor settings, data transfers, illumination LED brightness and thermals while monitoring current draws to prevent patient discomfort. The embedded cryptography engine provides end-to-end AES256 data encryption with device access control to secure any sensitive medical videos or registered biometric signatures. Together these tailored optical, sensing and processing elements balance multi-modal visualization capabilities and analysis with compact integration, illumination control, safety precautions, and biometric data protections for advanced point-of-care diagnostics.

In accordance with an embodiment, the otoscope 204 is also referred to herein as a motorized camera module 204 comprising an extension/retraction mechanism, a tilt mechanism, a camera sensor, a camera, a lighting element, and a microcontroller. Broadly, the device incorporates a motorized camera module (204) designed for visual inspection inside bodily cavities. The module may comprise a complementary metal-oxide semiconductor (CMOS) image sensor with 5 megapixel resolution and integrated lens system allowing wide viewing angles up to 120 degrees. In one embodiment, the otoscope module 204 is comprised of a camera sensor with a narrow profile of 8 mm thickness or less to enable insertion into the ear canal or nasal passage and a minimum protrusion of 1 cm from the surface of the external shell of the device to enable effective visualization of the interior of the nasal passage or ear canal while reducing external light distortion and thus ensuring uniform, precise, and repeatable imaging of ear, nose, and mouth/throat cavities. An exemplary otoscope 204 is illustrated in FIG. 27 as integrated with the medical/consumer electronics device 140.

To enable imaging inside difficult to illuminate cavities such as the throat, nose, and ears, the camera module may include an array of light-emitting diodes (LEDs) arranged circumferentially and/or toroidally around the lens. In one embodiment, for example, but not limited to, six miniaturized surface-mount LEDs may feature 7000K color temperature and 80 CRI rating for faithful subject lighting. Custom driver electronics allow LED brightness modulation up to a maximum luminous output of 300 lumens to clearly expose tissue surfaces without discomfort when inserted.

For positioning flexibility, the camera module may couple to a brushed DC micromotor (206) enabling adjustable tilt controlled through the user interface. An integrated Hall sensor provides closed-loop feedback for precision control within +2 degrees during motorized actuation. The adjustments facilitate proper lighting angle exposure and device steadying by users themselves.

The motorized tilting may, in accordance with an embodiment, supplement mechanized linear actuation of the module 204 outward from its housing recess via a geared micromotor coupled to a threaded camera mount translating the rotational motion into a smooth telescoping extension. This automatic motion gently aids users in properly reaching difficult to access cavities without sensor contact while the adjustable lighting maximizes visual clarity once positioned.

An integrated microcontroller may manage individual component control while monitoring current draws and thermals to prevent unintended patient injury as the device actuates. Cryptographic data protection prevents any unauthorized imaging access. Together these motorization strategies simplify and enhance hands-free visualization of bodily areas through optimized, self-directed camera positioning and lighting exposure.

The integrated stethoscope module (206) may enable acoustic capture of internal bodily sounds for cardiopulmonary diagnosis. In one embodiment, it may comprise a digital MEMS microphone with capacitive sensing element fitted behind an acoustically transparent port on the contoured rear surface. An exemplary stethoscope module 206 as integrated into medical/consumer electronics device 140 is illustrated in FIG. 27.

The micropower MEMS transducer may exhibit low self-noise (<26 dBSPL) to resolve faint vessel sounds while handling up to 115 dB SPL prior to overload, enabling auscultation of vascular murmurs. An integrated application-specific integrated circuit (ASIC) performs bandpass filtering from 20 Hz to 1 kHz using a 4th order Butterworth topology to increase signal fidelity in this range by up to 30% SNR while rejecting out-of-band noise. Integrated amplifiers with up to 40 dB gain allow detecting sounds down to 0.5 mPa in amplitude.

To maintain accuracy amid crosstalk, periodic self-calibration system may leverage electrical test signal injection to verify frequency response. The SPU0414's uniform sensitivity spanning 20 Hz to 20 kHz ensures flat measured calibration spectral deviation below 0.2 dB up to 1 kHz after transfer function correction.

The stethoscope's data security provisions may include biopotential analog encryption co-integrated with the sensor ASIC prior to any digitalization to reduce tampering risks. The module intentionally avoids wireless connectivity during use, relying on physical device contact to prevent remote attack vectors while ensuring data privacy.

Together these advances may support discerning auscultatory sound capture across cardiopulmonary structures in compact form even amid size, power, and security constraints through customized analog hardware paired with adaptable digital processing.

In one embodiment, body temperature measurement is enabled through an integrated infrared thermometer (208), also referred to as an IR thermometer 208 herein. The non-contact sensor features a thermoelectric transducer incorporating a specialized absorptive thin film thermopile detector array comprising of over 20 thermocouples. An embedded hermetically sealed precision thermistor provides on-board thermal stabilization to maintain calibration accuracy. In one embodiment, the infrared thermometer 208 is comprised of a thermistor for on-board thermal stabilization, calibration, and compensation; a mirror to focus the infrared radiation onto the detector and help to block unwanted wavelengths; an optical bandpass filter for optimal response convergence and immunity to environmental optical noise; a metallic shield for electromagnetic isolation; and a low-conductance shield for heat isolation and to minimize heat leakage from other areas of the device.

Figure 26:
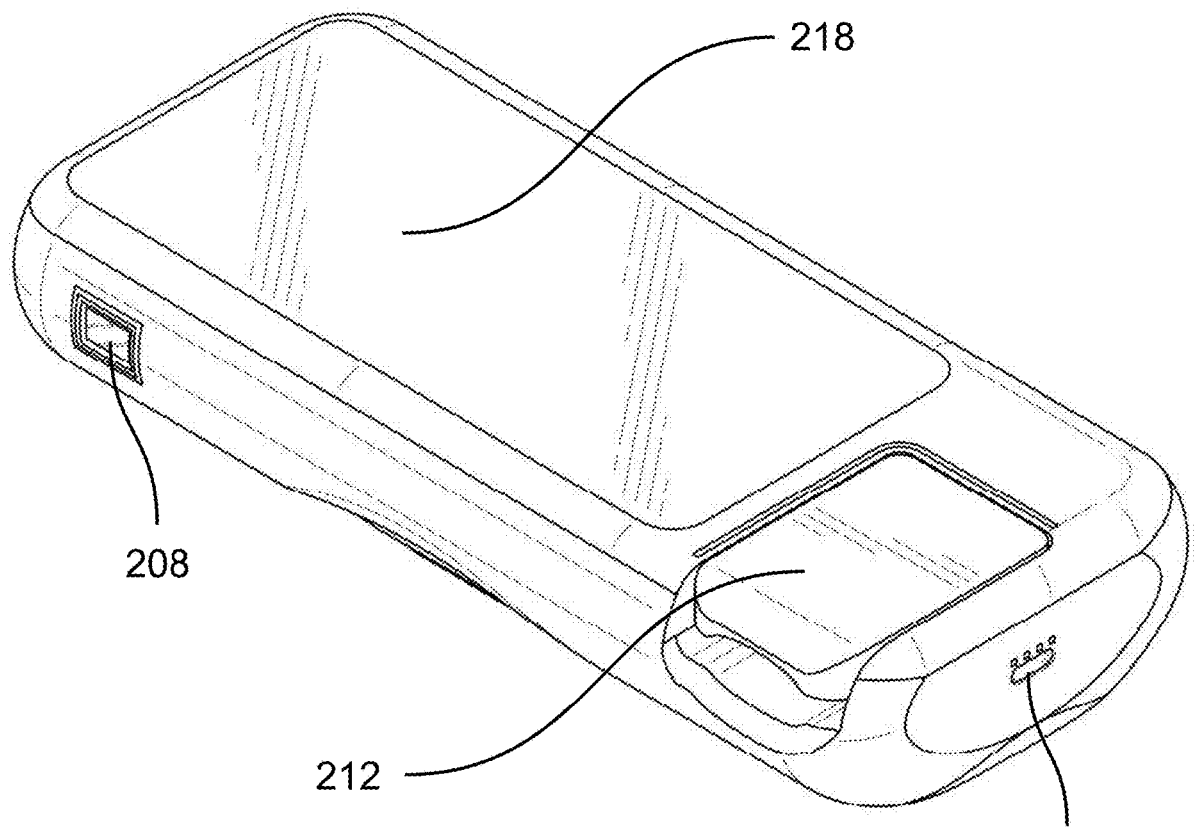
FIG. 26 illustrates an exemplary multi sensor handheld medical diagnostic device.

An exemplary IR thermometer 208 integrated into the medical/consumer electronics device 140 is illustrated in FIG. 26 and FIG. 27.

In one embodiment, the medical-grade sensor calibration targets performance within +0.1° C. across the human body temperature range spanning 35° C. to 42° C. Focused calibration at the elevated range ensures clinical-level accuracy for detecting fevers. Sensitive electronics discern minute temperature differences across the target skin surface. Integrated optical bandpass filtration from 5 μm to 14 μm provides optimal response convergence and immunity to environmental optical noise.

To enable the minimized form factor needed for handheld integration, the infrared sensor (208) and supporting electronics occupy, in accordance with an embodiment of the invention, a compact footprint of 8 mm×5 mm×1.5 mm optimized for low power operation. The miniaturized design exposes a measurement aperture on the device surface while concentrating parametrically heated sinks and thermal mass concentrators to actively regulate internal temperature. Temperature readouts thus remain unaffected by heat from other device modules. In one embodiment, an internal thermistor monitors module temperature drift with compensation to maintain stated accuracy specifications across operating conditions. Firmware safe-mode cutoff prevents fallacious diagnosis from severe measurement distortions such as from rapid motional impacts. An external metallic shield provides full electromagnetic isolation. The precise IR sensor integration, thermal discipline, and footprint reduction provide accurate body temperature quantification in a handheld diagnostic tool with reduced cross-interference.

Electrocardiogram (EKG) capabilities are enabled through an integrated EKG sensor module 210. In one embodiment, the module comprises multiple surface electrodes and supporting electronics customized for simplifying personal use. The module comprises independent stainless-steel skin contact pads (610) forming three bipolar limb lead pairs following Einthoven's triangle configuration using miniature button electrodes securely embedded into the contoured rear surface. These make direct contact with one finger of each hand of the user during device operation. The steel construction and textured shape provide patient comfort while maximizing signal fidelity. An optional right-leg drive loop amplifier with fourth electrode can be activated for enhanced common-mode noise rejection. The contacts points for an exemplary EKG sensor module 210 as integrated into the medical/consumer electronics device 140 is illustrated in FIG. 27.

In one embodiment, the small footprint electrodes couple to a miniaturized instrumentation amplifier integrated circuit (620) optimized for high input impedance (>10 GΩ) and ultra low 2.4 nV/√Hz input noise density enabling resolvable signals down to 10 HV peak-peak for discerning cardiac dynamics. Independent for each channel, programmable gain up to 1000 V/V amplifies signals before 192 Hz anti-aliasing elliptic filtration and 16-bit A/D conversion at 500 Hz spanned a ±300 mV range, allowing R-wave peak capture along with ST segment subtleties.

To counter electromagnetic interference risks from nearby device elements which can cause artifacts, the EKG signal paths may feature multiple stages of dielectric shielding using grounded copper-silicon layers (630). Additionally, driven-right-leg feedback continually suppresses common-mode interference. High fidelity measurements support 1 μV accuracy following AAMI standards.

In one embodiment, on-board biopotential analog encryption accompanying digitization maintains patient data privacy while micro-power gating reduces idle energy expenditure. The integrated solution supports rapid portable multi-lead electrocardiography with robustness against crosstalk.

In one embodiment, the integrated pulse oximeter module (212) enables contactless determination of arterial oxygen saturation and pulse rate leveraging multiwavelength photoplethysmography. The sensor comprises dual emitter light source combining peaks at 660 nm and 905 nm paired with a wide area silicon photodiode detector. An exemplary pulse oximeter sensor 212 is illustrated in FIG. 26 as integrated into the medical/consumer electronics device 140.

In one embodiment, the red and infrared LEDs are time-multiplexed to alternate illumination wavelengths at frequency 200 Hz while maintaining average optical power output below 15 mW to prevent skin heating. The large-area photodetector positioned 12 mm from the source features integrated optical filtration matching the peaks to maximize signal-to-noise ratio. A low noise transimpedance amplifier converts the photocurrent before lock-in demodulation extracts the mixed blood pulsation signals from the photoplethysmogram for oxygen saturation computation.

In one embodiment, surface-mount device components allow miniaturization with the sensor occupying footprint 6 mm×8 mm×1.5 mm flush on the device surface while retaining >90% power efficiency. An integrated microcontroller manages adaptive power delivery synchronized to cardiac pulse for power savings. A firmware methodology helps improve calibrated SpO2 accuracy ranges.

In accordance with an embodiment of the invention, to prevent interference from display elements, the optical stage attaches to a compact faraday cage with feedthrough filters while localized electromagnetic shielding prevents ambient interference. The digital subsystem incorporates encryption to secure patient data through the pulse oximetry analytics. Overall the design balances pulse monitoring performance within size, power and security goals.

The body composition monitor (214) integrates bio-impedance analysis circuitry customized for personal use to characterize body fat percentage and muscle mass distribution. In one embodiment, an array of stainless steel electrode contacts conform to the user's palm for simplified handheld testing. In other embodiments, three contacts are applied to various limb areas of the body to test body fat and muscle tone in those areas. An exemplary body composition monitor 214 as integrated into the medical/consumer electronics device 140 is exemplarily illustrated in FIG. 27.

In one embodiment, a multi-frequency single-chip signal generator outputs excitation currents spanning 5 kHz to 100 kHz at voltage levels between 100 mV to 500 mV. The sequencing synthesizes composite waveforms encoding multiple discrete frequencies enabled by a 16-bit DDS-based architecture with 2.4 mW quiescent power. Instrumentation amplifier analog front-ends ensure 4-wire precision impedance extraction simultaneously for all pathways across both legs and arms.

In one embodiment, selective shields minimize crosstalk between energized electrodes while the steel housing acts as system ground. Precision thin-film resistors establish reference calibration. Frequency-dependent impedance shifts detected by lock-in amplifiers reveal intra to extracellular fluid variations indicating fat to muscle densities. Custom machine learning models implemented on the integrated microprocessor convert multi-frequency impedances to body composition percent readouts.

In one embodiment, to secure processed results, the analog front-end features bioelectric encryption complemented by AES-256 digital encryption with keys exchanged at the start of each measurement routine to maximize data protection. Combined with the tailored low-power bio-impedance stimulus-response analyzer, the technology supports accurate on-demand body metrics.

The integrated glucometer module (226) quantifies blood glucose levels from a small sample introduced via test strip. The test strip port features a compact friction-fit receptacle with integrated ejection technology and intuitive guide rails permitting single-handed test strip loading.

In one embodiment, electrical contacts at the base connect the module to electrodes on strips once inserted. Excitation voltages applied across strip sensor elements elicit currents proportional to sample glucose concentrations per established biosensor electrochemistry. The analog front end conditions response signals before digitization by integrated ADCs. Sensor-specific calibration data stored in non-volatile memory converts readings into accurate glucose level readouts covering 20 to 500 mg/dL.

Careful thermal isolation may maintain 15-32° C. module range for precision enzymatic kinetics while radiofrequency interference filters and a grounded Faraday cage protects the sensor electronics and data. Power-gating and micro-sleep states supported by the integrated microcontroller reduce standby power consumption.

In one embodiment, the hematology analyzer (228) characterizes blood cell morphology and type distribution through multi-wavelength scanning cytometry. The fluidic inlet enables introduction of 10 µL sample volumes into a regulated microfluidic circuit incorporating dilution and cell velocity regulation.

In one embodiment, a 635 nm, 532 nm, and 405 nm flow-through external cavity pulsed laser source excites sample cells serially with matched photomultiplier detection synchronized to the 12 kHz cell rate enabling multi-channel optics density scattering signatures. Integrated digital signal processing classifies erythrocytes, leukocytes subclasses, and thrombocyte counts by established cytometry methodologies.

In one embodiment, surface treatments minimize sample adhesion, current leakage, and corrosion while embedded calibration routines executing during idle durations track and compensate aging drifts from component factors or fluidic residue buildup to maintain accuracy over lifecycle use without user interventions.

The transceiver 216 may send and receive data to a remote server over a network. For example, the transceiver 216 may send a signal indicative of information received from sensors of the medical/consumer electronics device 200 in FIG. 2 over the network 150 in FIG. 1 to the analysis system 120 in FIG. 1. For example, the transceiver 216 may receive a signal indicative of a diagnosis, an urgency level, and/or a recommendation from the analysis system 120 via the network 150. The transceiver 216 may prepare information received from sensors of the medical/consumer electronics device 200 into a format transmissible over a network, such as the network 150 and ultimately consumable by a remote server, such as the analysis system 120. The transceiver 216 may receive information from a network, such as the network 150, and prepare the information in a format consumable by the processor 222. In one embodiment, the wireless transceiver (216) is further configured to intelligently offload computationally intensive tasks to the edge compute node based on latency requirements, bandwidth availability, and the edge node's advertised capabilities, and securely transmit anonymized and encrypted data to the cloud computing platform for deep learning and predictive analytics.

The display 218 may display information captured from sensors of the medical/consumer electronics device 200. The display 218 may display information input via the input 220 such as a patient's information (e.g., name, height, weight, etc.). The display 218 may display information received from a remote server, such as the analysis system 120 in FIG. 1. The display (218) is further configured to present real-time alerts and notifications based on the processed sensor data, and display contextual health insights and recommendations received from the edge compute node and/or the cloud computing platform. An exemplary display 218 is exemplarily illustrated in FIG. 26 as integrated with the medical/consumer electronic device 140.

The input 220 may comprise keyboard (e.g., physical keyboard, virtual keyboard, projection keyboard, etc.), mouse, joystick, etc. The input 220 may be used to enter text, make selections, etc.

The handheld medical device incorporates a highly integrated system-on-chip (SoC) processor (2804) that serves as the central control unit for managing sensor data, user interfaces, power optimizations, and external connectivity. The processor 222 may execute instructions stored in memory 224, such as an application to access the analysis system 120. The SoC processor (2804) may further comprise a heterogeneous multicore architecture with low-power cores for real-time data processing and high-performance cores for running complex analytics and machine learning models, and a hardware-based encryption engine for secure data handling.

The housing of the device further comprises a built-in battery with a power management system for extending the device's operating time.

Onboard Processor Data Management (2806). In one embodiment, the processor (2806 features a heterogeneous multicore architecture that combines low-power ARM Cortex-M cores for real-time processing and data filtering, with higher performance Cortex-A cores for running the operating system, complex analytics, and machine learning inferences.

The processor (2806) is designed to intelligently manage data from the various sensor modules, determining which information to prioritize for user alerts, edge compute offloading, and cloud-based AI processing. This hierarchical data management approach ensures optimal resource utilization, data security, and user experience.

For real-time data alerting, the processor (2806) continuously monitors incoming data streams from the sensors, applying rule-based triggers and heuristic thresholds to identify abnormal readings or patterns that warrant immediate user attention. These alerts are prioritized and displayed on the device's integrated screen (218) with associated recommendations for action. The processor (2806) uses advanced algorithms to minimize false positives while ensuring critical health events are not missed.

In one embodiment, to handle computationally intensive tasks that are still time-sensitive, the processor (2806) selectively offloads data to a nearby edge compute node (190). The processor (2806) intelligently decides which tasks to offload based on latency requirements, bandwidth availability, and the edge node's advertised capabilities discovered through a handshake protocol. Secure communication between the device and the edge node is established using the Wi-Fi 6 (802.11ax) connectivity module (256) with WPA3 encryption. The processor (2806) packages the relevant data with a task manifest before transmitting it to the edge node, and integrates the returned results into the diagnostic outputs.

In one embodiment, for deep insights and predictive analytics, the processor (2806) selectively uploads anonymized and encrypted data to a cloud computing platform, hereinafter also referred to as analysis engine (120) with specialized AI accelerators. The processor (2806) applies privacy-preserving techniques such as differential privacy and federated learning to ensure individual data cannot be reconstructed from the uploaded features. Secure communication with the cloud platform is established over a cellular 5G modem with end-to-end encryption. The processor (2806) schedules the cloud uploads during periods of high bandwidth availability and low device usage to minimize any performance impact.

The cloud platform returns AI-generated insights, which the processor (2806) contextualizes and presents to the user via visualizations on the device display (218) or the companion mobile app on an edge compute platform. These insights enable personalized health recommendations and predictive interventions.

In one embodiment, throughout the data management process, the processor (2806) employs advanced security measures to protect sensitive health information. This includes hardware-based encryption engines, secure boot processes, and isolated execution environments for handling sensitive data. The processor (2806) also manages the device's power consumption using dynamic voltage and frequency scaling (DVFS) techniques, sleep modes, and selective component activation to maximize battery life.

By intelligently coordinating data flows, applying edge and cloud compute resources, and prioritizing data security and user experience, the onboard processor (2806) enables the handheld medical device to deliver comprehensive, real-time diagnostics and long-term health insights in a secure and efficient manner.

The handheld medical diagnostic device features an adaptive power management system that dynamically adjusts power consumption based on the device's usage patterns and sensor requirements. The adaptive power management system may employ various techniques, such as dynamic voltage and frequency scaling (DVFS), selective component activation, and energy harvesting, to optimize power efficiency and extend battery life.

In one embodiment, the SoC processor continuously monitors the usage patterns of the device and the individual sensor modules, analyzing factors such as sensor activation frequency, data processing requirements, and communication bandwidth. Based on this analysis, the adaptive power management system dynamically adjusts the power delivery to each sensor module, ensuring that power is allocated efficiently based on the specific requirements of each sensor.

The adaptive power management system may also utilize machine learning algorithms to predict future power requirements based on historical usage patterns and sensor data. By proactively adjusting power management settings based on these predictions, the system can further optimize battery life and ensure that the device is always available when needed.

In addition to managing power consumption, the adaptive power management system may also incorporate energy harvesting techniques to supplement battery power. This can include harvesting energy from user motion, such as walking or running, using kinetic energy harvesters, or collecting ambient light energy using miniaturized solar cells. By leveraging these additional energy sources, the adaptive power management system can further extend the device's operating time and reduce the frequency of battery recharging.

In one embodiment, the handheld medical diagnostic device incorporates a multi-modal biometric security system 2808 for user authentication and data access control. The biometric security system 2808 may comprise vascular pattern detection and/or biometric detection on a connected edge compute node such as face detection on a cell phone.

Figure 28:
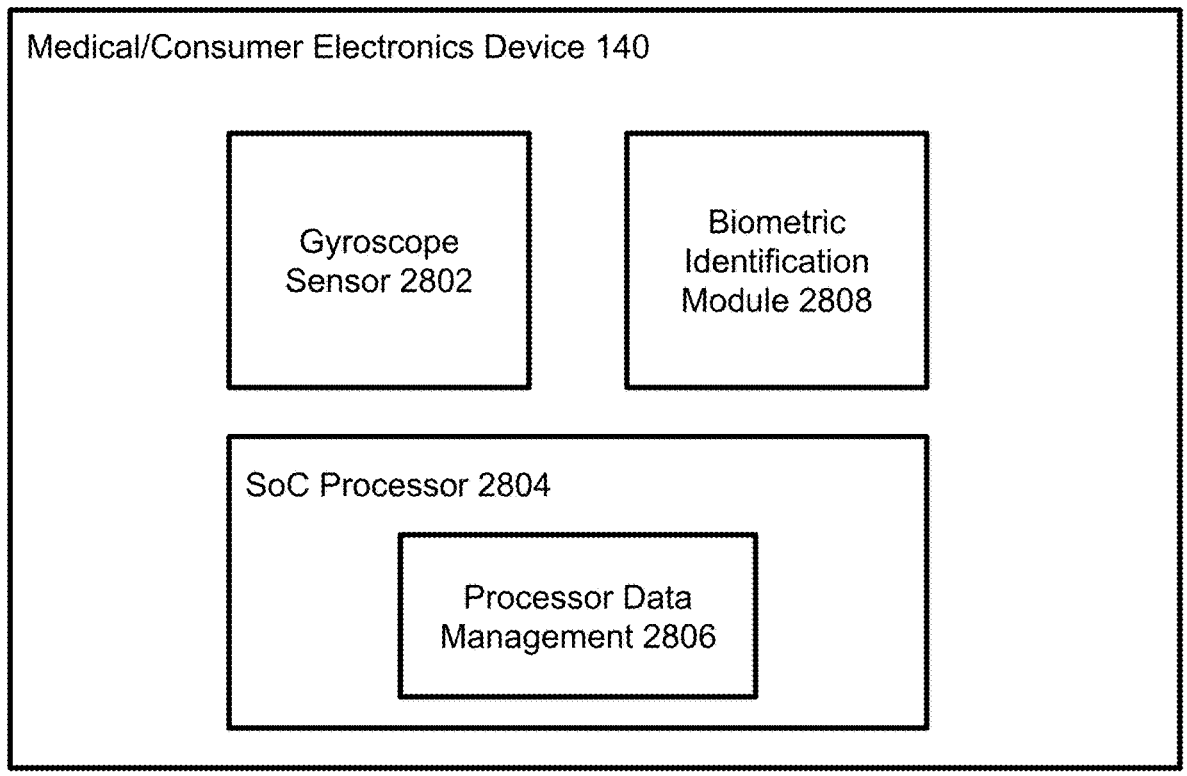
FIG. 28 illustrates an exemplary system for the AI enabled multisensor connected telehealth system

FIGS. 27 and 28 illustrate an exemplary embodiment of the medical/consumer electronics device 140. The various sensors or sensor contact points may be laid out as illustrated housed in a housing. In one embodiment, the housing of the medical/consumer electronics device 140 may be curved at the bottom and middle surface for hand-held use and self-administration of tests by a user.

Figure 3:
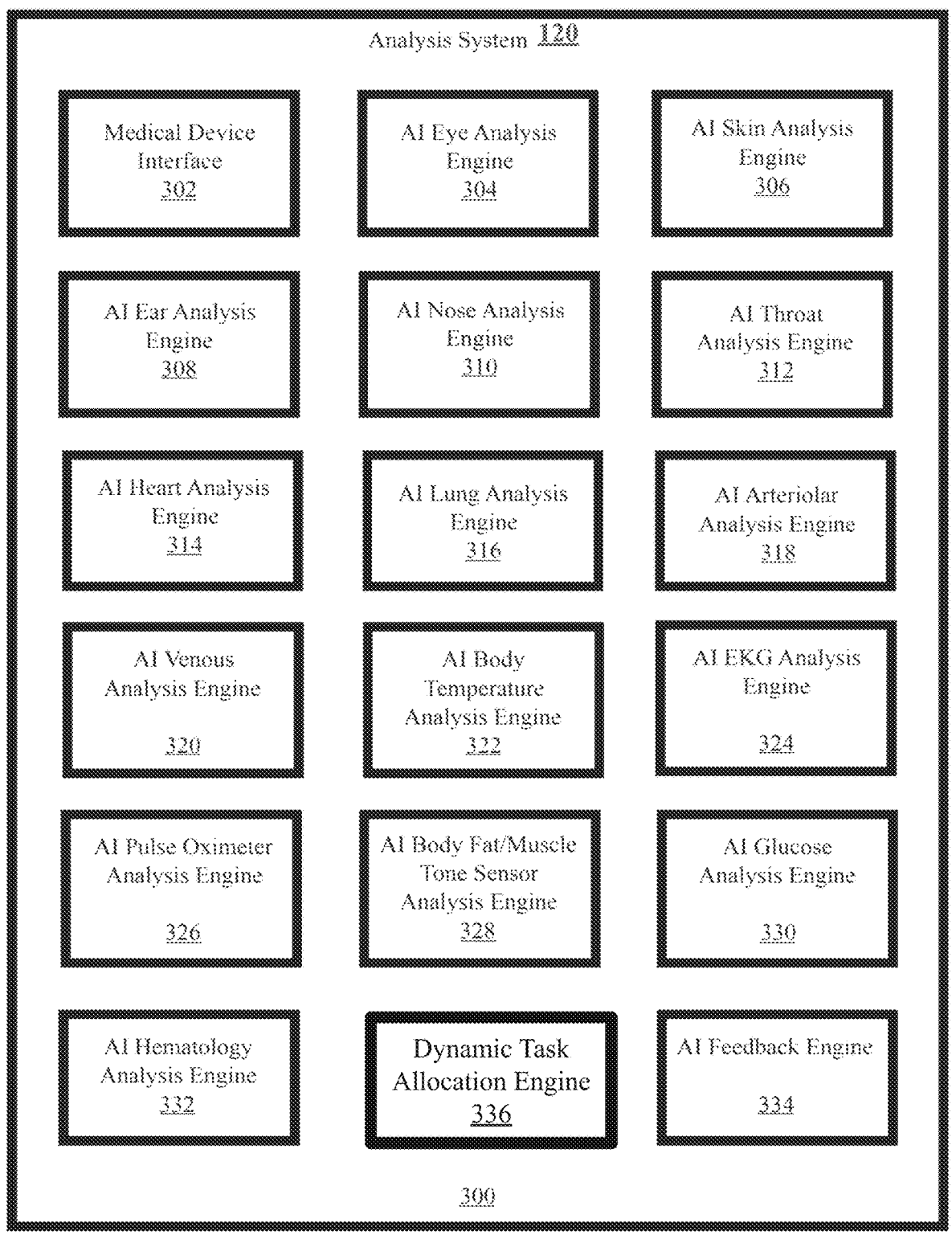
FIG. 3 illustrates an example telemedicine platform in accordance with an exemplary embodiment of the invention.

Referring now to FIG. 3, the handheld medical/consumer electronics device 140 is further comprised of a dynamic task allocation engine 336 that distributes AI processing tasks across the on-device, edge, and cloud layers of the system architecture. In other words, the dynamic task allocation engine 336 optimizes the utilization of computational resources and ensures efficient, real-time, and secure processing of sensor data and AI algorithms.

At a high level, the dynamic task allocation engine 336 takes into account various factors such as the specific sensors active on the medical/consumer electronics device 140, the computational complexity of the associated AI analysis engines 2204-2220, data privacy requirements, and network conditions. By considering these factors, the dynamic task allocation engine 336 determines the optimal distribution of AI processing tasks across the on-device, edge, and cloud layers, ensuring a balance between real-time performance, data security, and overall system efficiency.

The dynamic task allocation engine 336 operates through a series of steps to dynamically allocate AI processing tasks. First, it identifies the active sensors on the medical/consumer electronics device 140, such as the high-magnification camera 202, motorized camera 204, stethoscope 206, IR thermometer 208, EKG 210, pulse oximeter 212, body fat/muscle tone sensor 214, glucometer 226, and hematology analyzer 228, and gyroscope sensors 232. Next, it assesses the computational requirements for preprocessing the raw sensor data, assigning simple tasks like signal filtering and feature extraction to the on-device layer to minimize latency and data transmission overhead.

The dynamic task allocation engine 336 then evaluates the computational complexity and data privacy requirements of each AI analysis engine 304-332 associated with the active sensors. It assigns real-time, low-complexity tasks to the on-device layer, moderate-complexity tasks with less stringent real-time requirements to the edge layer, and high-complexity tasks with long-term data analysis needs to the cloud layer. The engine 336 continuously monitors network conditions and dynamically reassigns tasks to ensure uninterrupted processing in case of network deterioration.

In one embodiment, data privacy and security are weighted more heavily in the task allocation process. The engine 336 applies appropriate data anonymization, encryption, and secure communication protocols based on the sensitivity of the sensor data and the assigned AI engine. It ensures that sensitive data, such as EKG and glucometer readings, receive higher levels of protection compared to less sensitive data from sensors like the IR thermometer or body fat/muscle tone sensor.

The dynamic task allocation engine 336 manages the execution of the assigned tasks across the three layers, ensuring proper coordination and data flow between them. The AI feedback engine 334 collects results from the various AI analysis engines and generates comprehensive diagnostic insights, which are then transmitted back to the medical/consumer electronics device 140 for display and user interaction. The dynamic task allocation engine 336 continuously monitors the system's performance and adapts the task allocation based on changes in computational requirements, network conditions, and user preferences, ensuring optimal resource utilization and maintaining a balance between real-time performance, data privacy, and overall system efficiency.

Alternative systems or processes for task allocation in a distributed AI architecture could include static allocation, where tasks are assigned to specific layers based on predefined rules or thresholds. However, this approach lacks the flexibility and adaptability of the dynamic task allocation engine 336 proposed in the present invention. Another alternative could involve a centralized task allocation system, where a single entity, such as a cloud server, makes all the allocation decisions. While this might simplify the decision-making process, it introduces a single point of failure and may not be as responsive to local device conditions or network fluctuations.

By considering factors such as sensor activity, computational complexity, data privacy, and network conditions, the engine 230 optimizes resource utilization and ensures efficient, real-time, and secure processing of sensor data and AI algorithms. This innovative approach sets the present invention apart from alternative systems and processes, providing a flexible, adaptable, and robust solution for integrating AI capabilities into handheld medical devices.

Analysis System

FIG. 3 illustrates an example analysis system 300 in accordance with an exemplary embodiment of the invention. The example analysis system 300 may receive a signal from a medical/consumer electronics device, such as the medical/consumer electronics device 140 in FIG. 1, and/or an edge compute node 190 in FIG. 1 via a network, such as the network 150 in FIG. 1, wherein the signal comprises information from sensors of the medical/consumer electronics device. The example analysis system 300 may use information from sensors of the medical/consumer electronics device to determine a diagnosis, an urgency level, and/or a recommendation. The example analysis system 300 may transmit a signal comprising the determined diagnosis, urgency level, and/or recommendation via the network, such as the network 150, to the medical/consumer electronics device, such as the medical/consumer electronics device 140. The example analysis system 300 may be the same or similar to the analysis system 120 in FIG. 1. The example analysis system 300 comprises one or more artificial intelligence (AI) modules. The AI modules may use training data to create a model for determining outputs (e.g., diagnoses, urgency levels, recommendations, etc.) for specific inputs. The AI modules may update models based on feedback from responses, creating a feedback loop that continually improves future results based on past results. The example analysis system 300 comprises a medical/consumer electronics device interface 302, an AI eye analysis engine 304, an AI skin analysis engine 306, an AI car analysis engine 308, an AI nose analysis engine 310, an AI throat analysis engine 312, an AI heart analysis engine 314, an AI lung analysis engine 316, an AI arteriolar analysis engine 318, an AI venous analysis engine 320, an AI body temperature analysis engine 322, an AI electrocardiogram (EKG) analysis engine 324, an AI pulse oximeter analysis engine 326, an AI body fat and/or muscle tone sensor analysis engine 328, an AI glucose analysis engine 330, an AI hematology analysis engine 332, and an AI feedback engine 334. Other systems and databases may be used, as would be readily understood by a person of ordinary skill in the art, without departing from the scope of the invention.

Figure 22:
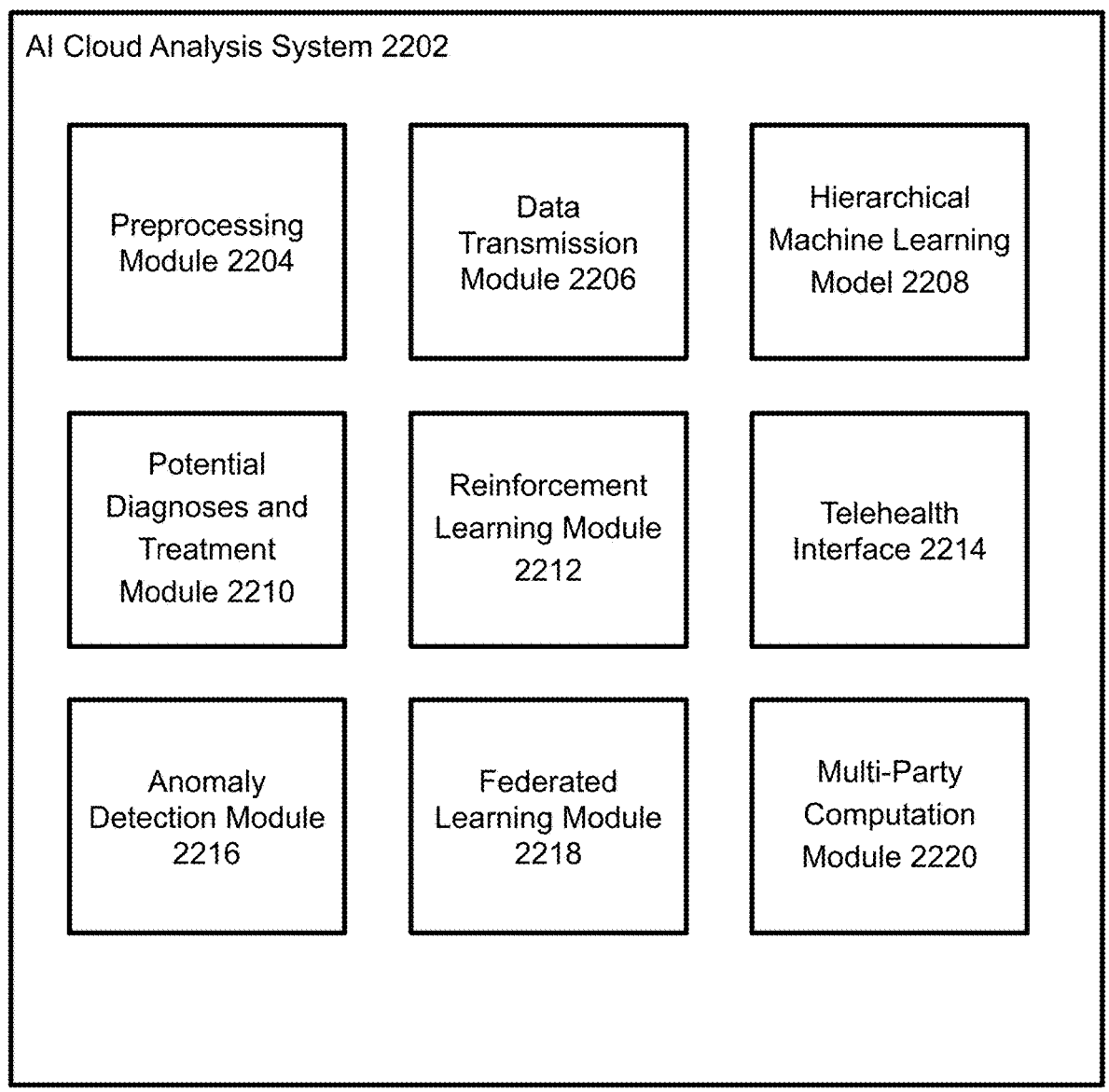
FIG. 22 illustrates an exemplary system for the AI enabled multisensor connected telehealth system.

FIG. 22 broadly illustrates the AI cloud analysis system 2202 is a scalable, distributed computing platform that leverages advanced artificial intelligence (AI) and machine learning (ML) techniques to process and analyze data generated by the handheld medical device. The system comprises one or more AI modules that work together to provide accurate diagnoses, determine urgency levels, and offer personalized recommendations based on the input data. In one embodiment, the AI cloud analysis system 2202 is embodied within the analysis system 120 or may be a standalone system that is connected to the network 150.

In one embodiment, the system 2202 comprises a suite of specialized AI analysis engines, each designed to process and interpret data from specific sensors or groups of sensors. These engines include the AI eye analysis engine 304, AI skin analysis engine 306, AI car analysis engine 308, AI nose analysis engine 310, AI throat analysis engine 312, AI heart analysis engine 314, AI lung analysis engine 316, AI arteriolar analysis engine 318, AI venous analysis engine 320, AI body temperature analysis engine 322, AI electrocardiogram (EKG) analysis engine 324, AI pulse oximeter analysis engine 326, AI body fat and/or muscle tone sensor analysis engine 328, AI glucose analysis engine 330, and AI hematology analysis engine 332.

At a high level, the AI cloud analysis system 2202 receives preprocessed sensor data from the medical/consumer electronics device 140 via the medical/consumer electronics device interface 302. The interface 302 ensures secure and efficient data transmission between the device 200 and the cloud system 300. Once the data is received, the AI cloud analysis system 2202 routes it to the appropriate AI analysis engines based on the type of sensor and the specific analysis required. Each AI engine applies advanced machine learning algorithms, such as deep learning neural networks, to extract meaningful insights and patterns from the sensor data. These insights are then combined and interpreted by the AI feedback engine 334, which generates comprehensive diagnostic results and personalized health recommendations. In one embodiment, the AI cloud analysis system 2202 receives provider feedback from a provider device, wherein the feedback is received by checkbox method such that a provider checking and/or unchecking diagnoses as appropriate, which is received by the AI cloud analysis system 2202 to contribute to additional learning by the AI system 2202.

The AI cloud analysis system 2202 works in close collaboration with the dynamic task allocation engine 336 to optimize the distribution of AI processing tasks across the on-device, edge, and cloud layers. The dynamic task allocation engine 336 continuously assesses the computational requirements and data privacy needs of each AI analysis engine, as well as the current network conditions and device capabilities. Based on this assessment, the dynamic task allocation engine 336 determines which AI engines should be executed in the cloud layer and communicates this decision to the AI cloud analysis system 2202 via the medical/consumer electronics device interface 302. The AI cloud analysis system 2202 then activates the necessary AI engines and allocates the required computational resources to process the incoming sensor data.

As illustrated in FIG. 22, the AI cloud analysis system 2202 is comprised of a preprocessing module 2204, data transmission module 2206, hierarchical machine learning model 2208, potential diagnoses and treatment module 2210, reinforcement learning module 2212, telehealth module 2214, anomaly detection module 2216, federated learning module 2218, and a multi-party computation module 2220.

At a high level, the preprocessing module 2204 is responsible for processing the raw sensor data collected by the multi-sensor medical device and extracting relevant features that can be used for further analysis and decision-making. This module may employ various signal processing and machine learning techniques to clean, transform, and analyze the data, with the goal of improving the accuracy and efficiency of the downstream tasks.

In one embodiment, the preprocessing module 2204 is implemented as a software library or a set of algorithms that run on the microcontroller or SoC of the multi-sensor medical device. The module first applies signal conditioning techniques, such as filtering, amplification, and analog-to-digital conversion, to improve the signal-to-noise ratio and prepare the data for digital processing. Then, it employs time-domain, frequency-domain, and time-frequency domain analysis methods, such as Fourier transform, wavelet transform, and short-time Fourier transform, to extract temporal and spectral features from the data. Additionally, the module may use statistical methods, such as principal component analysis (PCA) and independent component analysis (ICA), to reduce the dimensionality of the data and identify the most informative features.

Alternatively, a hybrid approach may be used, where some of the preprocessing and feature extraction tasks are performed on the edge device (i.e., the multi-sensor medical device), while others are offloaded to the cloud platform, depending on the complexity and real-time requirements of the tasks.

At a high level, the data transmission module 2206 is responsible for encrypting the preprocessed patient data and transmitting it securely from the multi-sensor medical device to the cloud computing platform. This component improves confidentiality, integrity, and privacy of the patient data during transmission, protecting it from unauthorized access, tampering, or eavesdropping.

In one embodiment, the data transmission module 2206 employs a hybrid encryption scheme that combines symmetric and asymmetric encryption techniques. For real-time data transmission, a lightweight symmetric encryption algorithm, such as Advanced Encryption Standard (AES) or ChaCha20, is used to encrypt the data using a shared secret key. The secret key is securely exchanged between the multi-sensor medical device and the cloud computing platform using a quantum key distribution (QKD) protocol, which leverages the principles of quantum mechanics to establish a secure communication channel. For privacy-preserving computation on the encrypted data, a homomorphic encryption scheme, such as Paillier cryptosystem or fully homomorphic encryption (FHE), is used to allow the cloud platform to perform computations on the encrypted data without decrypting it.

Alternatively, the secure data transmission can be implemented using a blockchain-based approach, where the patient data is stored on a distributed ledger and accessed through smart contracts. The blockchain provides a tamper-proof and transparent record of all data transactions, ensuring the integrity and auditability of the data. Another alternative is to use a secure multi-party computation (MPC) protocol, which allows multiple parties (e.g., the patient, the healthcare provider, and the cloud platform) to jointly compute a function over their private inputs, without revealing the inputs to each other. This approach can enable privacy-preserving data aggregation and analysis across multiple data sources.

In one embodiment, the data transmission module 2206 is further comprised of a secure data storage system, which is enabled to store both raw data and data processed by device AI/edge AI/cloud AI modules. Additionally, the secure data storage system may store other uploaded records by the provider via mobile device and/or computer, and/or other uploaded records by the patient/user via the device and/or another mobile device or computer, (which also serves as a patient-centered health record).

At a high level, the hierarchical machine learning model 2208 is responsible for processing the encrypted patient data received from the cloud computing platform and generating personalized diagnoses and treatment recommendations. The model may leverage advanced machine learning techniques, such as deep learning and transfer learning, to learn hierarchical representations of the patient data and capture the complex relationships between different variables and outcomes.

In other embodiments the data transmission module 2206 is responsible for protecting the privacy and confidentiality of the patient data during the analysis and sharing process, by adding carefully calibrated noise or randomness to the data or the model outputs. The mechanism ensures that the presence or absence of any individual patient in the dataset cannot be inferred with high confidence, while still allowing the overall patterns and insights to be learned and utilized.

In one embodiment, the differential privacy mechanism is implemented as a mathematical framework, using formal privacy definitions and guarantees, such as $\varepsilon$-differential privacy or $(\varepsilon, \delta)$-differential privacy. The framework defines a privacy budget, which quantifies the amount of noise or randomness that needs to be added to the data or the model outputs, based on the desired level of privacy protection and the sensitivity of the queries or the analyses. The noise is typically drawn from a Laplace or a Gaussian distribution, and is added to the raw data, the intermediate results, or the final outputs, depending on the specific algorithm or the application.

Alternatively, the differential privacy mechanism can be implemented as a machine learning-based approach, using adversarial training or generative models to learn privacy-preserving representations of the patient data. In this case, the mechanism trains a discriminator network to distinguish between the real and the synthetic data, while simultaneously training a generator network to produce realistic and diverse samples that can fool the discriminator. The resulting generator can be used to create privacy-preserving synthetic data, which can be shared and analyzed without revealing the original patient data. Another alternative is to use a hybrid approach, combining differential privacy with other security and cryptographic techniques, such as secure hardware enclaves or homomorphic encryption, to provide a multi-layered protection of the patient data. This approach can enable more secure and trustworthy data sharing and analysis, addressing the various privacy and security risks and challenges in the healthcare domain.

In one embodiment, the hierarchical machine learning model 2208 comprises multiple layers of neural networks, each designed to process a specific type of data or perform a specific task. At the lowest level, a convolutional neural network (CNN) is used to extract spatial features from image and video data, such as X-rays, CT scans, or ultrasound images. At the intermediate level, a recurrent neural network (RNN), such as long short-term memory (LSTM) or gated recurrent unit (GRU), is used to model the temporal dependencies in time-series data, such as ECG, EEG, or vital signs. At the highest level, a graph convolutional network (GCN) is used to integrate multimodal data from different sources, such as electronic health records (EHRs), laboratory tests, and patient-reported outcomes, and learn a unified representation of the patient's health status.

Alternatively, the hierarchical machine learning model can be implemented using other architectures, such as autoencoders, generative adversarial networks (GANs), or reinforcement learning models. These architectures can be used to learn unsupervised representations of the patient data, generate synthetic data for data augmentation, or optimize treatment policies based on patient feedback and outcomes. Another alternative is to use a federated learning approach, where the model is trained collaboratively by multiple healthcare organizations, without sharing the raw patient data. This approach can enable more robust and generalizable models, while preserving the privacy and security of the patient data.

At a high level, the diagnoses and treatment module 2210 generates recommendations based on the analysis of the patient data and the learned patterns and relationships. These recommendations are tailored to the specific characteristics, preferences, and goals of each patient, taking into account their medical history, lifestyle factors, and social determinants of health.

In one embodiment, the diagnoses and treatment module 2210 is embodied in a computing cluster configured to analyze the preprocessed patient information using an ensemble of deep learning models, each model being trained on a specific type of telehealth data and fine-tuned using transfer learning and domain adaptation techniques, the ensemble of deep learning models comprising a modular, extensible architecture and a multi-modal attention fusion module. The computing cluster generates a ranked list of potential diagnoses and a likelihood score for each potential diagnosis using the ensemble of deep learning models.

In one embodiment, the recommendations of the diagnoses and treatment module 2210 are presented to the healthcare provider through an interactive dashboard or a clinical decision support system (CDSS). The dashboard displays the most likely diagnoses, along with their confidence scores and supporting evidence, such as relevant clinical features, risk factors, and similar cases. The dashboard also suggests potential treatment options, including medications, procedures, and lifestyle modifications, based on the patient's profile and the latest clinical guidelines and research evidence.

Alternatively, the personalized diagnoses and treatment recommendations can be delivered directly to the patient through a mobile app or a web portal. In this case, the recommendations are presented in a more consumer-friendly format, using simple language, visual aids, and engaging content. The app or portal can also provide educational resources, self-management tools, and remote monitoring capabilities, empowering the patient to take a more active role in their own care. Another alternative is to integrate the recommendations into the workflow of other healthcare systems, such as EHRs, pharmacy systems, or care management platforms, to enable seamless and coordinated care delivery across different settings and providers.

At a high level, the reinforcement learning module 2212 is responsible for adapting the personalized diagnoses and treatment recommendations based on the feedback and outcomes of the patients and the providers. The module employs reinforcement learning algorithms, such as Q-learning or policy gradients, to learn optimal treatment policies that maximize the long-term health outcomes and satisfaction of the patients, while minimizing the costs and risks.

In one embodiment, the reinforcement learning module 2212 is implemented as a separate component of the cloud computing platform, which interacts with the hierarchical machine learning model and the interactive user interface. The module receives the patient data, the generated recommendations, and the feedback from the patients and the providers as inputs, and uses them to update the parameters and hyperparameters of the machine learning model. The feedback can be explicit, such as ratings, comments, or surveys, or implicit, such as adherence, side effects, or clinical outcomes. The module also employs exploration-exploitation techniques, such as epsilon-greedy or upper confidence bound (UCB), to balance the trade-off between trying new treatment options and exploiting the current best options.

Alternatively, the reinforcement learning module can be integrated into the hierarchical machine learning model, using end-to-end learning approaches, such as deep Q-networks (DQNs) or actor-critic methods. In this case, the model learns to generate personalized recommendations directly from the patient data, without the need for a separate feedback loop. Another alternative is to use a multi-agent reinforcement learning approach, where multiple agents, representing different healthcare providers or stakeholders, collaborate or compete to optimize the treatment policies based on their own objectives and constraints. This approach can enable more realistic and adaptive learning, taking into account the complex dynamics and interactions of the healthcare system.

At a high level, the telehealth interface 2214 is responsible for capturing the input and evaluation of the healthcare providers regarding the personalized diagnoses and treatment recommendations generated by the system. The feedback may include various types of information, such as ratings, comments, suggestions, or corrections, which can be used to improve the accuracy, relevance, and usability of the recommendations.

In one embodiment, the provider feedback is collected through the telehealth interface 2214 using structured or unstructured input fields, such as forms, surveys, or free-text boxes. The interface prompts the provider to review each recommendation and provide their assessment, based on their clinical judgment, experience, and knowledge. The feedback is then processed by the reinforcement learning module, which uses natural language processing and sentiment analysis techniques to extract the relevant information and update the machine learning model accordingly.

Alternatively, the provider feedback can be collected through other channels, such as voice or video recordings, which can capture more nuanced and contextual information. In this case, the feedback is transcribed and analyzed using advanced speech recognition and computer vision techniques, such as deep learning-based models for emotion recognition and facial expression analysis. Another alternative is to use a peer review or a consensus-based approach, where multiple providers collaborate to evaluate and validate the recommendations, using a shared platform or a blockchain-based system. This approach can enable more reliable and unbiased feedback, reducing the potential for individual biases or errors.

At a high level, the anomaly detection module 2216 is responsible for identifying and alerting the healthcare providers about any unusual or unexpected patterns in the patient data, which may indicate potential health issues or risks. The module may employs a combination of rule-based and machine learning-based techniques to detect anomalies, adapting to the specific characteristics and variability of each patient's data.

In one embodiment, the anomaly detection module 2216 is implemented as a real-time monitoring and alerting system, which continuously analyzes the streaming data from the multi-sensor medical device and the cloud computing platform. The module first applies a set of predefined rules and thresholds, based on clinical guidelines and expert knowledge, to identify any values or trends that fall outside the normal ranges. Then, it uses unsupervised machine learning algorithms, such as clustering, density estimation, or autoencoders, to learn the underlying patterns and distributions of the data, and detect any deviations or outliers. The module also employs incremental learning techniques, such as online learning or transfer learning, to adapt to the changing dynamics and contexts of the patient's health status.

Alternatively, the hybrid anomaly detection module can be implemented as a batch processing system, which analyzes the historical data of the patient at regular intervals, such as daily or weekly. In this case, the module uses more complex and computationally intensive algorithms, such as deep learning-based anomaly detection or time-series forecasting, to identify any long-term patterns or trends that may indicate a potential health problem. Another alternative is to use a multi-modal anomaly detection approach, which integrates data from multiple sources, such as wearables, environmental sensors, or social media, to provide a more comprehensive and contextual view of the patient's health. This approach can enable more accurate and timely detection of anomalies, taking into account the various factors and influences that may affect the patient's well-being.

In one embodiment, the alerts and explanations are generated by the hybrid anomaly detection module and delivered through the interactive user interface. The alerts are displayed as prominent visual cues, such as pop-up messages, color-coded icons, or flashing indicators, which convey the severity and urgency of the anomalies. The explanations are presented as concise and informative summaries, using natural language generation and data visualization techniques, which highlight a plurality of findings and recommendations. The users can interact with the alerts and explanations, using various actions, such as acknowledging, dismissing, or investigating the issues, depending on their roles and responsibilities.

Alternatively, the alerts and explanations can be delivered through other channels, such as mobile notifications, email, or voice assistants, which can reach the users in a more timely and convenient manner. In this case, the alerts and explanations are personalized and adapted to the user's preferences and contexts, using machine learning-based recommendation systems or user profiling techniques. Another alternative is to use a conversational interface, such as a chatbot or a virtual agent, which can engage the users in a more natural and interactive dialogue, answering their questions, providing guidance, and gathering feedback. This approach can enable more effective and empathetic communication, building trust and rapport between the users and the system.

At a high level, the federated learning module 2218 is responsible for enabling the collaborative and decentralized training of the machine learning models across multiple healthcare organizations or institutions, without sharing the raw patient data. The framework allows each organization to train the models locally on their own data, and then share only the model updates or parameters with a central server or a peer-to-peer network, which aggregates and optimizes the models globally.

In one embodiment, the federated learning module is implemented as a secure and privacy-preserving protocol, using cryptographic techniques including, but not limited to homomorphic encryption or secure multi-party computation. The protocol ensures that the model updates are encrypted and anonymized before being shared, and that the central server or the peer-to-peer network cannot infer any sensitive information about the individual patients or the organizations. The framework also employs various optimization techniques, such as gradient compression, model quantization, or asynchronous updating, to reduce the communication and computation overhead of the federated learning process.

Alternatively, the federated learning framework can be implemented as a blockchain-based system, using smart contracts and consensus mechanisms to coordinate the model training and sharing among the participating organizations. In this case, the model updates are stored and verified on a distributed ledger, which provides a tamper-proof and auditable record of the learning process. Another alternative is to use a hybrid approach, combining federated learning with other privacy-enhancing techniques, such as differential privacy or data synthesis, to further protect the patient data and the model integrity. This approach can enable more flexible and robust learning, adapting to the different privacy and security requirements of the healthcare organizations.

At a high level, the multi-party computation module 2220 is responsible for enabling multiple parties, such as healthcare providers, researchers, and/or patients, to jointly compute a function or a model on their private data, without revealing the data to each other. The protocol allows the parties to perform various operations, such as aggregation, comparison, or machine learning, on the encrypted or secret-shared data, while ensuring that the results are correct and the privacy is preserved.

In one embodiment, the multi-party computation module 2220 employs a protocol that is implemented as a cryptographic protocol, using secret sharing or garbled circuits techniques. The protocol first divides the private data of each party into multiple shares or fragments, which are then distributed among the other parties. The parties then perform the desired computation on the shares, using a predefined set of rules and algorithms, which ensure that the intermediate results are also secret-shared and do not reveal any information about the original data. Finally, the parties combine the computed shares to obtain the final result, which can be decrypted or reconstructed only by the authorized parties.

Alternatively, the multi-party computation module 2220 can be implemented as a hardware-based approach, using trusted execution environments or secure enclaves, such as Intel SGX or ARM TrustZone. In this case, the private data and the computation are performed inside a secure and isolated environment, which is protected from unauthorized access or tampering by the hardware and the software. The parties can attest to the integrity and the confidentiality of the computation, using cryptographic signatures or certificates, and can verify the results using secure channels or zero-knowledge proofs. Another alternative is to use a hybrid approach, combining secure multi-party computation with other privacy-preserving techniques, such as homomorphic encryption or differential privacy, to provide a more comprehensive and flexible solution. This approach can enable more complex and scalable computations, such as federated learning or secure data analysis, while still maintaining the privacy and the security of the patient data.

In one embodiment, the multi-party computation module 2220 is comprised of a an interactive telehealth module configured to communicate with a provider device by sending a ranked list of potential diagnoses, the likelihood scores, and a visualization of the factors contributing to each diagnosis to the provider device, the visualization comprising an attention mechanism that highlights a predefined set of salient features for each diagnosis. The telehealth module configured to receive feedback from the provider device indicating an appropriateness of the potential diagnoses and any additional insights, the feedback being received using a natural language processing module that extracts structured feedback from free-text notes and/or voice commands and/or touch/trackpad/mouse inputs. The multi-party computation module 2220 further comprising an interactive telehealth portal configured to allow a provider device to communicate with the cloud, device AI/edge AI/cloud AI, patient/user's device, and any other data source connected to the system, and vice versa, also displaying data of various forms on a dashboard, dashboard data including but not limited to (as applicable) a live voice and/or video (or both) call, a patient chart, raw live sensor data, pre-recorded sensor data, text/voice/AI-transcribed subjective statements of the user/patient, prior health records, and the above-referenced telehealth module visualization enabling feedback and continuous training.

Referring now to FIG. 3, the medical/consumer electronics device interface 302 may prepare information intended for a medical/consumer electronics device, such as the medical/consumer electronics device 140 in FIG. 1, into a format transmissible over a network, such as the network 150 in FIG. 1, and ultimately consumable by the medical/consumer electronics device. The medical/consumer electronics device interface 302 may receive information from a network, such as the network 150, and prepare the information in a format consumable by the example analysis system 300.

The AI eye analysis engine 304 may use computer vision to interpret images and/or video of an eye taken by a camera, such as the high-magnification camera 202 in FIG. 2. The AI eye analysis engine 304 may identify a possibility of one or more of conjunctivitis, iritis, subconjunctival hemorrhage, scleral lesions, jaundice (icterus), liver drainage problems, bile drainage problems, hepatitis, gallbladder attacks, bile blockage from gallstones, cancer of the pancreas, cancer of the bile ducts, stye (chalazion), allergies, etc. The AI eye analysis engine 304 may determine conjunctival vessel velocity by examining multiple time stamped eye images or eye video. The AI eye analysis engine 304 may determine a blood pressure based on the determined conjunctival vessel velocity. The AI eye analysis engine 304 may determine an identity by matching conjunctival vessel patterns (including, for example, Conjunctival vessel blood velocity), which could include the spaces in between conjunctival vessels). The AI eye analysis engine 304 may use AI to determine a state or condition. The AI eye analysis engine 304 may use AI to determine a range of possible states or conditions. The AI eye analysis engine 304 may associate a probability with each determined state or condition. Exemplary processing employed by the AI eye analysis engine 304 may be found below in association with FIG. 10 and the corresponding description.

The AI skin analysis engine 306 may use computer vision to interpret images and/or video of skin taken by a camera, such as the high-magnification camera 202 in FIG. 2. The AI skin analysis engine 306 may identify a possibility of one or more of rashes, hives, poison ivy, shingles, tumors, melanoma, bruises, petechiac, leg or other edema, ulcers, bed sores, etc. The AI skin analysis engine 306 may use AI to determine a state or condition. The AI skin analysis engine 306 may use AI to determine a range of possible states or conditions. The AI skin analysis engine 306 may associate a probability with each determined state or condition.

The AI car analysis engine 308 may use computer vision to interpret images and/or video of an car taken by a camera, such as the motorized camera 204 in FIG. 2. The AI car analysis engine 308 may identify a possibility of one or more of neoplasia, perforation, tympanosclerosis, middle car effusion, retracted cardrum, haemotympanum, etc. The AI car analysis engine 308 may use AI to determine a state or condition. The AI car analysis engine 308 may use AI to determine a range of possible states or conditions. The AI car analysis engine 308 may associate a probability with each determined state or condition.

The AI nose analysis engine 310 may use computer vision to interpret images and/or video of a nose taken by a camera, such as the motorized camera 204 in FIG. 2. The AI nose analysis engine 310 may identify a possibility of one or more of obstruction, sinusitis, rhinitis, polyps, adenoids, cancer, etc. The AI nose analysis engine 310 may use AI to determine a state or condition. The AI nose analysis engine 310 may use AI to determine a range of possible states or conditions. The AI nose analysis engine 310 may associate a probability with each determined state or condition.

The AI throat analysis engine 312 may use computer vision to interpret images and/or video of a throat taken by a camera, such as the motorized camera 204 in FIG. 2. The AI throat analysis engine 312 may identify a possibility of one or more of viral infection, bacterial infection, gastroesophageal reflux disease (GERD), tonsillitis, cancer, etc. The AI throat analysis engine 312 may use AI to determine a state or condition. The AI throat analysis engine 312 may use AI to determine a range of possible states or conditions. The AI throat analysis engine 312 may associate a probability with each determined state or condition.

The AI heart analysis engine 314 may interpret audio of a heart taken by a sensor, such as the stethoscope 206 in FIG. 2. The AI heart analysis engine 314 may identify a possibility of one or more of heart murmurs, irregular heart rhythms, etc. The AI heart analysis engine 314 may use AI to determine a state or condition. The AI heart analysis engine 314 may use AI to determine a range of possible states or conditions. The AI heart analysis engine 314 may associate a probability with each determined state or condition.

The AI lung analysis engine 316 may interpret audio of a lung taken by a sensor, such as the stethoscope 206 in FIG. 2. The AI lung analysis engine 316 may identify a possibility of one or more of abnormal breathing sounds, wheezing, congestive sounds, etc. The AI lung analysis engine 316 may use AI to determine a state or condition. The AI lung analysis engine 316 may use AI to determine a range of possible states or conditions. The AI lung analysis engine 316 may associate a probability with each determined state or condition.

The AI arteriolar analysis engine 318 may interpret audio of one or more arteries (and/or the space between such) taken by a sensor, such as the stethoscope 206 in FIG. 2. The AI arteriolar analysis engine 318 may identify a possibility of one or more of arterial insufficiency, narrowing, blockage, etc. The AI arteriolar analysis engine 318 may use AI to determine a state or condition. The AI arteriolar analysis engine 318 may use AI to determine a range of possible states or conditions. The AI arteriolar analysis engine 318 may associate a probability with each determined state or condition.

The AI venous analysis engine 320 may interpret audio of one or more vessels (veins/venules and/or the space in between such) taken by a sensor, such as the stethoscope 206 in FIG. 2. The AI venous analysis engine 320 may identify a possibility of one or more of venous insufficiency, narrowing, blockage, etc. The AI venous analysis engine 320 may use AI to determine a state or condition. The AI venous analysis engine 320 may use AI to determine a range of possible states or conditions. The AI venous analysis engine 320 may associate a probability with each determined state or condition.

The AI body temperature analysis engine 322 may interpret temperatures taken by a sensor, such as the IR thermometer 208 in FIG. 2. The AI venous analysis engine 320 may identify one of a normal temperature, a low grade fever, a significant fever, hypothermia, etc.

The AI body temperature analysis engine 322 may use AI to determine a state or condition. The AI body temperature analysis engine 322 may use AI to determine a range of possible states or conditions. The AI body temperature analysis engine 322 may associate a probability with each determined state or condition.

The AI EKG analysis engine 324 may interpret EKG measurements taken by a sensor, such as the EKG 210 in FIG. 2. The AI EKG analysis engine 324 may identify a possibility of one or more of normal, arrhythmia, tachycardia, bradycardia, atrial fibrillation, missed beat, premature atrial contraction (PAC), premature ventricular contraction (PVC), ST elevation, ST depression, ventricular premature beat (VPB), accidental VPB, VPB trigeminy, VPB bigeminy, VPB couple, VPB runs of 3, VPB runs of 4, VPB RonT, etc. The AI EKG analysis engine 324 may use AI to determine a state or condition. The AI EKG analysis engine 324 may use AI to determine a range of possible states or conditions. The AI EKG analysis engine 324 may associate a probability with each determined state or condition.

The AI pulse oximeter analysis engine 326 may interpret pulse measurements and/or oxygen saturation levels taken by a sensor, such as the pulse oximeter 212 in FIG. 2. The AI pulse oximeter analysis engine 326 may identify a possibility of one or more of a fast pulse rate (e.g. heart, etc.), a slow pulse rate, a normal pulse rate, a normal oxygen saturation level, a low oxygen saturation level, etc. The AI pulse oximeter analysis engine 326 may use AI to determine a state or condition. The AI pulse oximeter analysis engine 326 may use AI to determine a range of possible states or conditions. The AI pulse oximeter analysis engine 326 may associate a probability with each determined state or condition.

The AI body fat and/or muscle tone sensor analysis engine 328 may interpret body fat and/or muscle tone measurements taken by a sensor, such as the body fat and/or muscle tone sensor 214 in FIG. 2. The AI body fat and/or muscle tone sensor analysis engine 328 may identify a possibility of one or more of obesity, wasting, etc. The AI body fat and/or muscle tone sensor analysis engine 328 may additionally use user-entered data, such as height and weight, to determine a fitness level. The AI body fat and/or muscle tone sensor analysis engine 328 may use AI to determine a state or condition. The AI body fat and/or muscle tone sensor analysis engine 328 may use AI to determine a range of possible states or conditions. The AI body fat and/or muscle tone sensor analysis engine 328 may associate a probability with each determined state or condition.

The AI glucose analysis engine 330 may interpret a concentration of glucose in a blood sample taken by a sensor, such as the glucometer 226 in FIG. 2. The AI glucose analysis engine 330 may identify a possibility of one or more of normal, prediabetes, diabetes, hypoglycemia, etc. The AI glucose analysis engine 330 may use AI to determine a state or condition. The AI glucose analysis engine 330 may use AI to determine a range of possible states or conditions. The AI glucose analysis engine 330 may associate a probability with each determined state or condition.

The AI hematology analysis engine 332 may interpret cells in a blood sample taken by a sensor, such as the hematology analyzer 228 in FIG. 2. The AI hematology analysis engine 332 may identify a possibility of one or more of sickle cell, anemia, human immunodeficiency virus (HIV), etc. The AI hematology analysis engine 332 may use AI to determine a state or condition. The AI hematology analysis engine 332 may use AI to determine a range of possible states or conditions. The AI hematology analysis engine 332 may associate a probability with each determined state or condition.

The AI feedback engine 334 may take as input health states and/or conditions determined by other modules. The AI feedback engine 334 may use the totality of health states and/or conditions to determine a diagnosis. The AI feedback engine 334 may use the totality of health states and/or conditions, or a trend of such over time, to determine a range of diagnoses. Each entry in the range of diagnoses may comprise an associated degree of certainty. The AI feedback engine 334 may assign an urgency level to each diagnosis. The AI feedback engine 334 may assign an urgency level associated with a most urgent entry in the range of diagnoses to the range of diagnoses. The AI feedback engine 334 may assign an urgency level associated with a most likely entry in the range of diagnoses to the range of diagnoses. The AI feedback engine 334 may assign a recommendation to each diagnosis. The AI feedback engine 334 may assign a recommendation associated with a most urgent entry in the range of diagnoses to the range of diagnoses. The AI feedback engine 334 may assign a recommendation associated with a most likely entry in the range of diagnoses to the range of diagnoses.

Processes for Remote and/or Automated Medical Diagnosis

Figure 4:
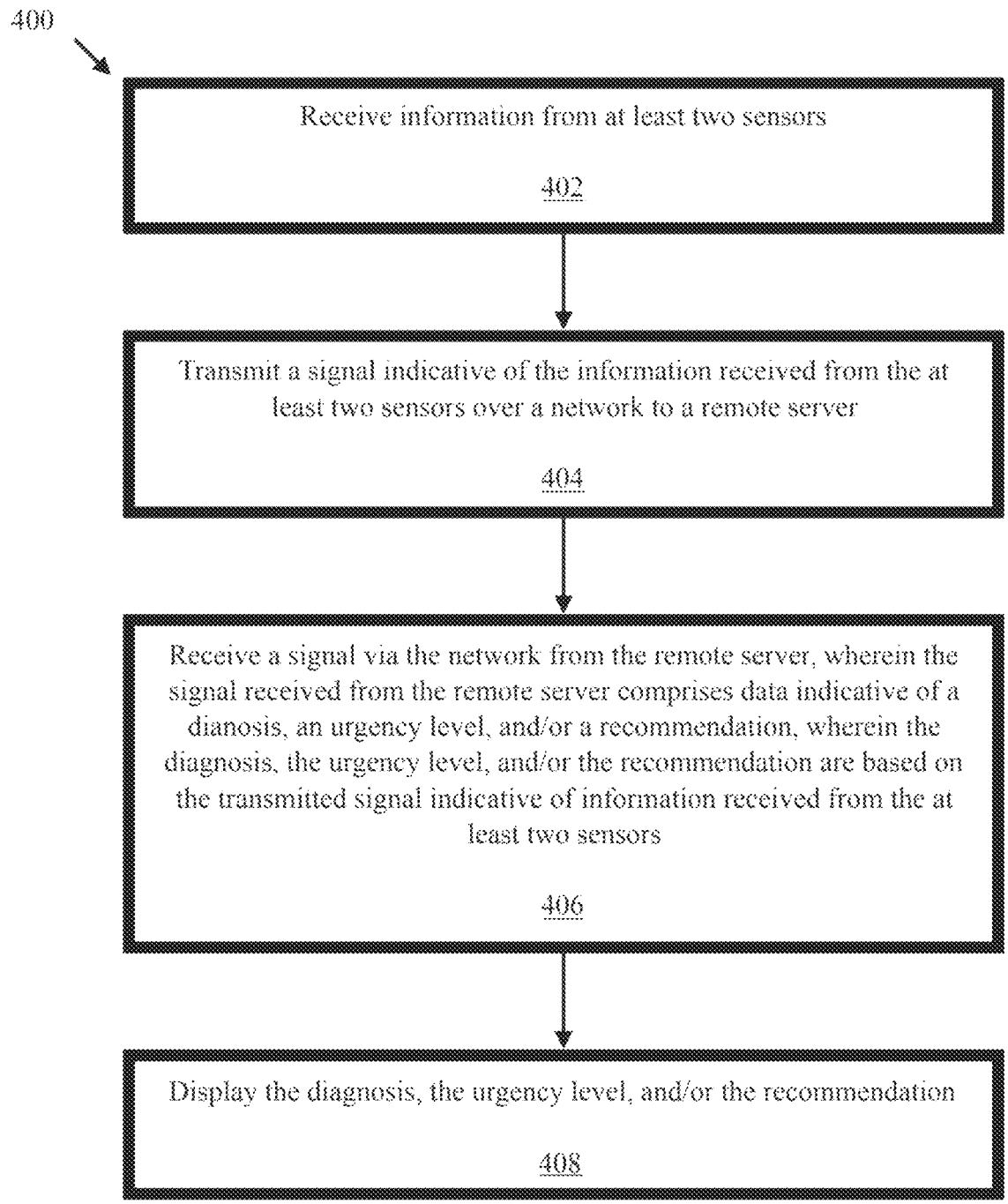
FIG. 4 illustrates a flowchart for remote and/or automated medical diagnosis in accordance with an exemplary embodiment of the invention.

FIG. 4 illustrates, in an example embodiment, method 400 of remote and/or automated medical diagnosis. In embodiments, the method steps or techniques depicted and described herein can be performed in a processor of the medical/consumer electronics device 140 in FIG. 1, the method steps being encoded as processor-executable instructions in a non-transitory memory of the medical/consumer electronics device 140. In embodiments, the method steps or techniques depicted and described herein can be performed in a processor the analysis system 120 in FIG. 1, the method steps being encoded as processor-executable instructions in a non-transitory memory of the telemedicine platform 120. The techniques of FIG. 4 may be implemented in an operating system kernel, in a separate user process, in a library package bound into network applications, on a specially constructed machine, on an application-specific integrated circuit (ASIC), or a field programmable gate array (FPGA).

At step 402, information may be received from at least two sensors. One of the at least two sensors may comprise and/or be associated with a high-magnification camera, a motorized camera, a stethoscope, an infrared (IR) thermometer, an electrocardiogram (EKG), a pulse oximeter, a body fat and/or muscle tone sensor, a glucometer, or a hematology analyzer. Information from the at least two sensors may comprise one or more of an eye image, a skin image, an car image, a nose image, a throat image, chest sounds, a body temperature, EKG measurements, pulse measurements, an oxygen saturation level, a body fat measurement, a muscle tone measurement, a glucose measurement, and a hematology measurement.

At step 404, a signal indicative of the information received from the at least two sensors may be transmitted over a network to a remote server. The remote server may comprise a telemedicine platform. The remote server may comprise a cloud computing environment. The remote server may comprise an artificial intelligence (AI) system. The AI system may be trained on data from a data repository.

At step 406, a signal may be received via the network from the remote server. The signal received from the remote server may comprise data indicative of a diagnosis, an urgency level, and/or a recommendation. The diagnosis, the urgency level, and/or the recommendation may be based on the transmitted signal indicative of information received from the at least two sensors. The diagnosis, the urgency level, and/or the recommendation may be based on the AI system. The diagnosis may comprise a list of possible conditions. The list of possible conditions may be ordered by likelihood. The list of possible conditions may be ordered by severity. The urgency level may comprise a number within a range. The range may comprise, for example, 1 to 5. The low number may be the least urgent. The high number may be the least urgent. The recommendation may comprise initiating a call with a telemedicine physician. If multiple possible conditions are determined, then the urgency level associated with the most urgent condition of the possible conditions may be selected. If multiple possible conditions are determined, then the urgency level associated with the most likely condition of the possible conditions may be selected.

At step 408, the diagnosis, the urgency level, and/or the recommendation may be displayed. Items in the list of possible conditions that are associated with a threshold urgency and/or severity level may be displayed in a particular color and/or property. For example, possible conditions associated with an elevated severity or higher may be displayed in red and bold lettering. The urgency level may be displayed in a particular color and/or property if it is associated with a threshold urgency level. For example, if the urgency level is measured between 1 and 5 with 5 being the most urgent, then urgency levels at 4 or higher may be displayed in red and bold lettering. Recommendations associated with a threshold urgency and/or severity level may be displayed in a particular color and/or property. For example, recommendations associated with an elevated severity or higher may be displayed in red and bold lettering.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the embodiments disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific embodiments, at least some of the features or functionalities of the various embodiments disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some embodiments, at least some of the features or functionalities of the various embodiments disclosed herein may be implemented in one or more virtualized computing environments (e.g., network computing clouds, virtual machines hosted on one or more physical computing machines, or other appropriate virtual environments).

Figure 5:
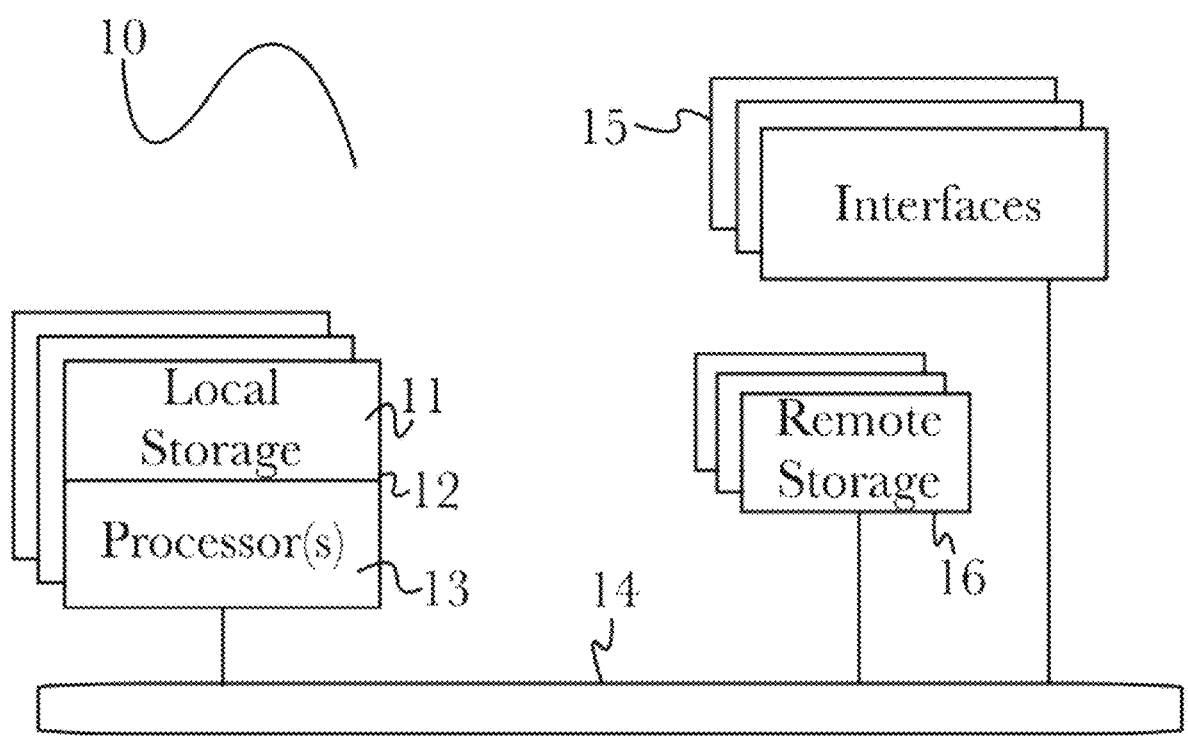
FIG. 5 illustrates components of an exemplary computing device that supports an embodiment of the inventive disclosure.

Referring now to FIG. 5, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some embodiments, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random-access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 5 illustrates one specific architecture for a computing device 10 for implementing one or more of the embodiments described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, single processor 13 handles communications as well as routing computations, while in other embodiments a separate dedicated communications processor may be provided. In various embodiments, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the embodiments described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

The medical/consumer electronics device 140 and/or the telemedicine platform 140 in FIG. 1 may be and/or comprise the computing device 10.

Because such information and program instructions may be employed to implement one or more systems or methods described herein, at least some network device embodiments may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 6:
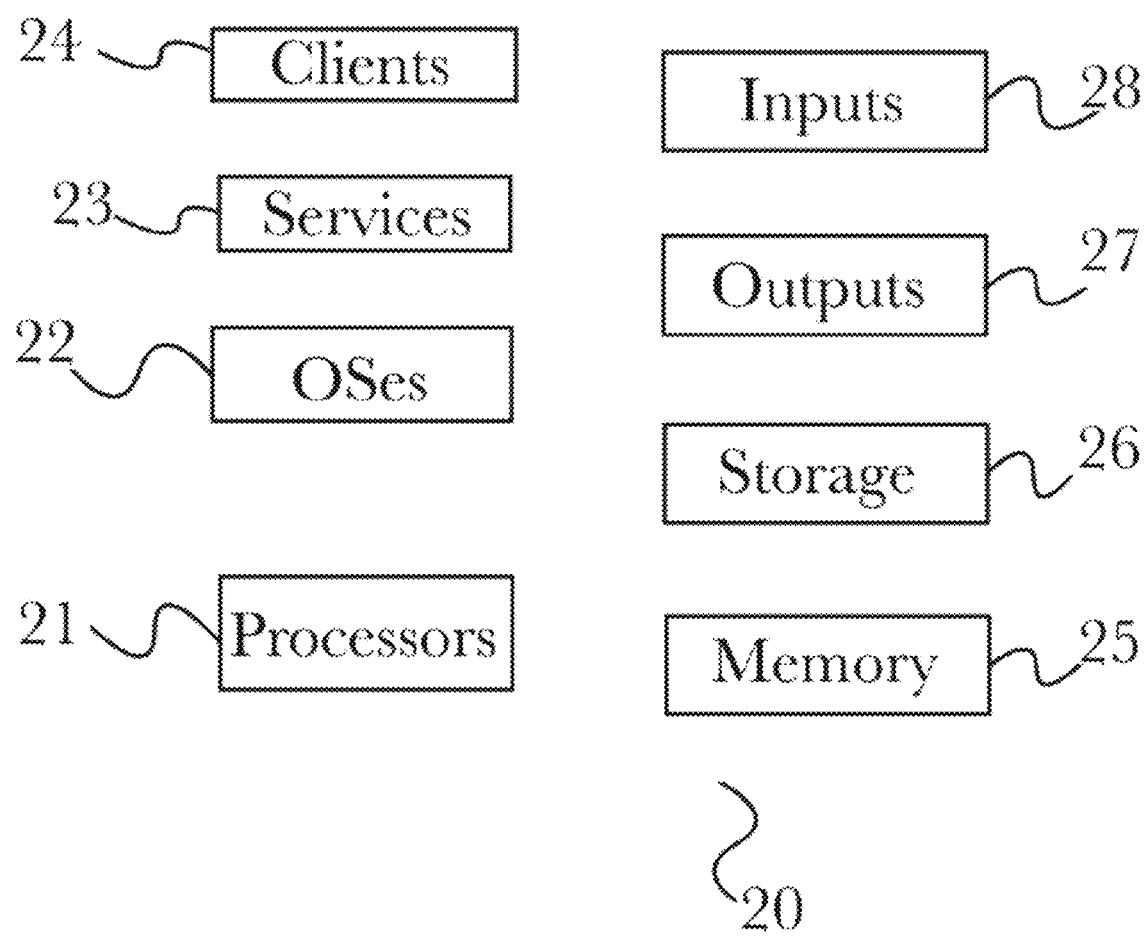
FIG. 6 illustrates one embodiment of a standalone computing system that supports an embodiment of the inventive disclosure.

In some embodiments, systems may be implemented on a standalone computing system. Referring now to FIG. 6 above, there is shown a block diagram depicting a typical exemplary architecture of one or more embodiments or components thereof on a standalone computing system. Computing device 20 includes processors 21 that may run software that carry out one or more functions or applications of embodiments, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 6). Examples of storage devices 26 include flash memory, magnetic hard drive, CD-ROM, and/or the like.

The medical/consumer electronics device 140 and/or the telemedicine platform 140 in FIG. 1 may be and/or comprise the system 20.

Figure 7:
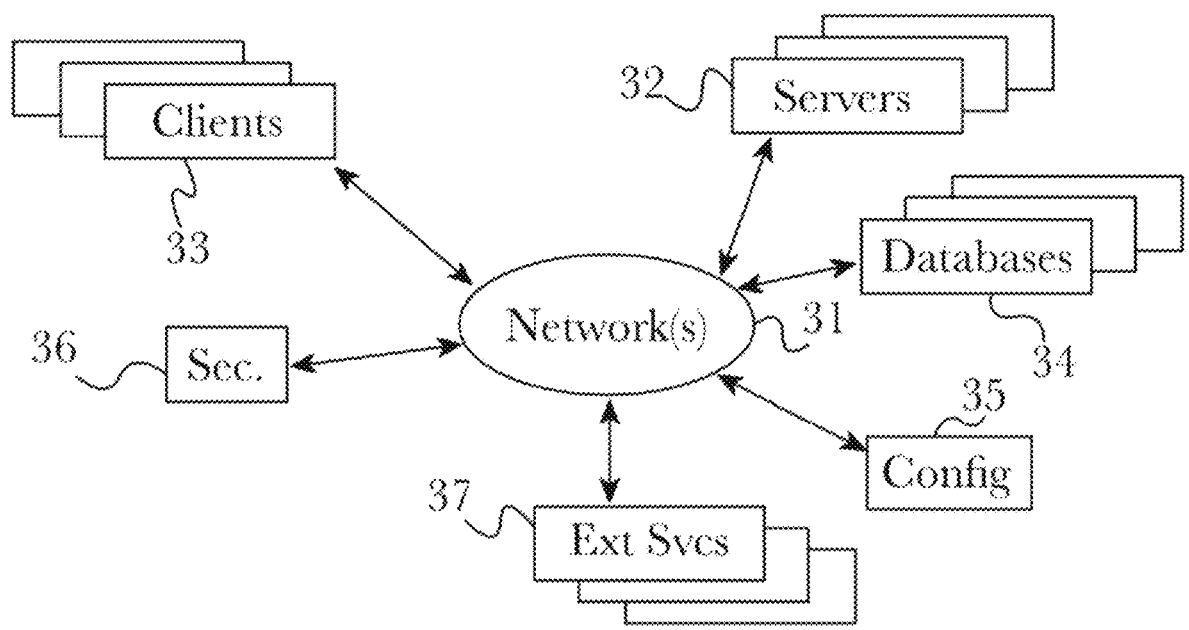
FIG. 7 illustrates an exemplary distributed computing network that supports an exemplary embodiment of the inventive disclosure.

In some embodiments, systems may be implemented on a distributed computing network, such as one having any number of clients and/or servers. Referring now to FIG. 7, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 6. In addition, any number of servers 32 may be provided for handling requests received from one or more clients 33. Clients 33 and servers 32 may communicate with one another via one or more electronic networks 31, which may be in various embodiments any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some embodiments, servers 32 may call external services 37 when needed to obtain additional information, or to refer to additional data concerning a particular call.

Communications with external services 37 may take place, for example, via one or more networks 31. In various embodiments, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises.

In some embodiments, clients 33 or servers 32 (or both) may make use of one or more specialized services or appliances that may be deployed locally or remotely across one or more networks 31. For example, one or more databases 34 may be used or referred to by one or more embodiments. It should be understood by one having ordinary skill in the art that databases 34 may be arranged in a wide variety of architectures and using a wide variety of data access and manipulation means. For example, in various embodiments one or more databases 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some embodiments, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system 2420. Unless a specific meaning is specified for a given use of the term "database", it should be construed to mean any of these senses of the word, all of which are understood as a plain meaning of the term "database" by those having ordinary skill in the art.

Similarly, some embodiments may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with embodiments without limitation, unless a specific security 36 or configuration system 35 or approach is specifically required by the description of any specific aspect.

The medical/consumer electronics device 140 and/or the telemedicine platform 170 and/or the data repository 130 and/or the third party stakeholder platform 180 and/or the analysis system 120 in FIG. 1 may be and/or comprise the one or more of the server(s) 32.

Figure 8:
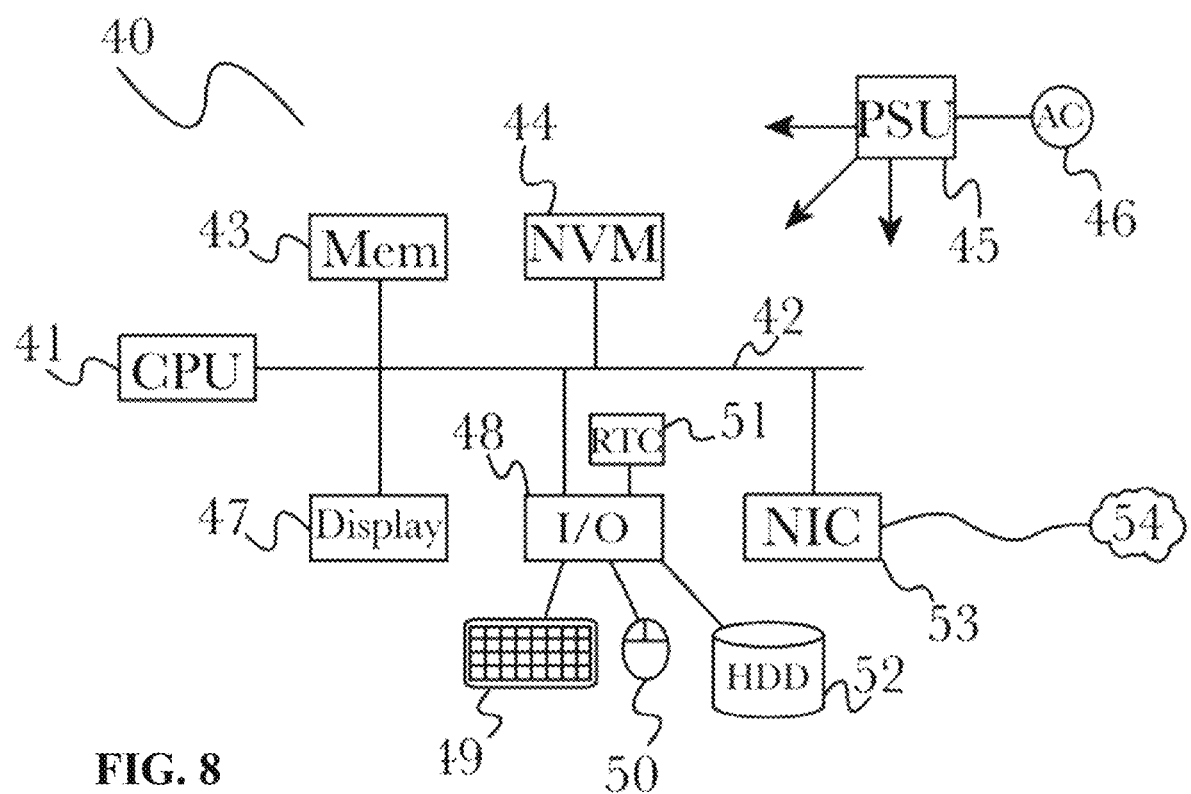
FIG. 8 illustrates an exemplary overview of a computer system that supports an exemplary embodiment of the inventive disclosure.

FIG. 8 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to keyboard 49, pointing device 50, hard disk 52, and real-time clock 51. NIC 53 connects to network 54, which may be the Internet or a local network, which local network may or may not have connections to the Internet. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

The medical/consumer electronics device 140 and/or the telemedicine platform 170 and/or the data repository 130 and/or the third party stakeholder platform 180 and/or the analysis system 120 in FIG. 1 may be and/or comprise the computer system 40.

In various embodiments, functionality for implementing systems or methods of various embodiments may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various embodiments described above. Accordingly, the present invention is defined by the claims and their equivalents.

Metaverse/Virtual World Telemedicine Integration

Figure 9:
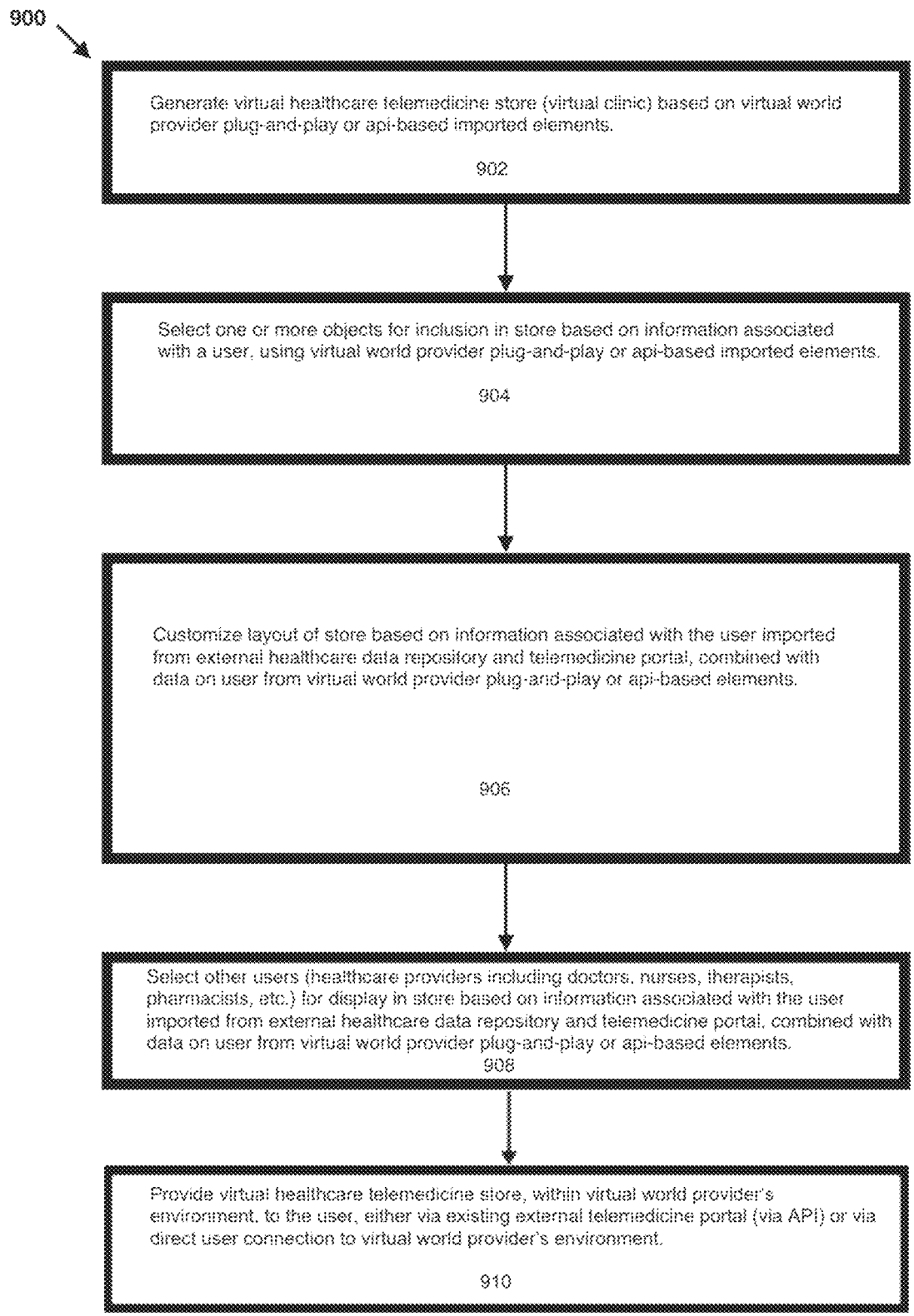
FIG. 9 illustrates a flowchart for remote and/or automated medical diagnosis and provision of care in accordance with an exemplary embodiment of the invention.

FIG. 9 illustrates, in an example embodiment, method 900 of remote and/or automated medical diagnosis and provision of care in a metaverse/virtual world. In embodiments, the method steps or techniques depicted and described herein can be performed in a virtual world/metaverse provider's environment, with possible assistance from/integration with one or more of the other systems, methods, and devices described in preceding sections and paragraphs of this disclosure.

At Step 902, a virtual healthcare telemedicine store (virtual clinic) is generated based on the virtual world provider's plug-and-play elements or API-based imported elements.

At Step 904, one or more objects for inclusion in the virtual store based on information associated with a user is selected, using the virtual world provider's plug-and-play or API-based imported elements.

At Step 906, a layout of the store based on information associated with the user imported from an external healthcare data repository (FIG. 1, 130) and telemedicine platform (FIG. 1, 170) is customized, combined with data on the user from the virtual world provider's plug-and-play or API-based elements.

At Step 908, other users (healthcare providers including doctors, nurses, therapists, pharmacists, etc.) are selected for display in the store based on information associated with the user imported from the external healthcare data repository (FIG. 1, 130) and telemedicine portal (FIG. 1, 170), combined with data on the user from the virtual world provider's plug-and-play or API-based elements.

At Step 910, a virtual healthcare telemedicine store is provided, within the virtual world provider's environment, to the user, either via the existing external telemedicine portal (FIG. 1, 170) (via API) or via direct user connection to the virtual world provider's environment.

The user may then interact with the virtual healthcare telemedicine store (within the virtual world provider's environment) in the same way s/he interacts with the pre-existing telemedicine application or website described in this disclosure, and may interact with the device(s) described in this disclosure and transmit data to (and receive data from) the virtual healthcare telemedicine store in conjunction with the pre-existing telemedicine application or website, the data repository, and all other network nodes and systems described in this disclosure.

Figure 10:
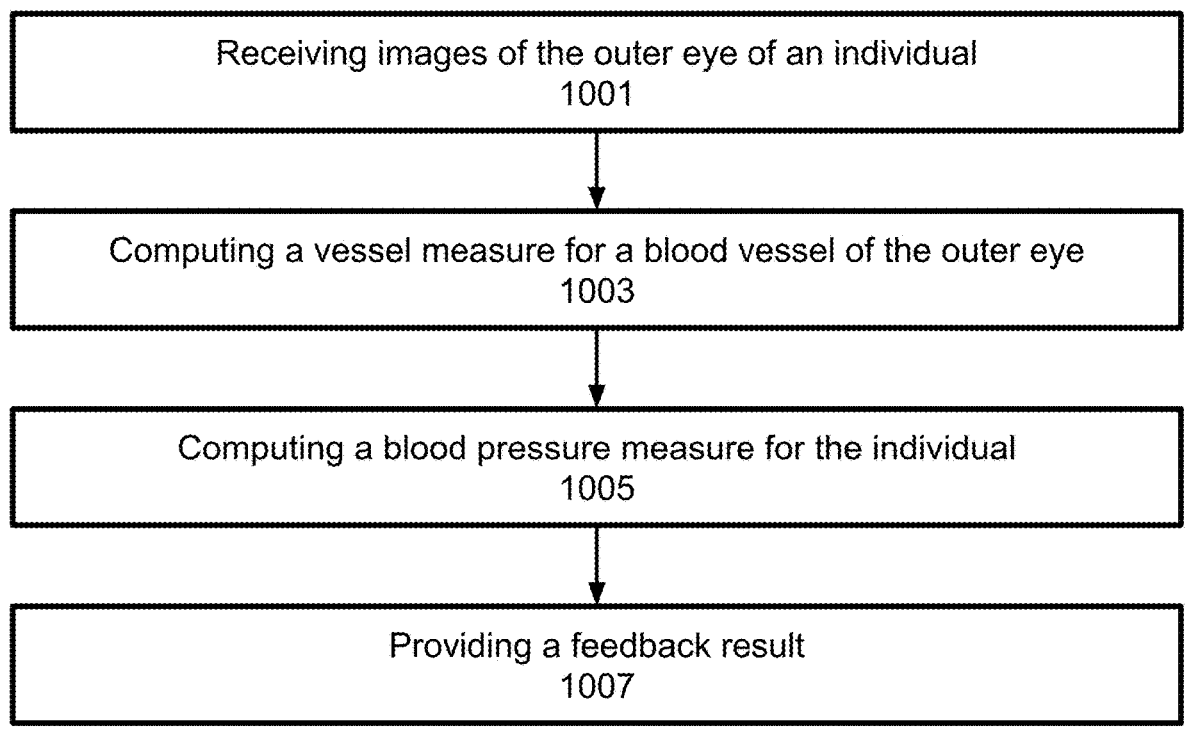
FIG. 10 illustrates an exemplary overview of a process for computing blood pressure based on images of the eye according to one exemplary embodiment of the inventive disclosure.

FIG. 10 illustrates, in an example embodiment, of a process for computing blood pressure of an individual based on images of the eye of the individual. The exemplary process comprises receiving images of the outer eye of an individual 1001, computing a vessel measure for a blood vessel of the outer eye 1003, computing a blood pressure measure for the individual 1005, and providing a feedback result 1007.

At step 1001, the process may comprise receiving images of the outer eye of an individual. The images may be received from an end-user handheld electronics device (e.g. medical/consumer electronics device 140 or 200). The end-user handheld electronics device may comprise and/or interface with a high-magnification camera operable to capture digital images and/or video of the outer eye of an individual. The high-magnification camera may be integral with the end-user handheld electronics device. The high-magnification camera may be operable to capture digital images and/or video of blood flowing through the vasculature of the outer eye. The end-user handheld electronics device may be operable to capture and provide a sequence of digital images to a remote server for further processing. The sequence of images may comprise a series of time-stamped images. The images may be received in real-time as the images are acquired by the end-user handheld electronics device.

At step 1003, the process may comprise computing a vessel measure for at least one blood vessel present in the received images. Computing a vessel measure may comprise applying a computer vision algorithm, via a processor, to analyze the received images. The computer vision algorithm may extract pixel value information associated with at least one pixel for each image in the received images (e.g. each image of a sequence of images). The computer vision algorithm may analyze extracted pixel information to determine at least one image characteristic, including, but not limited to, blood vessel diameter, blood vessel wall thickness, blood vessel length, distance between blood vessels or vessel segments, area between blood vessels or vessel segments, and a blood velocity measurement associated with at least one blood vessel. The computed vessel measure may comprise one of the image characteristics. The computed vessel measure may comprise a measure computed from a combination of the image characteristics. The computed vessel measure may comprise a measure computed using at least one of the image characteristics. For example, the image characteristics may be used to compute at least one characteristic associated with blood flow through a vessel, including, but not limited to pressure, volume, resistance, volumetric flow rate, flow velocity, and cross sectional area associated with a blood vessel. The computer vision algorithm may determine at least one metric for the series of images including, but not limited to, at least one of a minimum blood vessel diameter, a maximum blood vessel diameter, an average blood vessel diameter, a minimum blood vessel wall thickness, a maximum blood vessel wall thickness, an average blood vessel wall thickness, an area between blood vessels (e.g. an area formed by surrounding blood vessels), a distance between blood vessels (e.g. a distance between the outer wall of a first blood vessel and the outer wall of a second blood vessel), a minimum blood velocity, a maximum blood velocity, and an average blood velocity. The computer vision algorithm may compute a vessel measure for at least one blood vessel based on the at least one metric for the series of images. In one aspect, blood flow characteristics may be computed based on the at least one image characteristic. In one aspect, changes in at least one of blood vessel diameter, blood vessel wall thickness, distance between blood vessels or vessel segments, and area between blood vessels or vessel segments, may indicate a change in blood flow characteristics. For example, an increase in blood vessel diameter may be associated with an change in blood flow characteristics (e.g. decreased pressure, increased volume, and/or decreased velocity), while a decrease in blood vessel diameter may be associated with an opposite change in flow characteristics (e.g. increased pressure, decreased volume, and/or increased velocity. Similarly, a decrease in the space between blood vessels (e.g. distance, area, etc.) may indicate an increase in blood vessel diameter of the blood vessels associated with that space due to increased flow (e.g. decreased pressure, increased volume, and/or decreased velocity). In other words, a decrease in the space between blood vessels may indicate an increase in flow characteristics, while an increase in the space between blood vessels may indicate a decrease in flow characteristics.

The computer vision algorithm may comprise a pre-processing step or algorithm(s) operable to prepare the images for further analysis. Pre-processing may include, but is not limited to, noise reduction, filtering, smoothing, contrast enhancement, artifact removal, scaling, dilation, erosion, etc. The computer vision algorithm may comprise at least one of object detection, edge detection, video tracking, object recognition, 3D pose estimation, and motion estimation (e.g. tracking and/or optical flow). The computer vision algorithm may comprise windowing such that selective processing is performed on pixels meeting certain value criteria (e.g. a minimum value threshold, a maximum value threshold). The computer vision algorithm may comprise area of interest or region of interest analysis, such that selective processing is performed on pixels within a specified location within the image (e.g. locations where blood vessels are identified). The computer vision algorithm may determine velocity by tracking at least one pixel within a specified region of interest. The region of interest may be of a specified size. The region of interest may be a fixed size. The region of interest may be smaller than the total size of an image being analyzed. The region of interest may be at a fixed location across a sequence of images.

The computer vision algorithm may be trained using machine learning techniques such as neural networks and/or deep learning. The computer vision algorithm may be trained using at least one of supervised learning, unsupervised learning, semi-supervised learning, and reinforcement learning. The computer vision algorithm may be trained using at least one of linear regression, logistic regression, decision trees, random forest algorithm, support vector machines, Naïve Bayes algorithm, random walk algorithm, k-nearest neighbor algorithm, k-means clustering, and Markov models. These training approaches are merely exemplary and other training approaches/techniques may be used without departing from the scope of the invention as would be apparent to one of ordinary skill in the art. The computer vision may be trained using labeled images. The labeled images may comprise labels (e.g. labeled pixels) for at least one of a blood vessel, blood vessel wall, blood flow region, inner blood vessel diameter, outer blood vessel diameter, distance between blood vessels or vessel segments, area between blood vessels or vessel segments, and blood velocity.

At step 1005, the process may comprise computing a blood pressure measure for an individual based on obtained images of the outer eye of the individual. Computing a blood pressure measure may comprise computing, by a processor, a blood pressure measure using an artificial intelligence (AI) analysis algorithm. The AI analysis algorithm may relate at least one image characteristic and/or a computed vessel measure (e.g. as determined by the computer vision algorithm) to blood pressure values. The AI analysis algorithm may be trained using machine learning techniques such as neural networks and/or deep learning. The AI analysis algorithm may be trained using at least one of supervised learning, unsupervised learning, semi-supervised learning, and reinforcement learning. The AI analysis algorithm may be trained using at least one of linear regression, logistic regression, decision trees, random forest algorithm, support vector machines, Naïve Bayes algorithm, random walk algorithm, k-nearest neighbor algorithm, k-means clustering, and Markov models. These training approaches are merely exemplary and other training approaches/techniques may be used without departing from the scope of the invention as would be apparent to one of ordinary skill in the art.

The AI analysis algorithm may be trained using previously acquired images of the outer eye vasculature of the individual and/or previously obtained blood pressure measurements associated with the individual. The previously acquired images may have been processed using the computer vision algorithm as described above. The AI analysis algorithm may be trained using previously acquired and processed images of the outer eye of the individual obtained in combination (e.g. simultaneously) with previously obtained blood pressure measurements associated with the individual. The previously acquired images and previously acquired blood pressure measurement may be obtained in combination with each other (e.g. simultaneously) at a plurality of different timepoints (e.g. multiple time points over the course of a day and/or several days or weeks). For example, for each user or individual being examined/imaged using the end-use handheld electronics device, corresponding outer eye vasculature imaging and blood pressure measures may be repeated over time for use in training an AI analysis algorithm. In one aspect, the AI analysis algorithm may rely on a generalized model trained using broader population data (e.g. a combination of images and blood pressure measures for a plurality of different individuals) in computing blood pressure measures. In one aspect, the corresponding imaging and blood pressure measures acquired for each user or individual are used to train an AI analysis algorithm unique to the user or individual. Because each individual may have different outer eye vasculature characteristics which may correspond to different blood pressure measures as compared to other individuals, an AI analysis algorithm unique to each individual may allow for a more accurate blood pressure measurement than a generalized model which attempts to compute blood pressure using a model trained using broader population data.

The AI analysis algorithm may compute an amount of change in at least one image characteristic (e.g. as determined by the computer vision algorithm). The AI analysis algorithm may compute the amount of change by comparing at least one current image characteristic with at least one previously computed image characteristic associated with the individual (e.g. from images previously acquired on a different day and/or time, such as baseline images and/or images used in training). The AI analysis may compute a percentage change in at least one image characteristic. The AI analysis algorithm may compute the blood pressure measure based on the amount of change. The AI analysis algorithm may compute blood pressure based on magnitude of change such that the computed blood pressure increases or decreases by an amount relative to the magnitude of change. The AI analysis algorithm may compute blood pressure based on the direction of change such that the computed blood pressure increases or decreases in relation to whether the computed change is an increase or decrease. The AI analysis algorithm may compute an amount of change in the space between blood vessels between a current image(s) and previously acquired image(s). The change in space between blood vessels may serve as an indicator of vessel diameter change which can be an indicator of blood flow changes (e.g. pressure, volume, velocity, etc.). For example, a decrease in the space between blood vessels between previous images and current images may indicate a lower blood pressure at the current time as compared to the previous time due to expansion of the blood vessel diameter which thereby reduced the computed space between blood vessels. Although described herein as separate algorithms, the computer vision algorithm and AI analysis algorithm could be combined into a single algorithm performing the combined functions of each individual algorithm without departing from the scope of the invention. Similarly, each algorithm could be further broken down into smaller or sub-algorithms which collectively perform the same fundamental functions without departing from the scope of the invention.

At step 1007, the process may comprise providing a feedback result to the handheld end-user electronics device. The feedback result may be provided via network communication. The feedback result may comprise at least the computed blood pressure. The feedback result may comprise at least one of the above computed metrics including, but not limited to, computed blood pressure, blood vessel diameter, blood vessel wall thickness, blood vessel length, distance between blood vessels or vessel segments, area between blood vessels or vessel segments, a blood velocity measurement associated with at least one blood vessel, and computed change metrics. Providing a feedback result may comprise providing a feedback result in near real-time, such that upon receiving images from a handheld end-user device, the images are processed according to the above and upon completion of processing the feedback result is promptly provided to the end-user electronics device for display. The feedback result may be at least one of prepared in a format and converted to a format transmissible over a network. The feedback result may be prepared in a format and/or communicated in a format suitable for display on the handheld end-user electronics device.

Figure 11A:
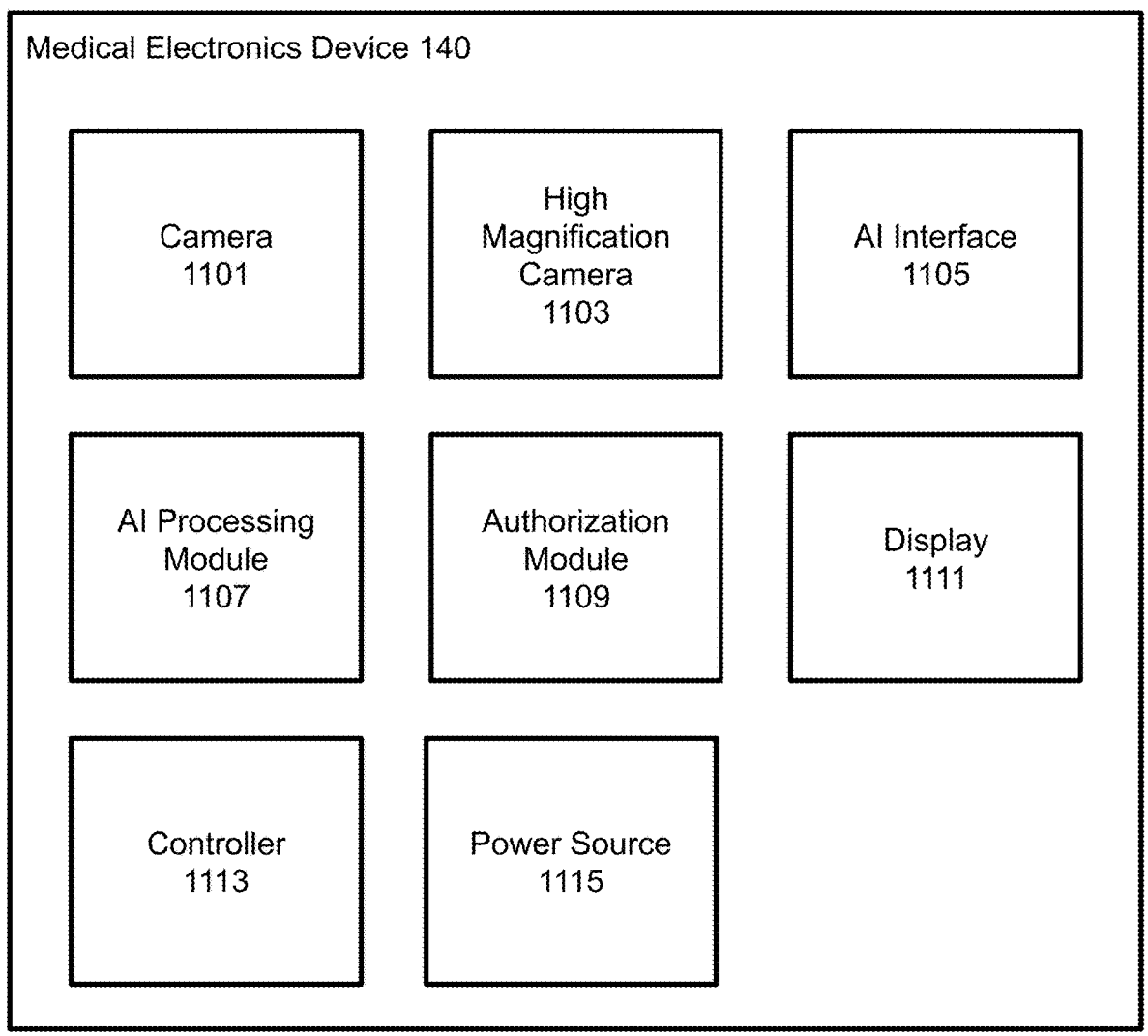
FIG. 11A illustrates an exemplary medical electronics device in accordance with an exemplary embodiment of the invention.

FIG. 11A illustrates an exemplary medical electronics device 140 for gathering and analyzing biometric information. The device 140 may comprise camera 1101, a high magnification camera 1103, an AI interface 1105, an AI processing module 1107, an authorization module 1109, a display 1111, a controller 1113, and a power source 1115.

The camera 1101 may comprise a device capable of capturing images of an eye of an individual. The camera 1101 may transmit the image(s) to a controller 1113. The camera 1101 may be a digital capture device that is capable of capturing 1080p resolution or higher. The camera 1101 may be capable of capturing an image of at least a portion of an eye in detail. The camera 1101 may be capable of capturing an image of the structures of the outer eye including at least the blood vessels and scleral tissue. Camera 1101 may comprise a visible light camera (e.g. an RGB camera). The camera 1101 may comprise an image sensor, including but not limited to at least one of a CMOS sensor, reflective mirror sensor, and CCD sensor. The image may be captured in various file formats, including JPEG for compressed, widely compatible photos, RAW for high-quality, unprocessed images, and TIFF for lossless, high-resolution files. The camera 1101 may also be a device capable of importing images of the same resolution which may include, but is not limited to a scanner or a data reading device.

The high magnification camera 1103 may comprise a device capable of capturing images of an eye of a user. The high magnification camera 1103 may transmit the image(s) to a controller 1113. The high magnification camera 1103 may be operable to capture images at a magnification greater than that of camera 1101. The high magnification camera 1103 may be a digital capture device that has a resolution higher than the camera 1101. In an embodiment of the invention, the high magnification camera 1103 may have magnification capability of 5×, 10×, 50×, 300×, 500×, 1000×. These are merely exemplary and any magnification camera capable of capturing blood flow could be used. The high magnification camera 1103 may comprise an image sensor, including but not limited to at least one of a CMOS sensor, reflective mirror sensor, and CCD sensor. Single lens, multi-lens, software/hardware based magnification. The high magnification camera 1103 may be capable of capturing a series of images at a frequency such that the blood flow in an eye can be observed. High magnification camera 1103 may comprise a visible light camera (e.g. an RGB camera). The image may be captured in various file formats, including JPEG for compressed, widely compatible photos, RAW for high-quality, unprocessed images, and TIFF for lossless, high-resolution files. The camera 1103 may also be a device capable of importing images of the same resolution which may include, but is not limited to a scanner or a data reading device.

The artificial intelligence (AI) interface 1105 may comprise a set of components capable of transmitting the information captured from the cameras 1101 and 1103 to an artificial intelligence processing module. The AI interface 1105 may receive input from an AI processing module such as AI inferences or other output resulting from AI processing of the images. The AI interface 1105 may include a set of wires for transmitting data, or a wireless transmitter, which may include, but is not limited to Wi-Fi, Bluetooth, and cellular networks. The AI interface in an alternative embodiment, may be omitted in favor of storing the AI onto the medical electronics device 140.

The artificial intelligence (AI) processing module 1107 may comprise a computer readable medium comprising code or computer readable instructions for executing a series of steps for analyzing the images captured by the cameras 1101 and 1103. The AI processing module 1107 may comprise either a database or a component for connection to a remote database which contains identity information about users. Although depicted as part of the medical electronics device 140, the AI processing module 1107 may be located external to or remote from medical electronics device 140 in which case the AI interface 1105 serves as the communication interface between medical electronics device 140 and AI processing module 1107. The AI processing module 1107 may determine at least one pattern characteristic of the vasculature from the first image captured by the camera 1101. This pattern characteristic recognition may be executed by at least one of convolutional neural networks (CNNs) for deep learning, and image segmentation algorithms for precise region identification. The AI processing module 1107 may determine at least one blood flow characteristic from the series of second images. Determining blood flow characteristic may comprise comparison of a plurality of images captured from the high magnification camera 1103. The analysis may comprise comparing the image of vasculature within the eye to see the blood flow and providing a blood flow analysis. The steps may further comprise comparing the at least one pattern characteristic and the at least one blood flow characteristic with a database of previously established pattern characteristics and blood flow characteristics for a plurality of individuals. The comparison may provide at least one indication of a match to an individual and a confidence in the level of match. AI processing module 1107 may verify the identity of a user based on the match. The AI processing module 1107 may use a set of thresholding rules to compare the image characteristics (pattern and blood flow) with the known characteristics of users in the database. The database may be remotely connected to the device 140 or contained on the device 140.

Other image analysis techniques known in the art may be utilized to form both the vasculature pattern and the blood flow analysis.

The authorization module 1109 may comprise a computer readable medium that comprises code or computer readable instructions for determining authorizations based on the identity information determined by AI processing module 1107. The authorization module 1109 may compare an identified user with a set of permissions for the identified user. This may determine if a user has permission to access at least one of an area, a device, and information. In one aspect, the authorization check may be performed in response to an access request prompting the above described image acquisition and processing. If the identified user has appropriate permissions as determined by the authorization module 1109, access may be provided and if insufficient permissions are present, access will be denied. Alternatively, if the user identity can not be determined from the analysis, access will be denied and the user will be notified that the user identity could not be determined.

The display 1111 may comprise a screen in communication with the controller 1113. The screen may comprise at least one of a black and white screen, a color screen, a light, or other indicator means known in the art. The screen is capable of displaying the results of the analysis performed by at least one of the AI processing module 1107 and authorization module 1109. For example, the display 1111 may display at least one of a determined identity of an individual resulting from analysis of the obtained images (e.g. displaying an individual's name, likeness (e.g. a picture of the individual), and/or other identifying information). The display may display at least one indicator of the authorization status of the user (e.g. whether access is granted or denied, the level of access of the user being granted, the level of access needed for the user to gain the requested access, etc.). The screen may be located on the device or in an alternative embodiment of the invention it may be located remotely from the device.

The controller 1113 may comprise a microprocessor, computer and/or control circuitry capable of interfacing with the cameras 1101 and 1103, the AI interface 1105, the AI processing module 1107, the authorization module 1109 and the display 1111. The controller may comprise a user interface capable of receiving input and providing an indication of the instructions sent to the device 140.

The power source 1115 may provide the energy to operate the device 140. The power source 1115 may comprise a battery or may be hardwired for connection to an external power supply (e.g. an outlet, power grid, etc.).

Figure 11B:
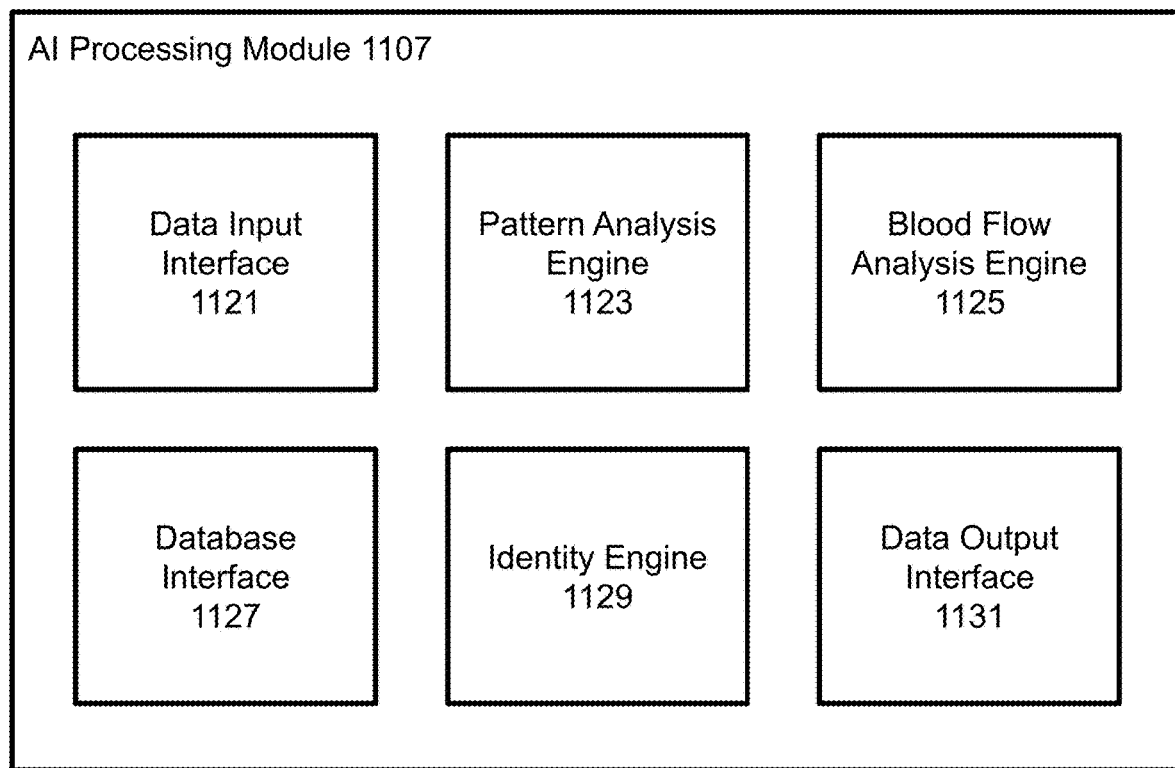
FIG. 11B illustrates an exemplary AI processing module in accordance with an exemplary embodiment of the invention.

FIG. 11B illustrates an exemplary AI processing module 1107 for analyzing obtained images (e.g. those obtained via a medical electronics device 140). The AI processing module 1107 may comprise data input interface 1121, a pattern analysis engine 1123, a blood flow analysis engine 1125, a database interface 1127, an identity engine 1129, and a data output interface 1131.

The data input interface 1121 may comprise at least one of computer readable instruction and a device for importing images into the AI processing module 1107. This interface may include physical connections, such as a direct connection to the cameras 1101 and 1103, USB and memory card slots. Wireless methods comprising at least one of Wi-Fi and Bluetooth may enable image import without the use of a physical connection. Alternatively, cloud-based services can be accessed by the data input interface 1121. File types may comprise, but are not limited to, JPEG for compressed, widely compatible photos, RAW for high-quality, unprocessed images, and TIFF for lossless, high-resolution files. The data input interface 1121 may standardize the input images into a universal format.

The pattern analysis engine 1123 may comprise a computer readable medium comprising code or computer readable instructions operable to execute a series of steps that is capable of analyzing a single image to detect patterns within the image. In an embodiment of the invention, the images comprise images of an eye, in particular the outer eye and corresponding scleral vasculature. Pattern analysis engine 1123 may apply image pre-processing to address common image quality issues such as blur, noise, etc. Pattern analysis engine 1123 may apply pre-processing to prepare the images for further analysis such as contrast enhancement in the image to make the vessels more prominent. These images may go through edge detection to highlight the blood vessels present. Once the blood vessels are clear in the image, and noise has been reduced, the width of the blood vessels may be skeletonized to simplify the pattern present. The bifurcation and crossover points may be identified as well. These steps would then create an eye pattern that can be compared to those in a database. In one aspect, the pattern of the vasculature may be used as the identified pattern for comparison purposes. In one aspect, the pattern of the sclera around blood vessels may be used as the identified pattern for comparison purposes.

The blood flow analysis engine 1125 may comprise a computer readable medium comprising code or computer readable instructions operable to execute a series of steps that is capable of analyzing multiple high definition images to create at least one of a blood flow diagram and a blood flow metric. The blood flow analysis engine 1125 may analyze blood flow (e.g. velocity) in the same manner as discussed above with respect to FIG. 10. The blood flow analysis engine may comprise the steps of reducing noise by using temporal and spatial filters in the sequence of images. The blood flow analysis engine 1125 may also comprise steps to align the sequence of images to account for any slight movements of the eye during capture. The blood flow analysis engine 1125 may then compute the motion vector of each pixel between frames. Techniques like the Lucas-Kanade method or Horn-Schunck method can be applied to detect and visualize blood flow. The blood flow analysis engine 1125 may then compute the flow velocity by analyzing the displacement of blood over time or by other known methods in the art. Similarly, the blood flow analysis engine 1125 may compute the flow direction in each vessel. The blood flow analysis engine 1125 may use the width and speed of blood vessels, approximate the volume of blood flow. The blood flow analysis engine 1125 may also perform pulse wave analysis to observe the pulsatile nature of blood flow, which could be influenced by heartbeats, to extract unique features.

The database interface 1127 is operable to interface with a database of previously acquired images and/or image processing results for a plurality of different individuals. The database interface 1127 is operable to obtain data from the database for comparison with the current images being analyzed such as for matching analysis of the currently identified pattern and blood flow characteristics with pattern and blood flow characteristics stored in the database. The database interface 1127 may be used to periodically update the database with new images or image characteristics (e.g. adding new individuals to the database) and/or to refine or replace older entries.

The identity engine 1129 may comprise a computer readable medium comprising code or computer readable instructions operable to execute a series of steps that is capable of analyzing the processed images from the pattern analysis engine 1123 and the blood flow analysis engine 1125 to match to the data extracted from the database interface 1127 to identify the user. The steps may comprise matching the image to a template of similar images to speed up the matching step. The templates may be stored on the device 140 or on a database 130. Dynamic templates may be employed in an embodiment of the invention. Dynamic templates may capture the essence of an individual's blood flow patterns over time. Matching the blood flow may comprise a step of feature vector comparison by creating a feature vector for each image, then measuring the similarity of the new image's feature vector to those in the database using cosine similarity. As the steps are repeated, the AI processing module 1107 may be improved through machine learning to classify or identify individuals based on the extracted features. The steps may also be improved through at least one of hashing techniques to reduce the dimensionality of feature vectors and speed up the search and nearest neighbor search to find the closest match in the database.

The data output interface 1131 may comprise a device to connect the AI processing module 1107 to the device 140. The interface 1131 may provide encryption steps to provide anonymity to a user and the data within the database.

Figure 12:
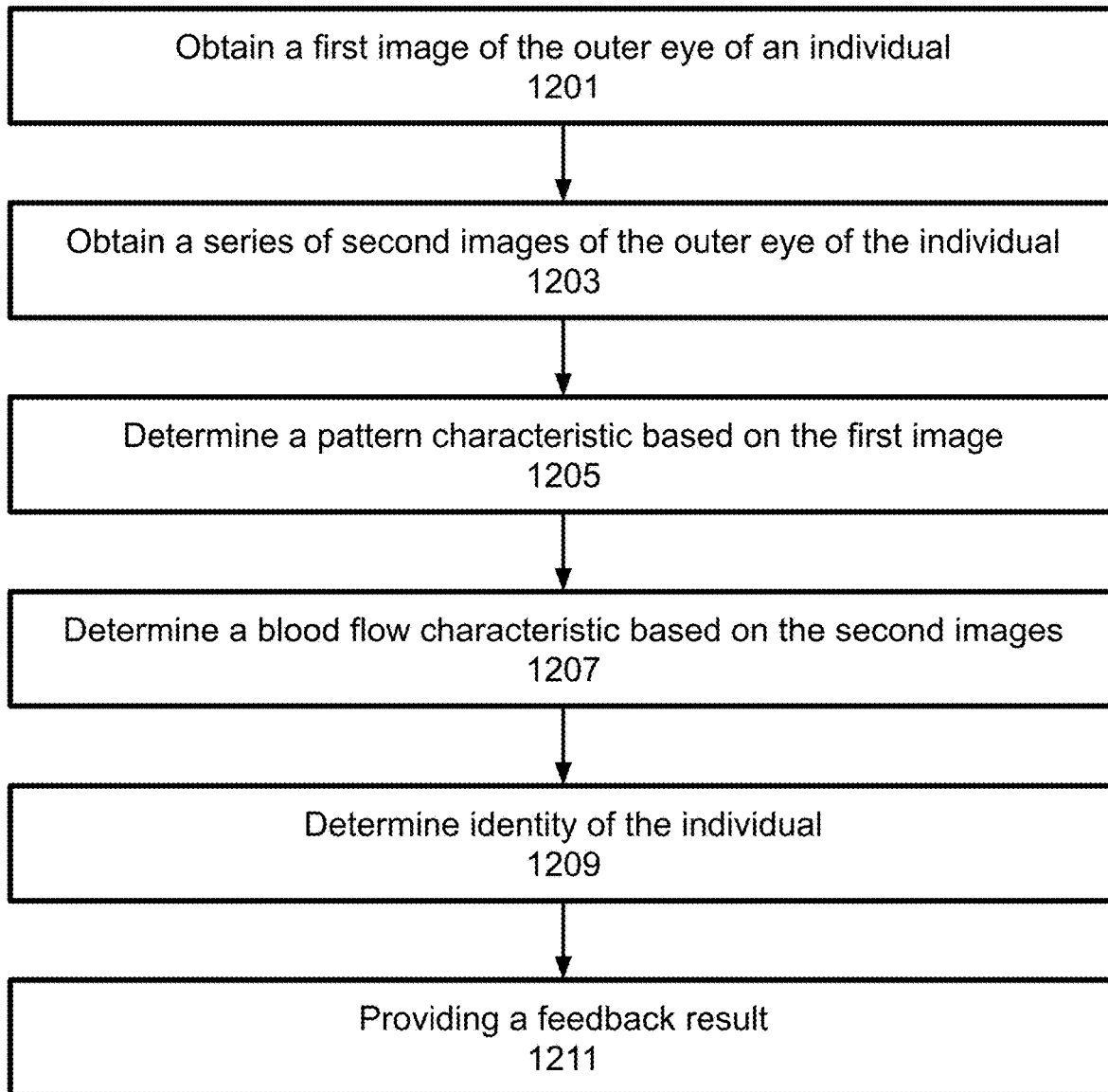
FIG. 12 illustrates a method of gathering and analyzing biometric information in accordance with an exemplary embodiment of the invention.

FIG. 12 illustrates a method of gathering and analyzing biometric information. The method may comprise the steps of obtain a first image of the outer eye of an individual 1201, obtain a series of second images of the outer eye of the individual 1203, determine a pattern characteristic based on the first image 1205, determine a blood flow characteristic based on the second images 1207, determine identity of the individual 1209, providing a feedback result 1211

Obtain a first image of the outer eye of an individual 1201 may comprise using a first image capture device to take an image of the user's eye. In an embodiment of the invention a single image is obtained, but multiple images could be used for improving the reliability of the analysis. Alternatively, the image or plurality of images may be obtained from other digital readable media. The first image generally comprises the structures of the outer eye including at least blood vessels and scleral tissue.

Obtain a series of second images of the outer eye of the individual 1203 may comprise using a high resolution image capture device capable of imaging blood flow within the blood vessels of an eye to capture a series of images over time. The images may be labeled in the order they were obtained in order to show the flow direction of blood within the vessels of the eye. Alternatively, these images may be obtained from other digital readable media. Alternatively, the high resolution image capture device may be the same device as the first image capture device.

Determine a pattern characteristic based on the first image 1205 may comprise analyzing the image from the first image capture device. The determination 1205 may comprise reducing noise in the image through image processing techniques known in the art. In addition, the determination of a pattern characteristic 1205 may comprise enhancing the contrast within the obtained image(s) to further highlight the blood vessels. The determination of a pattern characteristic 1205 may comprise skeletonizing the blood vessels and highlighting the bifurcation and crossover points in the blood vessels. At the end of determination of a pattern characteristic 1205 a pattern is generated for comparison with other patterns within a database of known individual patterns.

Determine a blood flow characteristic based on the second images 1207 may comprise analyzing the images from the high resolution image capture device. The blood flow characteristic analysis 1207 may comprise the steps of reducing noise by using temporal and spatial filters in the sequence of images. The blood flow characteristic analysis 1207 may also comprise steps to align the sequence of images to account for any slight movements of the eye during capture. The blood flow characteristic analysis 1207 may then compute the motion vector of each pixel between frames. Techniques like the Lucas-Kanade method or Horn-Schunck method can be applied to detect and visualize blood flow. The blood flow characteristic analysis 1207 may then compute the flow velocity by analyzing the displacement of blood over time or by other known methods in the art. Similarly, the blood flow characteristic analysis 1207 may compute the flow direction in each vessel. The blood flow characteristic analysis 1207 may use the width and speed of blood vessels, approximate the volume of blood flow. The blood flow characteristic analysis 1207 may also perform pulse wave analysis to observe the pulsatile nature of blood flow, which could be influenced by heartbeats, to extract unique features.

Determine identity of the individual 1209 may comprise comparing the analysis from the pattern characteristic 1205 and blood flow characteristic analysis 1207 to the known patterns and blood flow characteristics. Determine identity of the individual 1209 may involve using static and dynamic templates to speed up the matching process. The steps may be improved over time by utilizing machine learning to improve the accuracy of the matching process.

Providing a feedback result 1211 may comprise at least one of providing a message or indication or providing access of a locked or restricted area or data. The result may be provided through at least one of a display and indicator known in the art. Inconclusive results from the step of determine identity of the individual 1209 may provide a separate indication for a user encouraging them to provide new images.

Figure 13:
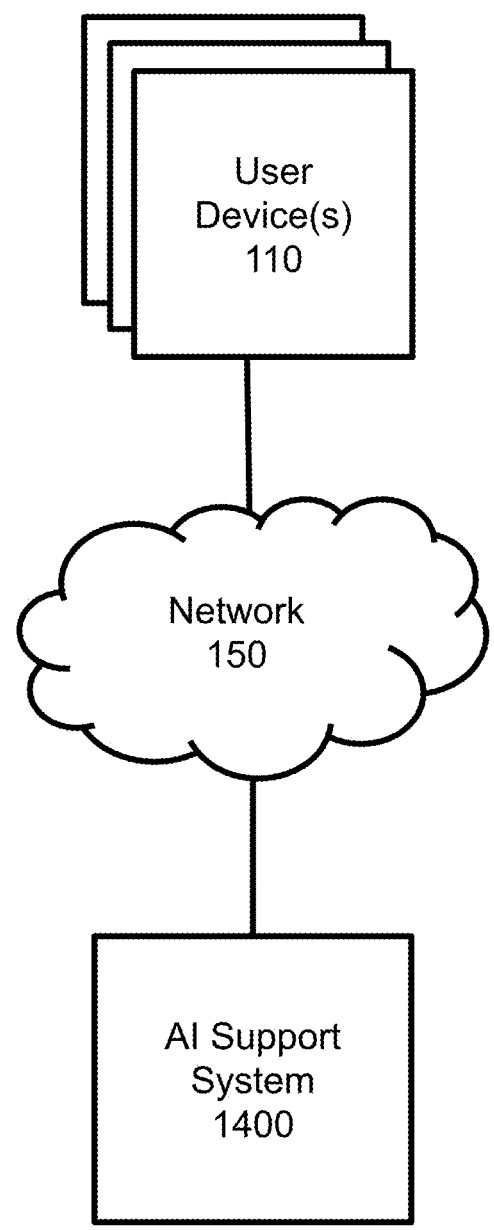
FIG. 13 illustrates exemplary systems and methods for artificial intelligence standard of care support in accordance with an exemplary embodiment of the invention.

FIG. 13 illustrates an exemplary embodiment of systems and methods for artificial intelligence standard of care support according to one embodiment. The system includes user device(s) 110, AI support system 1400, and a network 150 over which the various systems communicate and interact. The various components described herein are exemplary and for illustration purposes only and any combination or subcombination of the various components may be used as would be apparent to one of ordinary skill in the art. The system may be reorganized or consolidated, as understood by a person of ordinary skill in the art, to perform the same tasks on one or more other servers or computing devices without departing from the scope of the invention.

In one embodiment, the AI support system 1300 is designed to enhance provider diagnosis and ensure adherence to the standard of care by processing patient information obtained from user device(s) 110. The user device(s) 110 collect various forms of patient health data, which may include patient-reported symptoms, sensor data from medical devices, and electronic health records. This information is then transmitted to the AI support system 1300 for further analysis. The user device(s) 110 may comprise user devices 160 and/or medical/consumer electronics devices 140 as described in at least FIG. 1 above.

The AI support system 1300 employs advanced algorithms and machine learning techniques to analyze the received patient information. By processing this data, the system generates a list of potential diagnoses that are relevant to the patient's condition. The potential diagnoses may be ranked based on their likelihood, and each diagnosis may be accompanied by supporting evidence or rationale.

To generate the potential diagnoses, the AI support system 1300 may utilize a variety of approaches. One possible method involves the use of deep learning models, such as convolutional neural networks (CNNs) or recurrent neural networks (RNNs), which are trained on large datasets of patient information. These models can extract relevant features from the input data and identify patterns that are indicative of specific diseases or conditions.

Alternatively, the AI support system 1300 may employ rule-based systems or expert systems that encapsulate medical knowledge and guidelines. These systems use predefined rules and decision trees to analyze patient information and generate potential diagnoses based on established medical criteria.

Another approach that the AI support system 1300 may utilize is case-based reasoning. In this method, the system compares the patient's information to a database of previous clinical cases and identifies similar cases to suggest potential diagnoses. The system may also incorporate natural language processing (NLP) techniques to extract relevant information from unstructured data, such as provider notes or patient narratives.

Once the AI support system 1300 has generated the list of potential diagnoses, this information is presented to the clinician through a user-friendly interface. The clinician can review the suggested diagnoses, along with the supporting evidence and rationale, to aid in their differential diagnosis process. The system may also provide recommendations for further tests or examinations to confirm or rule out specific diagnoses.

Throughout the diagnostic process, the AI support system 1300 can continuously learn and adapt based on the clinician's feedback and the outcomes of the patient cases. This feedback loop allows the system to refine its algorithms and improve its accuracy over time.

By leveraging the power of AI and machine learning, the AI support system 1300 can analyze vast amounts of patient data more efficiently than human providers. This enables the system to provide valuable insights and support to clinicians, ultimately leading to more accurate and timely diagnoses, as well as ensuring adherence to the standard of care.

In one embodiment, the AI support system 1300 is a key component of the AI Standard of Care Support system, designed to assist providers in making accurate and efficient diagnoses. At a high level, the AI support system 1300 obtains patient information from various sources and utilizes this data to generate one or more potential diagnoses for the patient.

The AI support system 1300 is capable of processing and analyzing a wide range of patient information, including patient-reported symptoms, provider notes, and sensor data. Patient-reported symptoms are subjective descriptions of the patient's health concerns, such as pain, discomfort, or any noticeable changes in bodily functions, provider notes include observations, findings, and assessments made by healthcare professionals during patient encounters. Sensor data can provide objective measurements of the patient's vital signs, such as heart rate, blood pressure, or oxygen saturation levels. Sensor data may comprise at least one of electrocardiogram, heart rate, blood glucose, blood oxygen percentage/saturation, body temperature, blood pressure, respiratory rate, respiratory volume, heart/lung/abdominal sounds, body fat, muscle tone, images and/or video of the ear/nose/throat, and images and/or video of the outer eye and skin and body temperature data.

The AI support system 1300 works by employing advanced machine learning algorithms and natural language processing techniques to analyze the provided patient information. These algorithms are trained on vast amounts of historical medical data, allowing the system to identify patterns, correlations, and anomalies that may indicate the presence of specific diseases or conditions. The system compares the patient's data with its extensive knowledge base, which includes information from medical literature, clinical guidelines, and expert opinions, to generate a list of potential diagnoses.

In some cases, the AI support system 1300 may utilize two or more types of patient information, such as a combination of patient-reported symptoms, provider notes, and sensor data, to generate more accurate and comprehensive potential diagnoses. By leveraging multiple data sources, the system can provide a more holistic view of the patient's health status and improve the reliability of its diagnostic suggestions.

The potential diagnoses generated by the AI support system 1300 may be presented as a ranked list to the clinician. This ranking is based on the likelihood or probability of each diagnosis being correct, given the available patient information. The ranked list allows the clinician to quickly identify the most probable diagnoses and prioritize their decision-making process accordingly.

Alternatives to the AI support system 1300 may include rule-based expert systems that rely on predefined decision trees or flowcharts to guide the diagnostic process. Another alternative is a case-based reasoning system, which compares the current patient's information to similar cases in its database to suggest potential diagnoses. Additionally, some systems may employ a hybrid approach, combining machine learning techniques with rule-based or case-based reasoning to generate diagnostic recommendations.

In one embodiment, user device(s) 110 is a computing device that can obtain patient and clinician input related to the health of a user. This device is designed to facilitate the collection of health-related data, which can be used to monitor the health status of a user, support clinical decision-making, or contribute to a larger dataset for analysis.

User device(s) 110 can be any type of computing device capable of receiving and processing input. This could include, but is not limited to, personal computers, laptops, tablets, or smartphones. The device may have an interface for user input, such as a keyboard, touchscreen, or voice recognition software. The input could be patient-reported symptoms, health history, lifestyle factors, or clinician observations and assessments.

The device processes the input data and can transmit it to other systems or devices for further analysis or action. For example, the data could be sent to a clinical decision support system, an electronic health record system, or a remote monitoring system. The device may also provide feedback to the user or clinician based on the input data, such as alerts, reminders, or recommendations.

In another embodiment, user device(s) 110 is a medical/consumer electronics device (e.g. such as medical/consumer electronics device 140 described above) equipped with a plurality of sensors to obtain patient information associated with the health of the patient. The sensors could measure various physiological parameters, such as heart rate, blood pressure, body temperature, blood glucose levels, or respiratory rate. The device could also include sensors for activity tracking, such as a pedometer or accelerometer.

The device collects sensor data continuously or at specified intervals, processes the data, and transmits it to other systems or devices. The data could be used for real-time monitoring of the patient's condition, triggering alerts if abnormal values are detected, or tracking trends over time. The device may also provide feedback to the patient based on the sensor data, such as health tips, progress reports, or motivational messages.

User device(s) 110 could be a standalone device, such as a smartwatch or fitness tracker, or it could be integrated into other devices, such as a smartphone or wearable device. The device could also be a medical device, such as a glucose meter or blood pressure monitor, with built-in connectivity features. The specific design and functionality of the device could vary depending on the intended use and user population.

User device(s) 110 include, generally, a computer or computing device including functionality for communicating (e.g., remotely) over a network 150. Data may be collected from user devices 110, and data requests may be initiated from each user device 110. User device(s) 110 may be a server, a desktop computer, a laptop computer, personal digital assistant (PDA), an in- or out-of-car navigation system, a smart phone or other cellular or mobile phone, or mobile gaming device, among other suitable computing devices. User devices 110 may execute one or more applications, such as a web browser (e.g., Microsoft Windows Internet Explorer, Mozilla Firefox, Apple Safari, Google Chrome, and Opera, etc.), or a dedicated application to submit user data, or to make prediction queries over a network 150.

In particular embodiments, each user device 110 may be an electronic device including hardware, software, or embedded logic components or a combination of two or more such components and capable of carrying out the appropriate functions implemented or supported by the user device 110. For example and without limitation, a user device 110 may be a desktop computer system, a notebook computer system, a netbook computer system, a handheld electronic device, or a mobile telephone. The present disclosure contemplates any user device 110. A user device 110 may enable a network user at the user device 110 to access network 150. A user device 110 may enable its user to communicate with other users at other user devices 110.

A user device 110 may have a web browser, such as MICROSOFT INTERNET EXPLORER, GOOGLE CHROME or MOZILLA FIREFOX, and may have one or more add-ons, plug-ins, or other extensions, such as TOOLBAR or YAHOO TOOLBAR. A user device 110 may enable a user to enter a Uniform Resource Locator (URL) or other address directing the web browser to a server, and the web browser may generate a Hyper Text Transfer Protocol (HTTP) request and communicate the HTTP request to server. The server may accept the HTTP request and communicate to the user device 110 one or more Hyper Text Markup Language (HTML) files responsive to the HTTP request. The user device 110 may render a web page based on the HTML files from server for presentation to the user. The present disclosure contemplates any suitable web page files. As an example and not by way of limitation, web pages may render from HTML files, Extensible Hyper Text Markup Language (XHTML) files, or Extensible Markup Language (XML) files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a web page encompasses one or more corresponding web page files (which a browser may use to render the web page) and vice versa, where appropriate.

The user device 110 may also include an application that is loaded onto the user device 110. The application obtains data from the network 150 and displays it to the user within the application interface.

Exemplary user devices are illustrated in some of the subsequent figures provided herein. This disclosure contemplates any suitable number of user devices, including computing systems taking any suitable physical form. As example and not by way of limitation, computing systems may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, or a combination of two or more of these. Where appropriate, the computing system may include one or more computer systems; be unitary or distributed; span multiple locations; span multiple machines; or reside in a cloud, which may include one or more cloud components in one or more networks. Where appropriate, one or more computing systems may perform without substantial spatial or temporal limitation one or more steps of one or more methods described or illustrated herein. As an example, and not by way of limitation, one or more computing systems may perform in real time or in batch mode one or more steps of one or more methods described or illustrated herein. One or more computing system may perform at different times or at different locations one or more steps of one or more methods described or illustrated herein, where appropriate.

Network cloud 150 generally represents a network or collection of networks (such as the Internet or a corporate intranet, or a combination of both) over which the various components illustrated in FIG. 1 (including other components that may be necessary to execute the system described herein, as would be readily understood to a person of ordinary skill in the art). In particular embodiments, network 150 is an intranet, an extranet, a virtual private network (VPN), a local area network (LAN), a wireless LAN (WLAN), a wide area network (WAN), a metropolitan area network (MAN), a portion of the Internet, or another network 150 or a combination of two or more such networks 150. One or more links connect the systems and databases described herein to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable network 150, and any suitable link for connecting the various systems and databases described herein.

The network 150 connects the various systems and computing devices described or referenced herein. In particular embodiments, network 150 is an intranet, an extranet, a virtual private network (VPN), a local area network (LAN), a wireless LAN (WLAN), a wide area network (WAN), a metropolitan area network (MAN), a portion of the Internet, or another network 421 or a combination of two or more such networks 150. The present disclosure contemplates any suitable network 150.

One or more links couple one or more systems, engines or devices to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable links coupling one or more systems, engines or devices to the network 150.

In particular embodiments, each system or engine may be a unitary server or may be a distributed server spanning multiple computers or multiple datacenters. Systems, engines, or modules may be of various types, such as, for example and without limitation, web server, news server, mail server, message server, advertising server, file server, application server, exchange server, database server, or proxy server. In particular embodiments, each system, engine or module may include hardware, software, or embedded logic components or a combination of two or more such components for carrying out the appropriate functionalities implemented or supported by their respective servers. For example, a web server is generally capable of hosting websites containing web pages or particular elements of web pages. More specifically, a web server may host HTML files or other file types, or may dynamically create or constitute files upon a request, and communicate them to client/user devices or other devices in response to HTTP or other requests from client devices or other devices. A mail server is generally capable of providing electronic mail services to various client devices or other devices. A database server is generally capable of providing an interface for managing data stored in one or more data stores.

In particular embodiments, one or more data storages may be communicatively linked to one or more servers via one or more links. In particular embodiments, data storages may be used to store various types of information. In particular embodiments, the information stored in data storages may be organized according to specific data structures. In particular embodiments, each data storage may be a relational database. Particular embodiments may provide interfaces that enable servers or clients to manage, e.g., retrieve, modify, add, or delete, the information stored in data storage.

The system may also contain other subsystems and databases, which are not illustrated in FIG. 1, but would be readily apparent to a person of ordinary skill in the art. For example, the system may include databases for storing data, storing features, storing outcomes (training sets), and storing models. Other databases and systems may be added or subtracted, as would be readily understood by a person of ordinary skill in the art, without departing from the scope of the invention.

Figure 14:
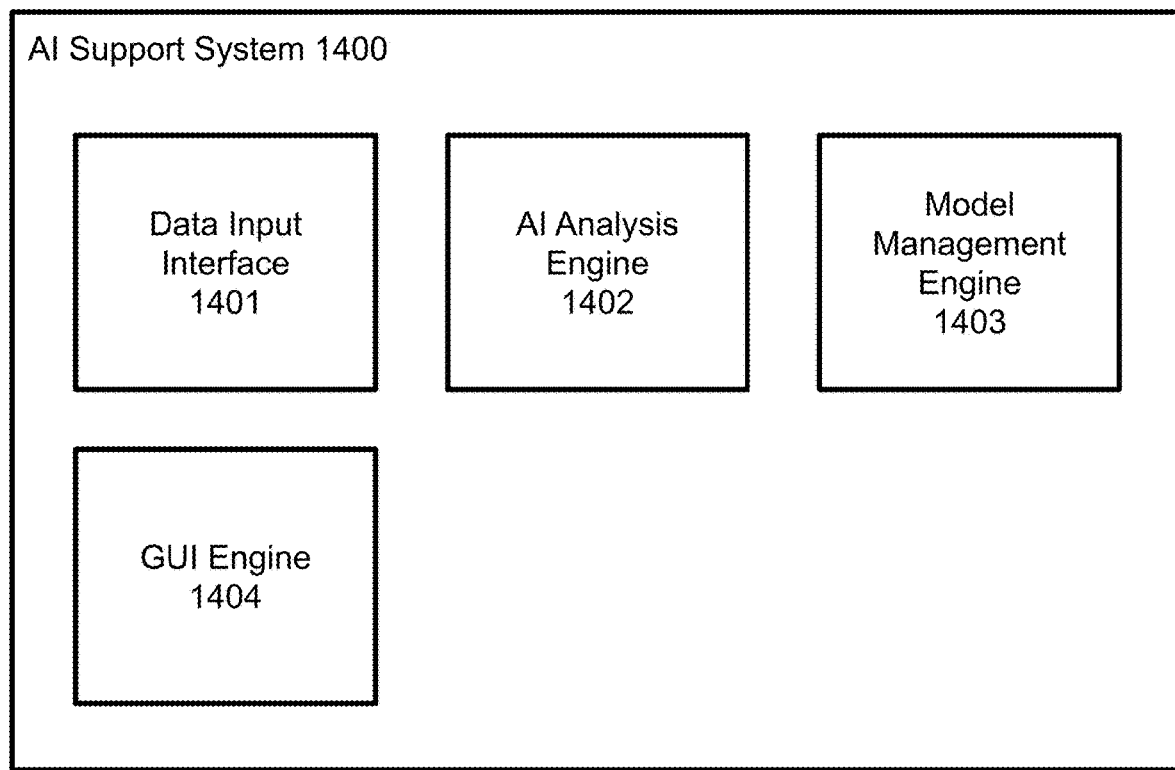
FIG. 14 illustrates an exemplary AI support system in accordance with an exemplary embodiment of the invention.

FIG. 14 illustrates an exemplary embodiment of an AI support system according to an embodiment of the invention. The system includes data input interface 1401, AI analysis engine 1402, model management engine 1403, and GUI engine 1404. The various components described herein are exemplary and for illustration purposes only and any combination or subcombination of the various components may be used as would be apparent to one of ordinary skill in the art. Other systems, interfaces, modules, engines, databases, and the like, may be used, as would be readily understood by a person of ordinary skill in the art, without departing from the scope of the invention. Any system, interface, module, engine, database, and the like may be divided into a plurality of such elements for achieving the same function without departing from the scope of the invention. Any system, interface, module, engine, database, and the like may be combined or consolidated into fewer of such elements for achieving the same function without departing from the scope of the invention. All functions of the components discussed herein may be initiated manually or may be automatically initiated when the criteria necessary to trigger action have been met.

As a general overview, the AI support system 1400 is designed to enhance provider diagnosis and ensure adherence to the standard of care by processing patient information obtained from user device(s) (e.g. user device(s) 160 and/or medical/consumer electronics device(s) 140). The user device(s) collect various forms of patient health data, which may include patient-reported symptoms, sensor data from medical devices, and electronic health records. This information is then transmitted to the AI support system 1400 for further analysis and generation of a list of potential diagnoses which are provided to a user device(s) associated with a provider for display and review by a provider.

In one embodiment, the data input interface 1401 is a component of the AI support system that facilitates communication between the system and user devices. The data input interface 1401 is responsible for receiving patient information and clinician feedback from user devices associated with patients and clinicians, respectively.

The data input interface 1401 may receive patient information from a user device associated with the patient. This patient information can include, but is not limited to, at least one of patient-reported symptoms, medical history, and data from wearable devices or sensors. The data input interface 1401 is designed to support various communication protocols and data formats, ensuring compatibility with a wide range of patient devices, such as smartphones, tablets, and wearable devices.

In addition to receiving patient information, the data input interface 1401 may also receive input from a user device associated with a clinician, such as a nurse or physician. This input can include patient information, such as provider notes or observations, as well as feedback on the AI system's performance, such as the appropriateness or suitability of the generated potential diagnoses and treatment recommendations.

The data input interface 1401 works by establishing a secure connection with the user devices, authenticating the users, and managing the data exchange process. It may employ various communication protocols, such as HTTP, HTTPS, or WebSocket, to ensure reliable and efficient data transmission. The data input interface 1401 may also implement data compression and encryption techniques to optimize data transfer and protect sensitive medical information.

Alternatives to the data input interface 1401 may include direct integration with electronic health record (EHR) systems, allowing the AI support system to access patient information and clinician notes directly from the EHR. Another alternative is the use of a web-based portal, where patients and clinicians can manually input information and feedback through a secure web interface. Additionally, the system may support the integration of third-party APIs, enabling seamless data exchange with external devices and platforms, such as wearable devices or telemedicine systems.

In one embodiment, the AI analysis engine 1402 is a subsystem designed to analyze patient information using at least one AI model to generate at least one potential diagnosis. This subsystem is a key component of the overall system, serving as the primary mechanism for processing and interpreting the health-related data collected from the user devices.

The AI analysis engine 1402 operates by receiving patient information, which could include a combination of patient-reported symptoms, clinician observations, sensor data from medical devices, and health records. This information is then processed using one or more AI models, which could be based on various AI techniques such as machine learning, deep learning, and/or natural language processing.

The AI model analyzes the patient information and generates a potential diagnosis based on patterns and correlations identified in the data. The model may consider a wide range of factors and their interrelationships, such as symptom combinations, disease prevalence, patient demographics, and medical history. The model's output is a potential diagnosis, or a set of potential diagnoses, each associated with a likelihood or confidence score.

The AI analysis engine 1402 also generates a ranked list of potential diagnoses. The ranking is typically based on the likelihood or confidence scores, with the most likely diagnosis ranked first. The ranked list provides a clear and concise summary of the AI model's output, facilitating interpretation and decision-making by the clinician such as aiding in the differential diagnosis process. In one aspect, each diagnosis may be accompanied by supporting evidence or rationale.

The AI analysis engine 1402 could be implemented using various AI platforms and technologies, and the specific AI model used could vary depending on the application. For example, a rule-based model could be used for simple diagnostic tasks, while a neural network could be used for more complex tasks involving large datasets and non-linear relationships. The engine could also incorporate multiple AI models, each specialized for a different type of data or task, and combine their outputs to generate the final diagnosis and ranking. In one aspect, the models may extract relevant features from the input data and identify patterns that are indicative of specific diseases or conditions.

Another approach that the AI analysis engine 1402 may utilize is case-based reasoning. In this method, the system compares the patient's information to a database of previous clinical cases and identifies similar cases to suggest potential diagnoses. The system may also incorporate natural language processing (NLP) techniques to extract relevant information from unstructured data, such as provider notes or patient narratives.

In one embodiment, the model management engine 1403 is a subsystem designed to update AI models, model parameters, and training data over time as more data becomes available. This subsystem is responsible for maintaining the performance and relevance of the AI models used in the system, ensuring that they continue to provide accurate and useful output as new data is collected and the underlying patterns and relationships potentially change.

The model management engine 1403 operates by monitoring the performance of the AI models and the availability of new data. When new data becomes available, such as additional patient information or provider feedback, the engine incorporates this data into the training dataset. The AI models are then retrained or fine-tuned using the updated dataset, resulting in updated model parameters. In one aspect, patient information and/or provider feedback may be received at a central server for use in updating the models. Patient information and/or provider feedback from a plurality of healthcare providers and/or patients may be aggregated at a central server. This aggregated data may be used to periodically update the at least one model or ensemble of models. The patient information and/or provider feedback may be transmitted to the central server using at least one of a de-identified format and data encryption to ensure security of the data transmission.

The engine also evaluates the performance of the AI models on an ongoing basis, using techniques such as cross-validation or out-of-sample testing. If the performance falls below a certain threshold, the engine triggers a model update process. This could involve retraining the existing model, selecting a different model, or adjusting the model parameters.

The model management engine 1403 also manages the versioning and deployment of the AI models. Each time a model is updated, a new version is created and stored. The engine ensures that the most recent and best-performing version of each model is deployed for use by the system.

There are various ways to implement the model management engine 1403. For example, it could be based on a rule-based system, where specific actions are triggered by predefined conditions. Alternatively, it could use a machine learning approach, where the engine learns from experience and adapts its behavior over time. The specific implementation could depend on factors such as the type of AI models used, the volume and velocity of the data, and the performance requirements of the system.

GUI engine 1404 is operable to generate one or more graphical user interfaces (GUIs) for at least one of obtaining patient information, presenting the AI analysis output, and receiving provider feedback. GUI engine 1404 may generate at least one GUI for displaying the ranked list of potential diagnoses and likelihood information. GUI engine 1404 may generate at least one GUI for receiving provider feedback related to the list of potential diagnoses. GUI engine 1404 may generate at least one GUI for obtaining patient information from at least one of a patient and a provider.

Figure 15:
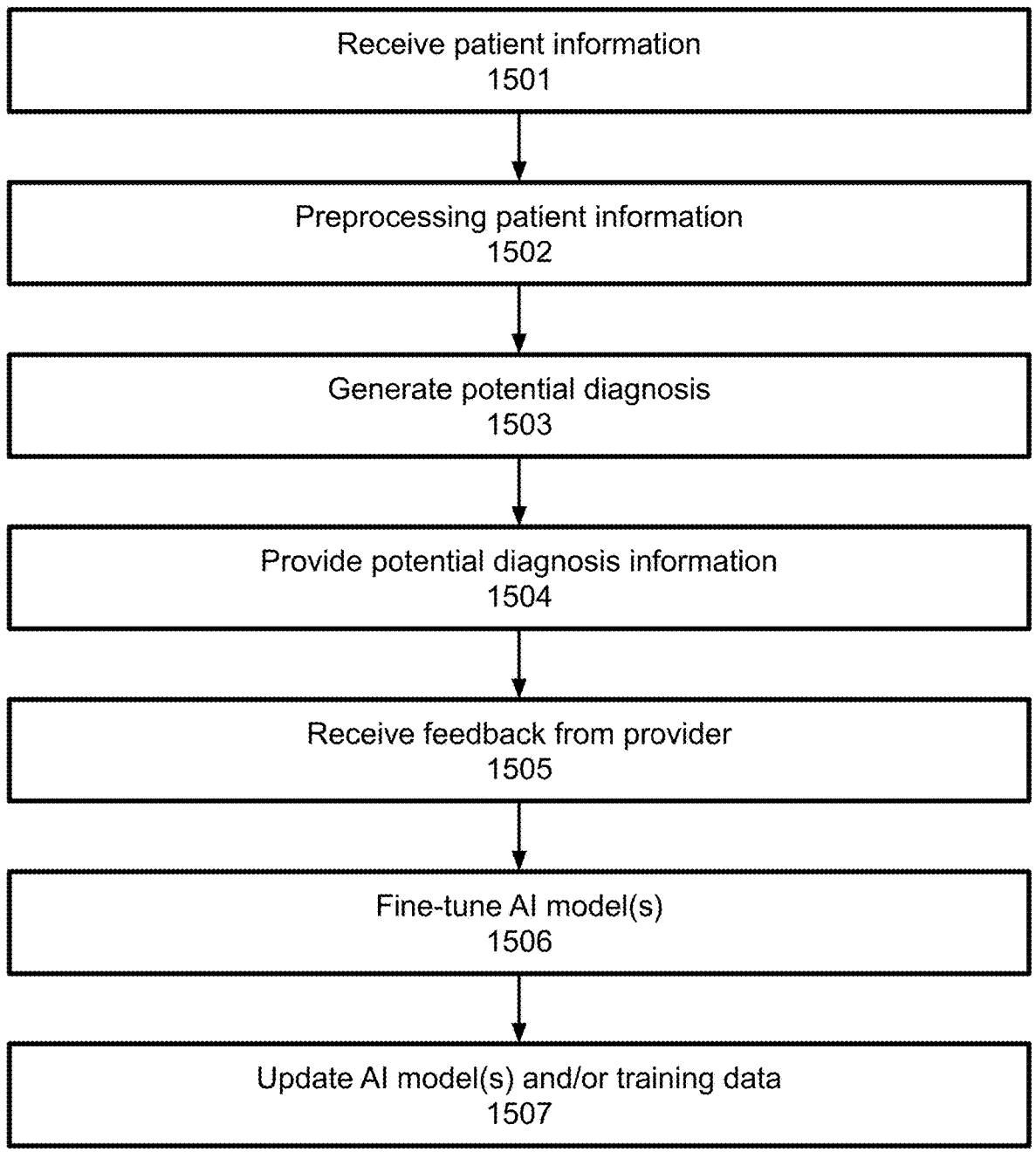
FIG. 15 illustrates an exemplary process for providing AI support for differential diagnosis and/or standard of care in accordance with an exemplary embodiment of the invention.

FIG. 15 illustrates an exemplary process for providing AI support for differential diagnosis and/or standard of care. The process may comprise receiving patient information 1501, preprocessing the patient information 1502, processing the preprocessed patient information to generate at least one potential diagnosis 1503, providing the potential diagnosis information 1504, receiving feedback from the provider 1505, fine-tuning the model 1506, updating the model and/or training data 1507. The process steps described herein may be performed in association with a system such as that described in FIGS. 1-3 and/or FIG. 13-14 above or in association with a different system. The process may comprise additional steps, fewer steps, and/or a different order of steps without departing from the scope of the invention as would be apparent to one of ordinary skill in the art.

In one embodiment, the process of receiving patient information 1501. This process may involve collecting various types of data related to the patient's health, which will be used as input for the AI system to generate potential diagnoses and treatment recommendations.

The patient information received in this process may comprise at least one of the following: patient-reported symptoms, provider notes, and sensor data from a medical device. Patient-reported symptoms are subjective descriptions of the patient's health concerns, such as pain, discomfort, or any noticeable changes in bodily functions. Provider notes include observations, findings, and assessments made by healthcare professionals during patient encounters. Sensor data from medical devices can provide objective measurements of the patient's vital signs, such as heart rate, blood pressure, or oxygen saturation levels. The patient information may be obtained as part of a telehealth interaction.

In some cases, the patient information may comprise two or more of the aforementioned data types, providing a more comprehensive view of the patient's health status. The sensor data from medical devices may be obtained in real-time, allowing for real-time sensor data to be factored into the AI analysis. In one aspect, real-time sensor data may allow for continuous monitoring and timely updates to the AI system. This real-time data acquisition is particularly useful for patients with chronic conditions or those requiring close monitoring. In one aspect, real-time sensor data may be continuously monitored for signs of patient deterioration. If deterioration is detected (e.g. sensor data exceeds or falls below certain thresholds, sensor data deviates from an expected trajectory, etc.), an alert may be generated and transmitted to alert a provider of the detected deterioration.

The sensor data may be obtained by a multi-sensor medical device, which can collect multiple types of physiological data simultaneously. Such devices may include wearable technology, such as smartwatches or patches, equipped with various sensors like accelerometers, gyroscopes, and photoplethysmography (PPG) sensors.

The medical device used for data collection may be a user device associated with the patient, such as a smartphone or tablet with built-in sensors or connected to external sensors. Alternatively, the medical device may be associated with a clinician, such as a nurse or physician, who uses it to collect patient data during a consultation or examination.

The process of receiving patient information 1501 may be performed locally on a user device, leveraging edge computing capabilities like AI on a chip. This approach allows for faster processing and reduced latency, as the data does not need to be transmitted to a remote server. Alternatively, the patient information may be received and processed by a server or cloud-based processing system, which can handle larger volumes of data and perform more complex computations.

In some scenarios, the patient information may be received as part of a telehealth consultation process, where the patient and healthcare provider communicate remotely using video conferencing or messaging platforms. This approach enables the collection of patient data without the need for an in-person visit.

Additionally, the patient information may further comprise medical history, such as data imported from electronic medical records (EMR) systems. This historical data can provide valuable context and insights into the patient's overall health, including past diagnoses, treatments, and outcomes.

Alternatives to the described process of receiving patient information 1501 may include manual data entry by healthcare professionals or patients themselves, using web-based forms or mobile applications. Another alternative is the use of natural language processing (NLP) techniques to extract relevant information from unstructured data sources, such as clinical notes or patient narratives.

In one embodiment, preprocessing the patient information 1502 is a software process designed to prepare the patient data for further analysis by the AI models. This process may involve extracting a set of features from the raw data and storing these features in a standardized format. Preprocessing the patient information may comprise at least one of identifying and correcting errors and inconsistencies in the patient information, normalizing numerical values to a common scale, and encoding categorical variables as binary vectors.

Preprocessing the patient information 1502 may operate by first receiving the raw patient data, which could include a variety of information such as patient-reported symptoms, clinician observations, sensor data from medical devices, and health records. The process then extracts a predefined set of features from this data. These features could be specific data points, statistical measures, or derived variables that are relevant for the AI models.

The extraction process could involve various operations, such as data cleaning, normalization, transformation, or dimensionality reduction. The specific operations and their sequence could depend on the nature of the data and the requirements of the AI models. The result of the extraction process is a set of features that represent the original data in a condensed and standardized form, suitable for input to the AI models.

The extracted features are then stored in a standardized format. This could be a database, a data file, or a data structure in memory. The standardized format ensures that the features are organized and accessible in a consistent manner, facilitating their use by the AI models and other parts of the system.

There are various ways to implement the preprocessing of patient information 1502. For example, the feature extraction could be based on a fixed schema, where the same set of features is extracted for all patients. Alternatively, it could be based on a dynamic schema, where the set of features is adapted for each patient based on their specific characteristics or conditions. The specific implementation could depend on factors such as the type of patient data, the complexity of the AI models, and the computational resources available.

In one embodiment, the processing of the patient information to generate at least one potential diagnoses 1503 is a software process designed to interpret the patient data and output a list of potential diagnoses. This process uses deep learning models to analyze the features extracted from the patient data and generate a list of potential diagnoses, each associated with a likelihood score and indicators of the rationale for its inclusion.

The process operates by first receiving the preprocessed patient information, which consists of a set of features extracted from the raw patient data. This information is then input to one or more deep learning models. The one or more deep learning models may comprise an ensemble of models. These models are trained to recognize patterns and correlations in the data that are indicative of various diagnoses. The one or more deep learning models may comprise at least one of a convolutional neural network, a recurrent neural network, and a transformer model. In one aspect, the convolutional neural network may be operable to process image data, the recurrent neural network operable to process time-series data, and the transformer model operable to process unstructured text data Each model in the ensemble may be specialized for a specific type of data or diagnosis. For example, one model may be trained on data associated with cardiovascular conditions, while another model may be trained on data associated with neurological conditions. The output of each model is a potential diagnosis, or a set of potential diagnoses, each associated with a likelihood score.

The process also generates indicators for each potential diagnosis. These indicators provide insight into the reason or rationale for the inclusion of the diagnosis in the list. They could be based on the key features or patterns that contributed to the diagnosis, providing transparency and interpretability to the output of the AI models.

The list of potential diagnoses is then ranked based on the likelihood scores, with the most likely diagnosis ranked first.

The ranked list, along with the associated likelihood scores and indicators, provides a comprehensive and interpretable summary of the AI models' output.

There are various ways to implement the process of preprocessed patient information to generate potential diagnoses 1503. For example, the deep learning models could be based on different architectures, such as convolutional neural networks for image data or recurrent neural networks for time series data. The models could also be trained using different algorithms, such as gradient descent or genetic algorithms. The specific implementation could depend on factors such as the type and complexity of the patient data, the requirements for accuracy and interpretability, and the computational resources available.

In one embodiment, the software process of providing the potential diagnosis information 1504 is designed to communicate the results of the AI analysis to the provider in an effective and interpretable manner. This process involves presenting the ranked list of potential diagnoses, the likelihood scores for each diagnosis, and/or a visualization of the key factors contributing to each diagnosis.

The process operates by first generating the output from the AI analysis engine, which includes a ranked list of potential diagnoses based on their likelihood scores. Each diagnosis in the list may also be associated with indicators or key factors that contributed to its inclusion in the list, providing insight into the rationale behind each potential diagnosis.

This information is then presented to the provider through an interactive user interface. The interface is designed to allow the provider to easily understand and interpret the AI's findings. The ranked list of potential diagnoses provides a clear overview of the most likely conditions, while the likelihood scores quantify the AI's confidence in each diagnosis. The visualization of key factors offers a deeper understanding of the data and reasoning behind each potential diagnosis, enabling the provider to make informed decisions about further diagnostic tests or treatments. In one aspect, the visualization of key factors may be displayed as an attention map highlighting the most relevant features of the patient information for each diagnosis.

Alternatives to presenting the potential diagnosis information could include various forms of visualization techniques, such as charts, graphs, or heat maps, to represent the data in a more intuitive way. Additionally, the interface could be customizable, allowing providers to adjust the level of detail or the format of the information according to their preferences or needs. In one aspect, the interactive user interface is operable to allow the provider to adjust the likelihood score threshold for displaying potential diagnoses such that only diagnoses meeting the threshold are displayed. In one aspect, the interactive user interface allows the provider to at least one of manually add, remove, upvote, and downvote diagnoses from the ranked list. This input from the provider may be used for at least one of system training, efficiency evaluation, and standard of care determination purposes.

The interactive user interface could be implemented as a web-based application, a standalone software application, or integrated into an existing electronic health record (EHR) system. The choice of implementation could depend on factors such as compatibility with the provider's workflow, the technological infrastructure of the healthcare facility, and the need for integration with other healthcare IT systems.

This process of providing potential diagnosis information aims to bridge the gap between the complex analysis performed by the AI models and the practical needs of the provider, facilitating a more efficient and informed diagnostic process.

In one aspect, the process may further comprise retrieving (e.g. from a database), for each potential diagnosis, a set of recommended next steps based on a dynamically updated standard of care knowledge base. The recommended next steps may be prioritized based on patient-specific factors and/or the likelihood scores of the potential diagnoses. The recommended next steps may be provided to the provider via the interactive user interface.

In one embodiment, the software process of receiving feedback from the provider 1505 is designed to collect and incorporate the provider's professional evaluation regarding the appropriateness or suitability of the potential diagnoses provided by the AI system. This process allows the provider to offer additional insights, impressions, or corrections based on their expertise and the specific context of the patient's condition.

The process operates by presenting the provider with an interface through which they can review the potential diagnoses and the associated information provided by the AI system. The provider can then input their feedback on each diagnosis. This feedback may indicate whether a diagnosis is considered appropriate or suitable, and it may include additional insights or impressions that could provide context, suggest alternative diagnoses, or highlight factors that the AI might have overlooked or misinterpreted.

The feedback is captured and processed by the system. It may be used immediately to adjust the presentation of diagnoses for the current case or stored for future analysis. Over time, the collected feedback can be used to train or fine-tune the AI models, improving their accuracy and relevance. This continuous learning loop enhances the system's performance and ensures that it adapts to the evolving knowledge and practices in the medical field.

Alternatives to the direct input of feedback could include the use of structured forms or checklists that standardize the feedback process, making it easier to analyze and incorporate into the AI system. Another alternative could be the integration of natural language processing (NLP) capabilities, allowing providers to provide feedback in free text, which the system can then interpret and categorize automatically.

The feedback process could be implemented as part of the existing user interface for reviewing potential diagnoses or as a separate module within the system. The choice of implementation may depend on factors such as the desired level of integration with the diagnostic review process, the complexity of the feedback being collected, and the preferences of the user base.

By incorporating provider feedback into the diagnostic process, the software process of receiving feedback from the provider 1505 ensures that the AI system remains aligned with clinical practice and continues to provide valuable support to healthcare professionals.

In one embodiment, the software process of fine-tuning the model 1506 involves adjusting the parameters of the deep learning model used to generate potential diagnoses. This fine-tuning is based on new patient information received and feedback provided by providers regarding the appropriateness or suitability of the potential diagnoses previously generated. The objective is to improve the model's accuracy and reliability in diagnosing patient conditions.

The fine-tuning process works by first identifying aspects of the model that could benefit from adjustment. This could involve analyzing the model's performance in light of the latest patient data and provider feedback to pinpoint inaccuracies or areas of uncertainty. Based on this analysis, the model's parameters are adjusted to better reflect the patterns and relationships present in the updated dataset. This could include modifying weights within the neural network, changing the architecture of the model, or updating the training algorithm.

One approach to fine-tuning the model involves using a reinforcement learning strategy. In this approach, the model is treated as an agent that learns from interactions with an environment—in this case, the dataset of patient information and provider feedback. The model makes predictions (actions) based on the data (state), and adjustments are made based on the feedback (reward). Over time, the model learns to make more accurate predictions by maximizing the rewards it receives, which correspond to positive feedback from providers and alignment with actual patient diagnoses. In one aspect, the reinforcement learning comprises at least one of defining a reward function based on at least one of the appropriateness of the potential diagnoses and the efficiency of the diagnostic process, exploring alternative diagnostic strategies by perturbing the inputs to the at least one deep learning model, and updating the model parameters to maximize the expected cumulative reward over time.

Alternatives to reinforcement learning for fine-tuning the model could include supervised learning, where the model is retrained on a dataset that has been updated with new patient information and annotated with correct diagnoses based on provider feedback. Another alternative could be unsupervised learning, where the model adjusts itself by identifying patterns and anomalies in the data without explicit guidance on the correct diagnoses.

The fine-tuning process could be implemented as a continuous, automated procedure that occurs at regular intervals, or it could be initiated manually in response to significant updates to the dataset or feedback from users. The choice of implementation may depend on factors such as the volume and velocity of new data and feedback, the computational resources available, and the desired balance between model stability and adaptability.

By fine-tuning the model based on the latest data and feedback, the software process of fine-tuning the model 1506 ensures that the AI system remains up-to-date and aligned with current medical knowledge and practices, thereby enhancing its utility and effectiveness in supporting healthcare professionals.

In one embodiment, the software process of updating the model and/or training data 1507 involves modifying the parameters of at least one deep learning model and refreshing the dataset used for training these models. This update is based on insights gained from the fine-tuning process, incorporating new patient information and provider feedback to enhance the model's diagnostic capabilities.

The process begins with the collection of new data, which may include recent patient information and feedback from providers on the diagnoses suggested by the model. This new data is then preprocessed to extract relevant features and standardized to align with the existing training dataset. The updated dataset includes this new information, enriching the diversity and volume of data available for training the deep learning models.

Following the data update, the model parameters are adjusted. This adjustment is informed by the outcomes of the fine-tuning process, which identifies the model's strengths and areas for improvement. The parameters might be updated to reflect new insights into disease patterns, symptom correlations, or other diagnostic factors highlighted by recent data and feedback.

One approach to updating the model involves retraining the deep learning model with the enriched training dataset. This retraining process allows the model to learn from the expanded dataset, incorporating the latest patient information and provider insights into its diagnostic predictions.

Alternatives to retraining include incremental learning, where the model is updated with new data without retraining from scratch, and transfer learning, where a pre-trained model is adapted to the updated dataset with minimal changes to its structure. These alternatives can offer efficiencies in terms of computational resources and time, especially when dealing with large datasets or complex models.

The updated model and training data are then validated to ensure that the updates have improved the model's performance. This validation can involve techniques such as cross-validation or using a separate test dataset to assess the model's accuracy and reliability in predicting diagnoses.

By regularly updating the model and training data, the software process of updating the model and/or training data 1507 ensures that the deep learning models remain effective and relevant, leveraging the latest available information and feedback to support accurate and timely diagnoses.

Figure 16:
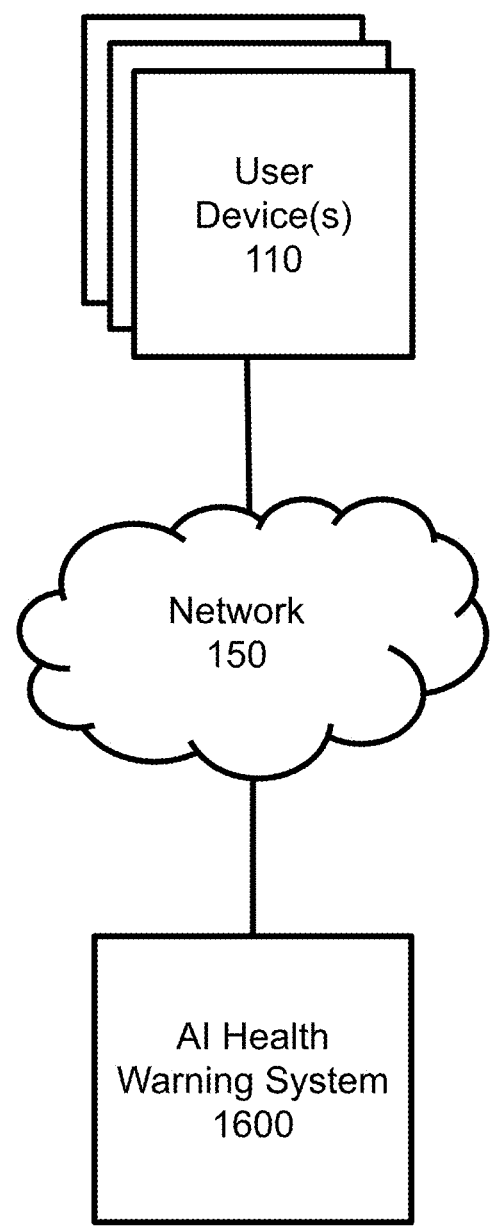
FIG. 16 illustrates exemplary systems and methods for artificial intelligence based health warning in accordance with an exemplary embodiment of the invention.

FIG. 16 illustrates an exemplary embodiment of systems and methods for artificial intelligence standard of care support according to one embodiment. The system includes user device(s) 110, AI health warning system 1600, and a network 150 over which the various systems communicate and interact. The various components described herein are exemplary and for illustration purposes only and any combination or subcombination of the various components may be used as would be apparent to one of ordinary skill in the art. The system may be reorganized or consolidated, as understood by a person of ordinary skill in the art, to perform the same tasks on one or more other servers or computing devices without departing from the scope of the invention.

As a general overview, AI health warning system 1600 obtains user health information comprised of at least real-time sensor data associated with a physiological characteristic of the user. AI system 1600 processes the sensor data using at least one machine learning model to generate a health assessment and/or health indicator. AI warning system may provide the health assessment and/or indicator to the user via user interface. AI warning system may provide action steps based on the health indicator.

In one embodiment, the AI health warning system 1600 is designed to enhance detection of potential health concerns by processing user health information obtained from user device(s) 110. The user device(s) 110 collect various forms of health data, which may include user-reported symptoms, sensor data from medical devices, and electronic health records. This information is then transmitted to the AI health warning system 1600 for further analysis. The user device(s) 110 may comprise user devices 160 and/or medical/consumer electronics devices 140 as described in at least FIG. 1 above.

The AI health warning system 1600 employs advanced algorithms and machine learning techniques to analyze the received user information. By processing this data, the system is operable to identify at least one of a measure and a pattern indicative of a potential health concern. A potential concern may comprise a measurement that is out of an expected range or above or below an expected threshold. A potential concern may comprise a measurement that has deviated by a threshold amount from an expected value, such as a baseline measure associated with the user.

To generate the potential concerns, the AI health warning system 1600 may utilize a variety of approaches. One possible method involves the use of deep learning models, such as convolutional neural networks (CNNs) or recurrent neural networks (RNNs), which are trained on large datasets of user information. These models can extract relevant features from the input data and identify patterns that are abnormal and/or indicative of specific diseases or conditions.

Alternatively, the AI health warning system 1600 may employ rule-based systems or expert systems that encapsulate medical knowledge and guidelines. These systems use predefined rules and decision trees to analyze user information and generate potential health concerns based on established medical criteria.

Another approach that the AI health warning system 1600 may utilize is case-based reasoning. In this method, the system compares the user's information to a database of previous clinical cases and identifies similar cases to suggest potential concerns. The system may also incorporate natural language processing (NLP) techniques to extract relevant information from unstructured data, such as provider notes, medical history, or user provided information.

Over time the AI health warning system 1600 can continuously learn and adapt to the user based on at least one of gathered user information, health assessment and indicators identified, and outcomes associated with previously generated warnings for the user. This feedback loop allows the system to refine its algorithms and improve its accuracy over time.

By leveraging the power of AI and machine learning, the AI health warning system 1600 can analyze vast amounts of health data more efficiently than human providers. This enables the system to provide valuable insights into user health trends and allow for early warning of potential concerns, ultimately leading to more timely diagnoses and/or treatments.

The AI health warning system 1600 is capable of processing and analyzing a wide range of user information, including user-reported symptoms, provider notes, and sensor data. User-reported symptoms are subjective descriptions of the user's health concerns, such as pain, discomfort, or any noticeable changes in bodily functions. Provider notes include observations, findings, and assessments made by healthcare professionals during user encounters. Sensor data can provide objective measurements of the user's vital signs, such as heart rate, blood pressure, or oxygen saturation levels. Sensor data may comprise at least one of electrocardiogram, heart rate, blood glucose, blood oxygen percentage/saturation, body temperature, blood pressure, respiratory rate, respiratory volume, heart/lung/abdominal sounds, body fat, muscle tone, images and/or video of the ear/nose/throat, and images and/or video of the outer eye and skin and body temperature data.

The AI health warning system 1600 works by employing advanced machine learning algorithms and natural language processing techniques to analyze the provided user information. These algorithms may be trained on vast amounts of historical medical data, allowing the system to identify patterns, correlations, and anomalies that may indicate the presence of specific diseases or conditions. The system compares the user's data with its extensive knowledge base, which includes information from medical literature, clinical guidelines, and expert opinions, to generate a list of potential concerns.

In some cases, the AI health warning system 1600 may utilize two or more types of user information, such as a combination of user-reported symptoms, provider notes, and sensor data, to generate more accurate and comprehensive potential concerns. By leveraging multiple data sources, the system can provide a more holistic view of the user's health status and improve the reliability of its warning indicators.

Alternatives to the AI health warning system 1600 may include rule-based expert systems that rely on predefined decision trees or flowcharts to guide the analytic process. Another alternative is a case-based reasoning system, which compares the current user's information to similar cases in its database to suggest potential concerns. Additionally, some systems may employ a hybrid approach, combining machine learning techniques with rule-based or case-based reasoning to generate potential concerns and corresponding warnings.

In one embodiment, user device(s) 110 is a computing device that can obtain user and clinician input related to the health of a user. This device is designed to facilitate the collection of health-related data, which can be used to monitor the health status of a user, identify potential health concerns, and/or contribute to a larger dataset for analysis.

User device(s) 110 can be any type of computing device capable of receiving and processing input. This could include, but is not limited to, personal computers, laptops, tablets, or smartphones. The device may have an interface for user input, such as a keyboard, touchscreen, or voice recognition software. The input could be user-reported symptoms, health history, lifestyle factors, or clinician observations and assessments.

The device processes the input data and can transmit it to other systems or devices for further analysis or action. For example, the data could be sent to a clinical decision support system, an electronic health record system, or a remote monitoring system. The device may also provide feedback to the user or clinician based on the input data, such as alerts, reminders, or recommendations.

In another embodiment, user device(s) 110 is a medical/consumer electronics device (e.g. such as medical/consumer electronics device 140 described above) equipped with a plurality of sensors to obtain user information associated with the health of the user. The sensors could measure various physiological parameters, such as heart rate, blood pressure, body temperature, blood glucose levels, or respiratory rate. The device could also include sensors for activity tracking, such as a pedometer or accelerometer.

The device collects sensor data continuously or at specified intervals, processes the data, and transmits it to other systems or devices. The data could be used for real-time monitoring of the user's condition, triggering alerts if abnormal values are detected, or tracking trends over time. The device may also provide feedback to the user based on the sensor data, such as health tips, progress reports, or motivational messages.

User device(s) 110 could be a standalone device, such as a smartwatch or fitness tracker, or it could be integrated into other devices, such as a smartphone or wearable device. The device could also be a medical device, such as a glucose meter or blood pressure monitor, with built-in connectivity features. The specific design and functionality of the device could vary depending on the intended use and user population.

User device(s) 110 include, generally, a computer or computing device including functionality for communicating (e.g., remotely) over a network 150. Data may be collected from user devices 110, and data requests may be initiated from each user device 110. User device(s) 110 may be a server, a desktop computer, a laptop computer, personal digital assistant (PDA), an in- or out-of-car navigation system, a smart phone or other cellular or mobile phone, or mobile gaming device, among other suitable computing devices. User devices 110 may execute one or more applications, such as a web browser (e.g., Microsoft Windows Internet Explorer, Mozilla Firefox, Apple Safari, Google Chrome, and Opera, etc.), or a dedicated application to submit user data, or to make prediction queries over a network 150.

In particular embodiments, each user device 110 may be an electronic device including hardware, software, or embedded logic components or a combination of two or more such components and capable of carrying out the appropriate functions implemented or supported by the user device 110. For example and without limitation, a user device 110 may be a desktop computer system, a notebook computer system, a netbook computer system, a handheld electronic device, or a mobile telephone. The present disclosure contemplates any user device 110. A user device 110 may enable a network user at the user device 110 to access network 150. A user device 110 may enable its user to communicate with other users at other user devices 110.

A user device 110 may have a web browser, such as MICROSOFT INTERNET EXPLORER, GOOGLE CHROME or MOZILLA FIREFOX, and may have one or more add-ons, plug-ins, or other extensions, such as TOOLBAR or YAHOO TOOLBAR. A user device 110 may enable a user to enter a Uniform Resource Locator (URL) or other address directing the web browser to a server, and the web browser may generate a Hyper Text Transfer Protocol (HTTP) request and communicate the HTTP request to server. The server may accept the HTTP request and communicate to the user device 110 one or more Hyper Text Markup Language (HTML) files responsive to the HTTP request. The user device 110 may render a web page based on the HTML files from server for presentation to the user. The present disclosure contemplates any suitable web page files. As an example and not by way of limitation, web pages may render from HTML files, Extensible Hyper Text Markup Language (XHTML) files, or Extensible Markup Language (XML) files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a web page encompasses one or more corresponding web page files (which a browser may use to render the web page) and vice versa, where appropriate.

The user device 110 may also include an application that is loaded onto the user device 110. The application obtains data from the network 150 and displays it to the user within the application interface.

Exemplary user devices are illustrated in some of the subsequent figures provided herein. This disclosure contemplates any suitable number of user devices, including computing systems taking any suitable physical form. As example and not by way of limitation, computing systems may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, or a combination of two or more of these. Where appropriate, the computing system may include one or more computer systems; be unitary or distributed; span multiple locations; span multiple machines; or reside in a cloud, which may include one or more cloud components in one or more networks. Where appropriate, one or more computing systems may perform without substantial spatial or temporal limitation one or more steps of one or more methods described or illustrated herein. As an example, and not by way of limitation, one or more computing systems may perform in real time or in batch mode one or more steps of one or more methods described or illustrated herein. One or more computing system may perform at different times or at different locations one or more steps of one or more methods described or illustrated herein, where appropriate.

Network cloud 150 generally represents a network or collection of networks (such as the Internet or a corporate intranet, or a combination of both) over which the various components illustrated in FIG. 1 (including other components that may be necessary to execute the system described herein, as would be readily understood to a person of ordinary skill in the art). In particular embodiments, network 150 is an intranet, an extranet, a virtual private network (VPN), a local area network (LAN), a wireless LAN (WLAN), a wide area network (WAN), a metropolitan area network (MAN), a portion of the Internet, or another network 150 or a combination of two or more such networks 150. One or more links connect the systems and databases described herein to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable network 150, and any suitable link for connecting the various systems and databases described herein.

The network 150 connects the various systems and computing devices described or referenced herein. In particular embodiments, network 150 is an intranet, an extranet, a virtual private network (VPN), a local area network (LAN), a wireless LAN (WLAN), a wide area network (WAN), a metropolitan area network (MAN), a portion of the Internet, or another network 421 or a combination of two or more such networks 150. The present disclosure contemplates any suitable network 150.

One or more links couple one or more systems, engines or devices to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable links coupling one or more systems, engines or devices to the network 150.

In particular embodiments, each system or engine may be a unitary server or may be a distributed server spanning multiple computers or multiple datacenters. Systems, engines, or modules may be of various types, such as, for example and without limitation, web server, news server, mail server, message server, advertising server, file server, application server, exchange server, database server, or proxy server. In particular embodiments, each system, engine or module may include hardware, software, or embedded logic components or a combination of two or more such components for carrying out the appropriate functionalities implemented or supported by their respective servers. For example, a web server is generally capable of hosting websites containing web pages or particular elements of web pages. More specifically, a web server may host HTML files or other file types, or may dynamically create or constitute files upon a request, and communicate them to client/user devices or other devices in response to HTTP or other requests from client devices or other devices. A mail server is generally capable of providing electronic mail services to various client devices or other devices. A database server is generally capable of providing an interface for managing data stored in one or more data stores.

In particular embodiments, one or more data storages may be communicatively linked to one or more servers via one or more links. In particular embodiments, data storages may be used to store various types of information. In particular embodiments, the information stored in data storages may be organized according to specific data structures. In particular embodiments, each data storage may be a relational database. Particular embodiments may provide interfaces that enable servers or clients to manage, e.g., retrieve, modify, add, or delete, the information stored in data storage.

The system may also contain other subsystems and databases, which are not illustrated in FIG. 1, but would be readily apparent to a person of ordinary skill in the art. For example, the system may include databases for storing data, storing features, storing outcomes (training sets), and storing models. Other databases and systems may be added or subtracted, as would be readily understood by a person of ordinary skill in the art, without departing from the scope of the invention.

Figure 17:
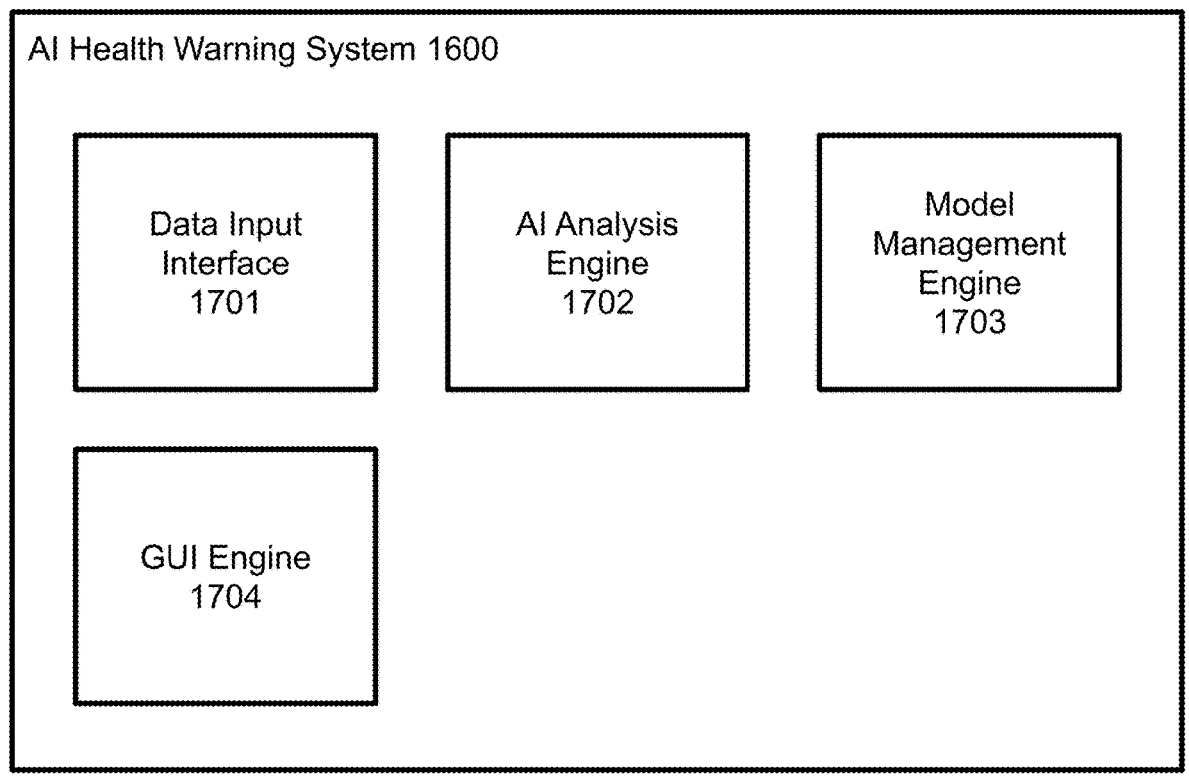
FIG. 17 illustrates an exemplary AI health warning system in accordance with an exemplary embodiment of the invention.

FIG. 17 illustrates an exemplary embodiment of an AI health warning system according to an embodiment of the invention. The system includes data input interface 1701, AI analysis engine 1702, model management engine 1703, and GUI engine 1704. The various components described herein are exemplary and for illustration purposes only and any combination or subcombination of the various components may be used as would be apparent to one of ordinary skill in the art. Other systems, interfaces, modules, engines, databases, and the like, may be used, as would be readily understood by a person of ordinary skill in the art, without departing from the scope of the invention. Any system, interface, module, engine, database, and the like may be divided into a plurality of such elements for achieving the same function without departing from the scope of the invention. Any system, interface, module, engine, database, and the like may be combined or consolidated into fewer of such elements for achieving the same function without departing from the scope of the invention. All functions of the components discussed herein may be initiated manually or may be automatically initiated when the criteria necessary to trigger action have been met.

As a general overview, the AI health warning system 1600 is designed to detect potential health concerns and alert users by processing user information obtained from user device(s) (e.g. user device(s) 160 and/or medical/consumer electronics device(s) 140). The user device(s) collect various forms of user health data, which may include user-reported symptoms, sensor data from medical devices, and electronic health records. This information is then transmitted to the AI health warning system 1600 for further analysis and generation of at least one of a health assessment and health indicator and provide a warning to the user device(s) when a potential health concern is identified.

In one embodiment, the data input interface 1701 is a component of the AI health warning system that facilitates communication between the system and user devices. The data input interface 1701 is responsible for receiving user information and optionally clinician input.

The data input interface 1701 may receive user information from a user device associated with the user. This user information can include, but is not limited to, at least one of user-reported symptoms, medical history, and data from wearable devices or sensors. The data input interface 1701 is designed to support various communication protocols and data formats, ensuring compatibility with a wide range of user devices, such as smartphones, tablets, and wearable devices.

In addition to receiving user information, the data input interface 1701 may also receive input from a database, such as medical history/records, provider notes or observations, as well as feedback on the AI system's performance, such as information associated with outcomes corresponding to previously generated warnings. Such outcome information may indicate an appropriateness or suitability of the generated potential concern and corresponding warning.

The data input interface 1701 works by establishing a secure connection with the user devices, authenticating the users, and managing the data exchange process. It may employ various communication protocols, such as HTTP, HTTPS, or WebSocket, to ensure reliable and efficient data transmission. The data input interface 1701 may also implement data compression and encryption techniques to optimize data transfer and protect sensitive medical information.

Alternatives to the data input interface 1701 may include direct integration with electronic health record (EHR) systems, allowing the AI health warning system to access user information directly from the EHR. Another alternative is the use of a web-based portal, where users and clinicians can manually input information and feedback through a secure web interface. Additionally, the system may support the integration of third-party APIs, enabling seamless data exchange with external devices and platforms, such as wearable devices or telemedicine systems.

In one embodiment, the AI analysis engine 1702 is a subsystem designed to analyze user information using at least one AI model to generate at least one potential concern, if a concern is identified. This subsystem is a key component of the overall system, serving as the primary mechanism for processing and interpreting the health-related data collected from the user devices.

The AI analysis engine 1702 operates by receiving user information, which could include a combination of user-reported symptoms, sensor data from medical devices, and health records. This information is then processed using one or more AI models, which could be based on various AI techniques such as machine learning, deep learning, and/or natural language processing.

The AI model analyzes the user information and generates a potential concern based on patterns and correlations identified in the data. The model may consider a wide range of factors and their interrelationships, such as symptom combinations, disease prevalence, user demographics, and medical history. The model's output is a potential concern, or a set of potential concerns, each of which may be associated with a likelihood or confidence score. The model may consider user-specific factors and generate user-specific criteria for indicating a potential concern.

The AI analysis engine 1702 could be implemented using various AI platforms and technologies, and the specific AI model used could vary depending on the application. For example, a rule-based model could be used for simple evaluation tasks, while a neural network could be used for more complex tasks involving large datasets and non-linear relationships. The engine could also incorporate multiple AI models, each specialized for a different type of data or task, and combine their outputs to generate the final potential concern. In one aspect, the models may extract relevant features from the input data and identify patterns that are indicative of potential concerns and/or specific diseases or conditions.

Another approach that the AI analysis engine 1702 may utilize is case-based reasoning. In this method, the system compares the user's information to a database of previous clinical cases and identifies similar cases to suggest potential concerns. The system may also incorporate natural language processing (NLP) techniques to extract relevant information from unstructured data, such as certain electronic health records (e.g. provider notes) or user narratives describing their condition.

In one embodiment, the model management engine 1703 is a subsystem designed to update AI models, model parameters, and training data over time as more data becomes available. This subsystem is responsible for maintaining the performance and relevance of the AI models used in the system, ensuring that they continue to provide accurate and useful output as new data is collected and the underlying patterns and relationships potentially change. In one aspect, model management engine updates a local model over time to generate a user specific model that learns from ongoing data collection and/or outcomes.

The model management engine 1703 operates by monitoring the performance of the AI models and the availability of new data. When new data becomes available, such as additional user information or outcome/warning feedback, the engine incorporates this data into the training dataset. The AI models are then retrained or fine-tuned using the updated dataset, resulting in updated model parameters. In one aspect, user information and/or warning/outcome data may be received at a central server for use in updating the models. User information and/or from a plurality of users may be aggregated at a central server. This aggregated data may be used to periodically update a central model or ensemble of models. The user information and/or provider feedback may be transmitted to the central server using at least one of a de-identified format and data encryption to ensure security of the data transmission.

The engine also evaluates the performance of the AI models on an ongoing basis, using techniques such as cross-validation or out-of-sample testing. If the performance falls below a certain threshold, the engine triggers a model update process. This could involve retraining the existing model, selecting a different model, or adjusting the model parameters.

The model management engine 1703 also manages the versioning and deployment of the AI models. Each time a model is updated, a new version is created and stored. The engine ensures that the most recent and best-performing version of each model is deployed for use by the system.

There are various ways to implement the model management engine 1703. For example, it could be based on a rule-based system, where specific actions are triggered by predefined conditions. Alternatively, it could use a machine learning approach, where the engine learns from experience and adapts its behavior over time. The specific implementation could depend on factors such as the type of AI models used, the volume and velocity of the data, and the performance requirements of the system.

GUI engine 1704 is operable to generate one or more graphical user interfaces (GUIs) for at least one of obtaining user information and presenting at least one of the AI analysis output, a warning and action steps. GUI engine 1704 may generate at least one GUI for displaying the potential concern information, warning information and/or action step(s).

Figure 18:
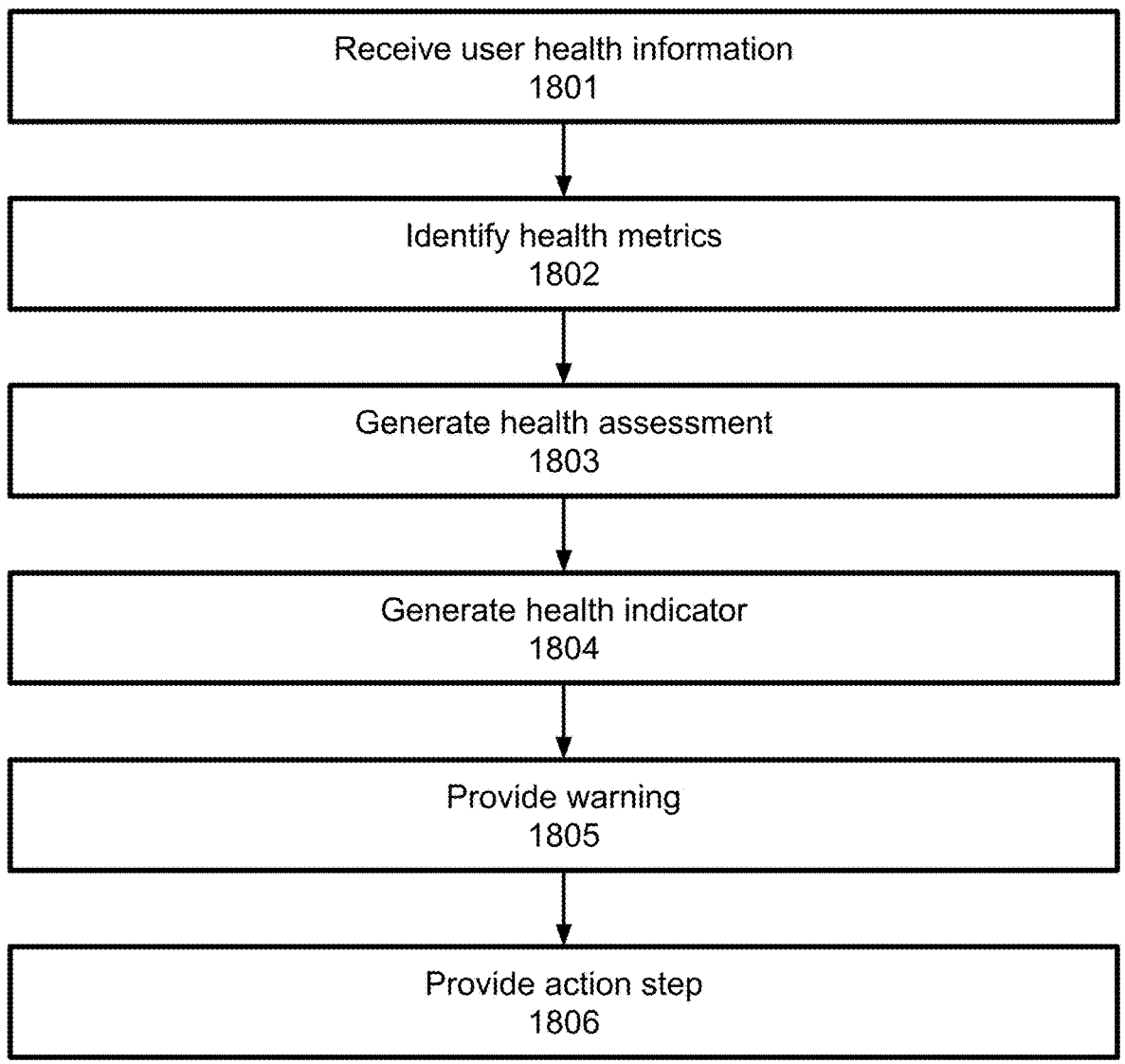
FIG. 18 illustrates an exemplary process for providing AI based warnings of potential health concerns.

FIG. 18 illustrates an exemplary process for providing AI based warnings of potential health concerns. The process may comprise receiving user health information 1801, identifying health metric(s) 1802, generate health assessment 1803, generate health indicator 1804, provide warning 1805, and provide action step 1806. The process steps described herein may be performed in association with a system such as that described in FIGS. 1-3 and/or FIG. 16-17 above or in association with a different system. The process may comprise additional steps, fewer steps, and/or a different order of steps without departing from the scope of the invention as would be apparent to one of ordinary skill in the art.

In one embodiment, the process comprises receiving user information 1801. This process may involve collecting various types of data related to the user's health, which will be used as input for the AI system to generate potential concerns and warnings.

The user information received in this process may comprise at least one of the following: user-reported symptoms, medical history or records, and sensor data from a medical device. User-reported symptoms are subjective descriptions of the user's health concerns, such as pain, discomfort, or any noticeable changes in bodily functions. Medical records may comprise observations, findings, and assessments made by healthcare professionals during user encounters and/or previously recorded sensor data. Sensor data from medical devices can provide objective measurements of the user's vital signs, such as heart rate, blood pressure, or oxygen saturation levels. The user information may be obtained as part of a telehealth interaction. In one aspect, user health information may comprise genetic information associated with the user.

In some cases, the user information may comprise two or more of the aforementioned data types, providing a more comprehensive view of the user's health status. The sensor data from medical devices may be obtained in real-time, allowing for real-time sensor data to be factored into the AI analysis. In one aspect, real-time sensor data may allow for continuous monitoring and timely updates to the AI system. This real-time data acquisition is particularly useful for users with chronic conditions or those requiring close monitoring. In one aspect, real-time sensor data may be continuously monitored for signs of user deterioration. If deterioration is detected (e.g. sensor data exceeds or falls below certain thresholds, sensor data deviates from an expected trajectory, etc.), an alert may be generated and transmitted to alert at least one of the user and a healthcare provider of the detected deterioration.

The sensor data may be obtained by a multi-sensor medical device, which can collect multiple types of physiological data simultaneously. Such devices may include wearable technology, such as smartwatches or patches, equipped with various sensors like accelerometers, gyroscopes, and photoplethysmography (PPG) sensors.

The medical device used for data collection may be a user device associated with the user, such as a smartphone or tablet with built-in sensors or connected to external sensors. Alternatively, the medical device may be associated with a clinician, such as a nurse or physician, who uses it to collect user data during a consultation or examination.

The process of receiving user information 1801 may be performed locally on a user device, leveraging edge computing capabilities like AI on a chip. This approach allows for faster processing and reduced latency, as the data does not need to be transmitted to a remote server. Alternatively, the user information may be received and processed by a server or cloud-based processing system, which can handle larger volumes of data and perform more complex computations.

In some scenarios, the user information may be received as part of a telehealth consultation process, where the user and healthcare provider communicate remotely using video conferencing or messaging platforms. This approach enables the collection of user data without the need for an in-person visit.

Additionally, the user information may further comprise medical history, such as data imported from electronic medical records (EMR) systems. This historical data can provide valuable context and insights into the user's overall health, including past diagnoses, treatments, and outcomes.

Alternatives to the described process of receiving user information 1801 may include manual data entry by healthcare professionals or users themselves, using web-based forms or mobile applications. Another alternative is the use of natural language processing (NLP) techniques to extract relevant information from unstructured data sources, such as clinical notes or user narratives.

In one embodiment, identifying health metric(s) 1802 is a software process designed to process the user information and identify abnormal metrics (e.g. measurements and/or patterns) or metrics associated with potential health concerns. This process may involve extracting a set of features from the raw data and storing these features in a standardized format. Identifying health metrics may comprise first receiving the raw user data, which could include a variety of information such as user-reported symptoms, sensor data from medical devices, and health records. The process then extracts a set of features from this data. These features could be specific data points, statistical measures, or derived variables that are relevant for an AI model to use in identifying potential concerns. The result of the extraction process is a set of features that represent the original data in a condensed and standardized form, suitable for input to the AI models.

The extracted features are then stored in a standardized format. This could be a database, a data file, or a data structure in memory. The standardized format ensures that the features are organized and accessible in a consistent manner, facilitating their use by the AI models and other parts of the system. There are various ways to implement the processing of user information 1802. For example, the feature extraction could be based on a fixed schema, where the same set of features is extracted for all users. Alternatively, it could be based on a dynamic schema, where the set of features is adapted for each user based on their specific characteristics or conditions. The specific implementation could depend on factors such as the type of user data, the complexity of the AI models, and the computational resources available.

In one embodiment, generating a health assessment 1803 is a software process designed to interpret the user data and output a health status (e.g. a status(es) associated with a potential concern(s)). This process uses deep learning models to analyze the features extracted from the user data and generate a health status, which may be associated with a likelihood score. The health assessment may indicate when an abnormality is identified and may further identify the severity of the abnormality. For example, a user's blood pressure may be identified as being low, normal, prehypertension, stage 1 hypertension, stage 2 hypertension.

The process operates by first receiving the health metrics. This information is then input to one or more deep learning models. The one or more deep learning models may comprise an ensemble of models. These models are trained to recognize patterns and correlations in the data that are indicative of various abnormalities and/or concerns. The one or more deep learning models may comprise at least one of a convolutional neural network, a recurrent neural network, and a transformer model. In one aspect, the convolutional neural network may be operable to process image data, the recurrent neural network operable to process time-series data, and the transformer model operable to process unstructured text data In one aspect, each model in the ensemble may be specialized for a specific type of data or potential concern. For example, one model may be trained on data associated with cardiovascular conditions, while another model may be trained on data associated with neurological conditions. The output of each model is a potential concern, or a set of potential concern, each which may be associated with a likelihood score. In one aspect, each model may be adapted to a given user such that the models look for and identify conditions which are abnormal for that user (e.g. based on a user-specific baseline).

There are various ways to implement the processing of user information and/or health metrics. For example, the deep learning models could be based on different architectures, such as convolutional neural networks for image data or recurrent neural networks for time series data. The models could also be trained using different algorithms, such as gradient descent or genetic algorithms. The specific implementation could depend on factors such as the type and complexity of the user data, the requirements for accuracy and interpretability, and the computational resources available.

In one embodiment, generating a health indicator 1804 is a software process for generating an indicator based on the health assessment. The health indicator may comprise an indication of no health concern detected or a warning of a potential health concern detected. The warning may comprise a warning selected from a plurality of tiered warnings. The warning may be selected based on the health assessment. For example, a more severe health assessment may result in a corresponding warning. For example, a severe health assessment may correspond with a warning to call emergency medical services or go to a hospital or emergency care facility, while a less seer health assessment may correspond with a warning to contact a primary care physician.

Providing a warning 1805 may comprise providing a warning based on at least one of the health indicator and health assessment. This may comprise providing a warning selected from a plurality of tiered warnings. For example, the health assessment may indicate a measure or pattern that is abnormal or out of range, while the health indicator may indicate a severity of a potential health concern depending on how abnormal or how far out of range the health assessment is. This severity may serve to identify a corresponding warning to be provided. For example, in the more severe cases, the warning may comprise a warning that emergency medical attention is needed, while less severe cases may be associated with a warning that something abnormal has been identified, but does not require urgent attention.

Providing an action step 1806 may comprise providing a recommended action based on at least one of the health assessment, health indicator, and warning. This may comprise an action corresponding to the severity of the health indicator or warning. For example, in the more severe cases, an action step may comprise an indication to the user to call emergency medical services or such a call may be automatically placed on behalf of the user. Another action step may comprise an indication that the user should go to the nearest emergency department, hospital, or medical clinic for immediate care. Action steps for the less severe cases may comprise an indication to the user to follow up with a primary care provider to address the abnormal finding(s).

In one aspect, the process may further comprise tracking changes in the user's health data over time using a temporal reasoning component and adjusting the personalized health assessment based on identified trends and patterns.

In one aspect, the process may further comprise repeatedly receiving user health information at different time points and generating the health assessment based on at least one of a measure and a pattern associated with the repeatedly received user health information.

In one aspect, the process may further comprise fine-tuning the at least one machine learning model based on at least one of the real-time sensor data, patient-reported symptoms, medical history information, the health assessment, and the health indicator. Fine-tuning the at least one machine learning model comprises fine-tuning the model to generate a user-specific model for predicting potential health concerns for the individual user. Fine-tuning the at least one machine learning model comprises fine-tuning the model to update a central model for predicting potential health concerns across a plurality of users.

In one embodiment, the software process of fine-tuning the model involves adjusting the parameters of the deep learning model used to generate potential health concerns. This fine-tuning is based on new user information received and feedback associated with outcomes and/or warnings regarding the appropriateness or suitability of the potential health concerns previously identified. The objective is to improve the model's accuracy and reliability in identifying potentially adverse user conditions.

The fine-tuning process works by first identifying aspects of the model that could benefit from adjustment. This could involve analyzing the model's performance in light of the latest user data and outcomes feedback to pinpoint inaccuracies or areas of uncertainty. Based on this analysis, the model's parameters are adjusted to better reflect the patterns and relationships present in the updated dataset. This could include modifying weights within the neural network, changing the architecture of the model, or updating the training algorithm.

One approach to fine-tuning the model involves using a reinforcement learning strategy. In this approach, the model is treated as an agent that learns from interactions with an environment—in this case, the dataset of user information and warnings issued and corresponding outcomes resulting from those warnings. The model makes predictions (actions) based on the data (state), and adjustments are made based on the outcomes (reward). Over time, the model learns to make more accurate predictions by maximizing the rewards it receives, which correspond to positive feedback from outcomes and alignment with actual user abnormalities or health concerns. In one aspect, the reinforcement learning comprises at least one of defining a reward function based on at least one of the appropriateness of the potential concerns identified and the efficiency of the warning process, exploring alternative health concern identification by perturbing the inputs to the at least one deep learning model, and updating the model parameters to maximize the expected cumulative reward over time.

Alternatives to reinforcement learning for fine-tuning the model could include supervised learning, where the model is retrained on a dataset that has been updated with new user information and annotated with correct health concerns based on clinician input and/or outcome feedback. Another alternative could be unsupervised learning, where the model adjusts itself by identifying patterns and anomalies in the data without explicit guidance on the correct health concerns.

The fine-tuning process could be implemented as a continuous, automated procedure that occurs at regular intervals, or it could be initiated manually in response to significant updates to the dataset or feedback from users. The choice of implementation may depend on factors such as the volume and velocity of new data and feedback, the computational resources available, and the desired balance between model stability and adaptability.

By fine-tuning the model based on the latest data and feedback, the software process of fine-tuning the model ensures that the AI system remains up-to-date and aligned with current medical knowledge and practices, thereby enhancing its utility and effectiveness in warning users of potential health concerns.

In one embodiment, the software process may further comprise updating the model and/or training data which involves modifying the parameters of at least one deep learning model and refreshing the dataset used for training these models. This update is based on insights gained from the fine-tuning process, incorporating new user information and outcomes associated with warnings to enhance the model's health concern identification capabilities.

The process begins with the collection of new data, which may include recent user information and feedback associated with outcomes based on potential health concerns identified and warnings issued using the model. This new data is then preprocessed to extract relevant features and standardized to align with the existing training dataset. The updated dataset includes this new information, enriching the diversity and volume of data available for training the deep learning models.

Following the data update, the model parameters are adjusted. This adjustment is informed by the outcomes of the fine-tuning process, which identifies the model's strengths and areas for improvement. The parameters might be updated to reflect new insights into disease patterns, symptom correlations, or other health concern factors highlighted by recent data and feedback.

One approach to updating the model involves retraining the deep learning model with the enriched training dataset. This retraining process allows the model to learn from the expanded dataset, incorporating the latest user information and provider insights into its health concern predictions.

Alternatives to retraining include incremental learning, where the model is updated with new data without retraining from scratch, and transfer learning, where a pre-trained model is adapted to the updated dataset with minimal changes to its structure. These alternatives can offer efficiencies in terms of computational resources and time, especially when dealing with large datasets or complex models.

The updated model and training data are then validated to ensure that the updates have improved the model's performance. This validation can involve techniques such as cross-validation or using a separate test dataset to assess the model's accuracy and reliability in predicting potential health concerns.

By regularly updating the model and training data, the software process of updating the model and/or training data ensures that the deep learning models remain effective and relevant, leveraging the latest available information and feedback to support accurate and timely identification of health concerns.

Figure 19:
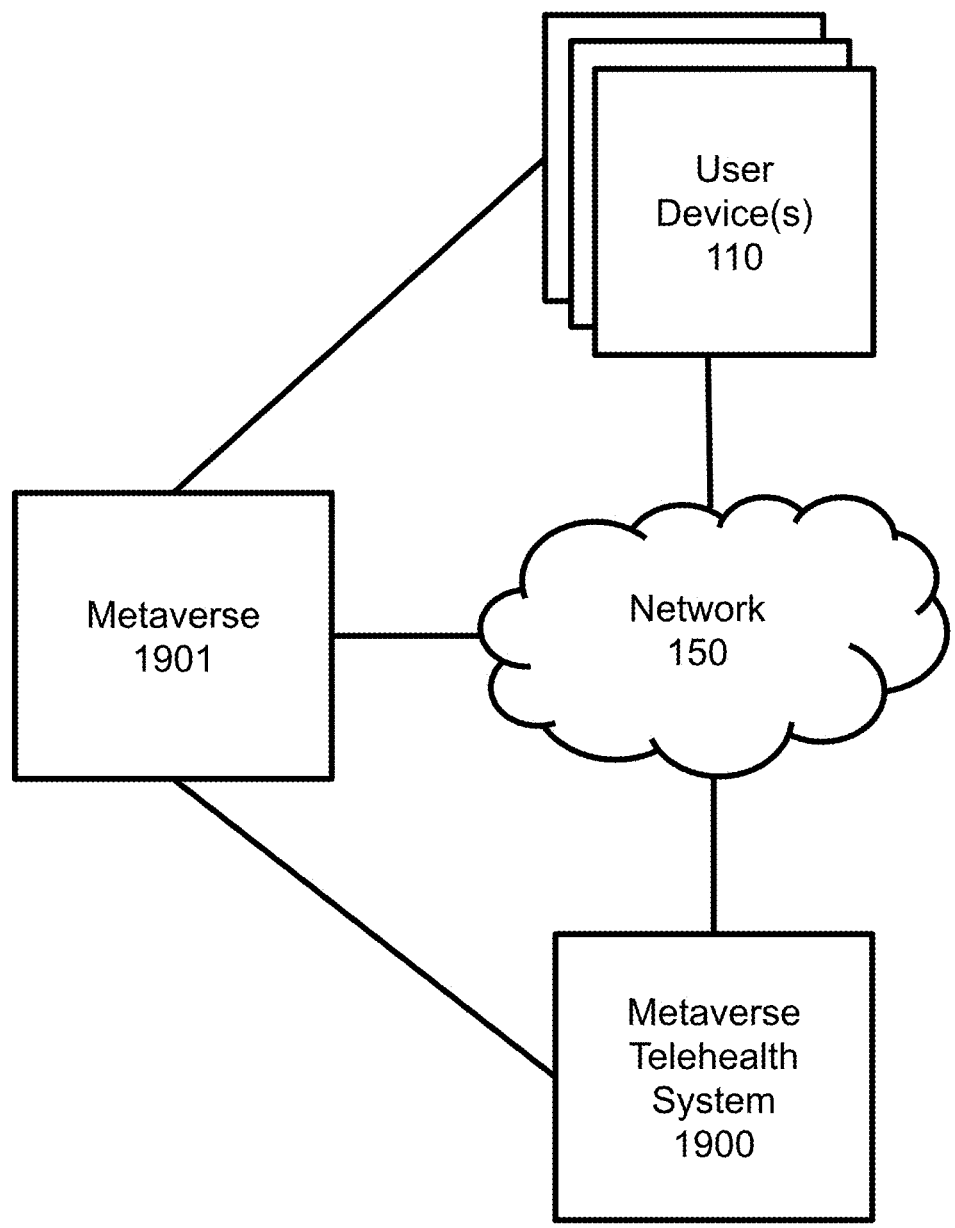
FIG. 19 illustrates exemplary systems and methods for artificial intelligence based health warning in accordance with an exemplary embodiment of the invention.

FIG. 19 illustrates an exemplary embodiment of systems and methods for healthcare services in virtual environments according to one embodiment. The system includes user device(s) 110, metaverse telehealth system 1900, and a network 150 over which the various systems communicate and interact. The various components described herein are exemplary and for illustration purposes only and any combination or subcombination of the various components may be used as would be apparent to one of ordinary skill in the art. The system may be reorganized or consolidated, as understood by a person of ordinary skill in the art, to perform the same tasks on one or more other servers or computing devices without departing from the scope of the invention. The various components described herein are exemplary and for illustration purposes only and any combination or subcombination of the various components may be used as would be apparent to one of ordinary skill in the art. The system may be reorganized or consolidated, as understood by a person of ordinary skill in the art, to perform the same tasks on one or more other servers or computing devices without departing from the scope of the invention.

In one embodiment, the metaverse telehealth system 1900 is designed to facilitate access to healthcare services within a virtual environment. The system enables users to engage with medical professionals through the interaction of their respective digital avatars, providing a seamless and immersive experience for receiving healthcare services without leaving the virtual world. Metaverse telehealth system 1900 may be accessed from the metaverse 1901. Metaverse telehealth system 1900 may serve as a form of gateway to the metaverse wherein a user accesses metaverse telehealth system 1900 to establish desired anonymity prior to accessing metaverse 1901.

The metaverse telehealth system 1900 operates by initiating a health consultation between a user's avatar and a licensed medical practitioner's avatar within the virtual environment. This interaction allows users to seek medical advice, discuss health concerns, and receive treatment recommendations from qualified healthcare professionals while maintaining the immersive experience of the metaverse.

To ensure user privacy and comfort, the metaverse telehealth system 1900 offers a customizable level of anonymity. Users can select the degree to which their personal information and avatar appearance are revealed during the consultation. This feature enables users to maintain control over their privacy and helps to foster a more open and comfortable environment for discussing sensitive health matters.

The system securely transmits health information exchanged during the consultation using advanced encryption and data protection mechanisms. This ensures that sensitive medical data remains confidential and is only accessible to authorized parties involved in the healthcare process. The secure transmission of health information is crucial for maintaining trust and compliance with relevant healthcare regulations.

Alternative implementations of the metaverse telehealth system 1900 may include additional features such as real-time translation services for multilingual consultations, integration with wearable devices for real-time health monitoring, or the ability to share medical images and test results within the virtual environment. The system could also incorporate machine learning algorithms to provide personalized health recommendations based on a user's medical history and lifestyle factors.

Another alternative approach could involve the use of haptic feedback devices to enhance the immersive experience during virtual consultations. These devices could simulate physical sensations, such as touch or pressure, to facilitate remote physical examinations or therapy sessions. Additionally, the system could incorporate augmented reality elements to provide visual aids and interactive demonstrations during consultations.

The metaverse telehealth system 1900 could also be expanded to include a network of specialists and healthcare facilities, allowing users to access a wide range of medical services and expertise within the virtual environment. This could include virtual visits to specialized clinics, consultations with experts from various medical fields, or even virtual support groups for individuals dealing with specific health conditions.

In one embodiment, user device(s) 110 are operable to interface with a virtual environment (e.g. metaverse 1901) and/or the metaverse telehealth system. These devices can include, but are not limited to, personal computers, laptops, smartphones, tablets, virtual reality headsets, or any other device capable of connecting to the internet and rendering a virtual environment. User device(s) 110 may comprise a medical/consumer electronics device such as the medical/consumer electronics device 140 discussed in at least FIG. 1 above. User device(s) 110 may interact directly with metaverse 1901 and/or through metaverse telehealth system 1900.

User device(s) 110 serve as the primary point of interaction between the user and the metaverse telehealth system. They allow the user to access the virtual environment, navigate within it, and engage with various functionalities, such as scheduling and attending virtual healthcare appointments, interacting with healthcare professionals through digital avatars, and receiving healthcare services.

The operation of user device(s) 110 involves connecting to the internet, accessing the metaverse telehealth system, and rendering the virtual environment. This process may involve the use of a dedicated application or a web browser, depending on the specific implementation of the metaverse telehealth system. Once connected, the user can navigate the virtual environment using input devices such as a keyboard, mouse, touchscreen, or virtual reality controllers. The user can also interact with the system using voice commands, gestures, or other forms of input, depending on the capabilities of the user device(s) 110.

The user device(s) 110 interface with the metaverse telehealth system through secure communication protocols to ensure the privacy and security of the user's data. These protocols may involve the use of encryption, secure tokens, and other security measures to protect the user's sensitive information. The user device(s) 110 may also incorporate additional security features, such as biometric authentication or behavioral analysis, to further enhance the security of the system.

In alternative embodiments, user device(s) 110 could be specialized hardware designed specifically for interfacing with the metaverse telehealth system. These devices could include advanced features such as haptic feedback, 3D spatial audio, and high-resolution displays to provide a more immersive and realistic virtual environment. Alternatively, user device(s) 110 could be a combination of multiple devices, such as a virtual reality headset for visual output and a smartphone for input and control, providing a flexible and customizable user experience.

User device(s) 110 include, generally, a computer or computing device including functionality for communicating (e.g., remotely) over a network 150. Data may be collected from user devices 110, and data requests may be initiated from each user device 110. User device(s) 110 may be a server, a desktop computer, a laptop computer, personal digital assistant (PDA), an in- or out-of-car navigation system, a smart phone or other cellular or mobile phone, or mobile gaming device, among other suitable computing devices. User devices 110 may execute one or more applications, such as a web browser (e.g., Microsoft Windows Internet Explorer, Mozilla Firefox, Apple Safari, Google Chrome, and Opera, etc.), or a dedicated application to submit user data, or to make prediction queries over a network 150.

In particular embodiments, each user device 110 may be an electronic device including hardware, software, or embedded logic components or a combination of two or more such components and capable of carrying out the appropriate functions implemented or supported by the user device 110. For example and without limitation, a user device 110 may be a desktop computer system, a notebook computer system, a netbook computer system, a handheld electronic device, or a mobile telephone. The present disclosure contemplates any user device 110. A user device 110 may enable a network user at the user device 110 to access network 150. A user device 110 may enable its user to communicate with other users at other user devices 110.

A user device 110 may have a web browser, such as MICROSOFT INTERNET EXPLORER, GOOGLE CHROME or MOZILLA FIREFOX, and may have one or more add-ons, plug-ins, or other extensions, such as TOOL-BAR or YAHOO TOOLBAR. A user device 110 may enable a user to enter a Uniform Resource Locator (URL) or other address directing the web browser to a server, and the web browser may generate a Hyper Text Transfer Protocol (HTTP) request and communicate the HTTP request to server. The server may accept the HTTP request and communicate to the user device 110 one or more Hyper Text Markup Language (HTML) files responsive to the HTTP request. The user device 110 may render a web page based on the HTML files from server for presentation to the user. The present disclosure contemplates any suitable web page files. As an example and not by way of limitation, web pages may render from HTML files, Extensible Hyper Text Markup Language (XHTML) files, or Extensible Markup Language (XML) files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a web page encompasses one or more corresponding web page files (which a browser may use to render the web page) and vice versa, where appropriate.

The user device 110 may also include an application that is loaded onto the user device 110. The application obtains data from the network 150 and displays it to the user within the application interface.

Exemplary user devices are illustrated in some of the subsequent figures provided herein. This disclosure contemplates any suitable number of user devices, including computing systems taking any suitable physical form. As example and not by way of limitation, computing systems may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, or a combination of two or more of these. Where appropriate, the computing system may include one or more computer systems; be unitary or distributed; span multiple locations; span multiple machines; or reside in a cloud, which may include one or more cloud components in one or more networks. Where appropriate, one or more computing systems may perform without substantial spatial or temporal limitation one or more steps of one or more methods described or illustrated herein. As an example, and not by way of limitation, one or more computing systems may perform in real time or in batch mode one or more steps of one or more methods described or illustrated herein. One or more computing system may perform at different times or at different locations one or more steps of one or more methods described or illustrated herein, where appropriate.

Network cloud 150 generally represents a network or collection of networks (such as the Internet or a corporate intranet, or a combination of both) over which the various components illustrated in FIG. 1 (including other components that may be necessary to execute the system described herein, as would be readily understood to a person of ordinary skill in the art). In particular embodiments, network 150 is an intranet, an extranet, a virtual private network (VPN), a local area network (LAN), a wireless LAN (WLAN), a wide area network (WAN), a metropolitan area network (MAN), a portion of the Internet, or another network 150 or a combination of two or more such networks 150. One or more links connect the systems and databases described herein to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable network 150, and any suitable link for connecting the various systems and databases described herein.

The network 150 connects the various systems and computing devices described or referenced herein. In particular embodiments, network 150 is an intranet, an extranet, a virtual private network (VPN), a local area network (LAN), a wireless LAN (WLAN), a wide area network (WAN), a metropolitan area network (MAN), a portion of the Internet, or another network 421 or a combination of two or more such networks 150. The present disclosure contemplates any suitable network 150.

One or more links couple one or more systems, engines or devices to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable links coupling one or more systems, engines or devices to the network 150.

In particular embodiments, each system or engine may be a unitary server or may be a distributed server spanning multiple computers or multiple datacenters. Systems, engines, or modules may be of various types, such as, for example and without limitation, web server, news server, mail server, message server, advertising server, file server, application server, exchange server, database server, or proxy server. In particular embodiments, each system, engine or module may include hardware, software, or embedded logic components or a combination of two or more such components for carrying out the appropriate functionalities implemented or supported by their respective servers. For example, a web server is generally capable of hosting websites containing web pages or particular elements of web pages. More specifically, a web server may host HTML files or other file types, or may dynamically create or constitute files upon a request, and communicate them to client/user devices or other devices in response to HTTP or other requests from client devices or other devices. A mail server is generally capable of providing electronic mail services to various client devices or other devices. A database server is generally capable of providing an interface for managing data stored in one or more data stores.

In particular embodiments, one or more data storages may be communicatively linked to one or more servers via one or more links. In particular embodiments, data storages may be used to store various types of information. In particular embodiments, the information stored in data storages may be organized according to specific data structures. In particular embodiments, each data storage may be a relational database. Particular embodiments may provide interfaces that enable servers or clients to manage, e.g., retrieve, modify, add, or delete, the information stored in data storage.

The system may also contain other subsystems and databases, which are not illustrated in FIG. 1, but would be readily apparent to a person of ordinary skill in the art. For example, the system may include databases for storing data, storing features, storing outcomes (training sets), and storing models. Other databases and systems may be added or subtracted, as would be readily understood by a person of ordinary skill in the art, without departing from the scope of the invention.

Figure 20:
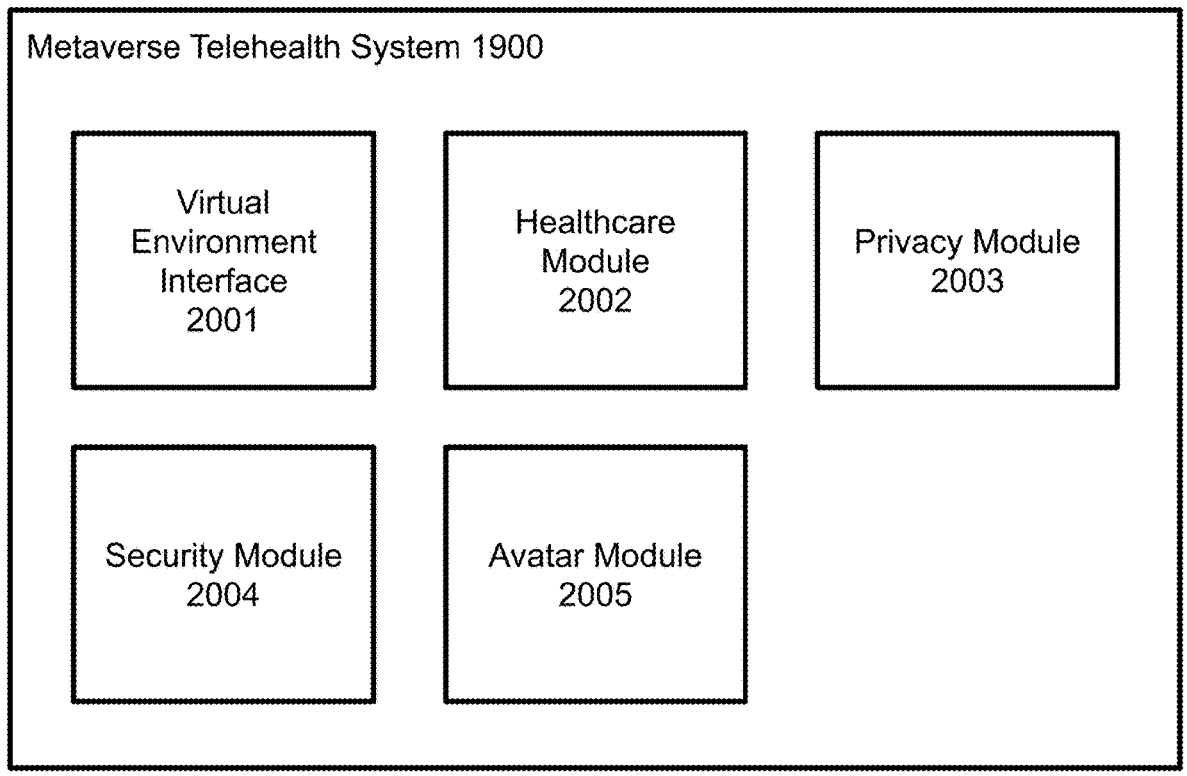
FIG. 20 illustrates an exemplary AI health warning system in accordance with an exemplary embodiment of the invention.

FIG. 20 illustrates an exemplary embodiment of the systems and methods for healthcare services in virtual environments. The system includes virtual environment interface 2001, healthcare module 2002, privacy module 2003, security module 2004, and avatar module 2005. The various components described herein are exemplary and for illustration purposes only and any combination or subcombination of the various components may be used as would be apparent to one of ordinary skill in the art. Other systems, interfaces, modules, engines, databases, and the like, may be used, as would be readily understood by a person of ordinary skill in the art, without departing from the scope of the invention. Any system, interface, module, engine, database, and the like may be divided into a plurality of such elements for achieving the same function without departing from the scope of the invention. Any system, interface, module, engine, database, and the like may be combined or consolidated into fewer of such elements for achieving the same function without departing from the scope of the invention. All functions of the components discussed herein may be initiated manually or may be automatically initiated when the criteria necessary to trigger action have been met.

In one embodiment, the virtual environment interface 2001 serves as a gateway that enables user devices to connect and interact with a virtual environment. This interface acts as a bridge between the user's physical device and the immersive digital world, allowing seamless access to the virtual environment and its various features.

The virtual environment interface 2001 facilitates the connection of multiple user devices to the virtual environment, creating a shared digital space that can be accessed by a plurality of users simultaneously. This enables individuals to enter and navigate the virtual environment, interact with digital objects, and engage with other users in real-time.

Once connected to the virtual environment, the interface 2001 is responsible for displaying an avatar associated with each user. These avatars serve as digital representations of the users within the virtual environment, allowing them to visually identify and interact with one another. The avatars can be customized to reflect the user's preferences, such as appearance, clothing, and accessories, providing a personalized and immersive experience.

The virtual environment interface 2001 works by establishing a secure connection between the user's device and the virtual environment server. This connection can be established using various communication protocols, such as WebSocket, TCP/IP, or UDP, depending on the specific requirements of the virtual environment. The interface handles data transmission between the user's device and the server, ensuring smooth and responsive interactions within the virtual environment.

To render the virtual environment and avatars on the user's device, the interface 2001 utilizes rendering engines and graphics libraries, such as Unity, Unreal Engine, or WebGL. These technologies enable the real-time rendering of 3D graphics, animations, and visual effects, creating a visually rich and immersive experience for the users.

Alternative implementations of the virtual environment interface 2001 may include additional features and functionalities. For example, the interface could incorporate virtual reality (VR) or augmented reality (AR) technologies to provide an even more immersive experience. VR interfaces would allow users to fully immerse themselves in the virtual environment using specialized headsets and input devices, while AR interfaces would overlay digital elements onto the user's real-world view.

Another alternative could involve the integration of haptic feedback devices with the virtual environment interface 2001. Haptic feedback provides tactile sensations to the user, simulating the sense of touch within the virtual environment. This could enhance the realism and interactivity of the virtual experience, allowing users to feel virtual objects or receive tactile cues during interactions.

The virtual environment interface 2001 could also incorporate voice recognition and natural language processing technologies to enable voice-based interactions within the virtual environment. This would allow users to communicate with other avatars or control their own avatar using voice commands, providing a more intuitive and hands-free interface option.

Additionally, the interface could include features such as gesture recognition, eye tracking, or facial expression tracking to capture and translate user movements and emotions into the virtual environment. This would enable more natural and expressive interactions between avatars, enhancing the sense of presence and social connection within the virtual space.

In one embodiment, the healthcare module 2002 is designed to facilitate virtual health consultations within the virtual environment. This module serves as the bridge between the user and the medical practitioner, enabling them to interact in a secure and efficient manner within the confines of the metaverse.

The healthcare module 2002 operates by creating a virtual space within the metaverse where health consultations can take place. This space is accessible to both the user and the medical practitioner, who are represented by their respective avatars. The user can schedule appointments, engage in consultations, and receive healthcare services, all within this virtual space.

The operation of the healthcare module 2002 involves several steps. First, the user schedules a consultation through the module. At the appointed time, the user's avatar and the medical practitioner's avatar meet in the designated virtual space. During the consultation, the user and the medical practitioner can communicate through their avatars, exchanging information and discussing the user's health concerns. The healthcare module 2002 facilitates this communication, ensuring that it is secure and private.

The healthcare module 2002 also integrates with other systems to provide a comprehensive healthcare service. For example, it can interface with a prescription management system to allow the medical practitioner to prescribe medication, which can then be delivered to the user's real-world location. It can also interface with a medical records system to allow the medical practitioner to access the user's medical history, subject to the user's consent.

In alternative embodiments, the healthcare module 2002 could offer additional features to enhance the virtual health consultation experience. For instance, it could incorporate virtual reality technology to create a more immersive consultation environment. It could also incorporate artificial intelligence to assist the medical practitioner in diagnosing and treating the user's health concerns. Alternatively, the healthcare module 2002 could be designed to facilitate group consultations, allowing multiple users to engage in a consultation with a single medical practitioner. In one embodiment, the privacy module 2003 is designed to enable the user to select a level of anonymity for the avatar associated with the user during the health consultations. This module provides a range of options for the user to control how much personal information is shared during these consultations, including an option for complete anonymity.

The privacy module 2003 operates by providing a user interface where the user can select their desired level of anonymity. This selection can be made at any time, allowing the user to adjust their level of anonymity as their needs and preferences change. The selected level of anonymity is then applied to the user's avatar during health consultations, controlling how much information is visible to the medical practitioner and other users in the virtual environment.

The operation of the privacy module 2003 involves several steps. First, the user accesses the privacy settings through the user interface. Here, they can choose from a range of anonymity options, from complete anonymity to full disclosure of personal information. Once the user has made their selection, the privacy module 2003 applies these settings to the user's avatar. This can involve changing the appearance of the avatar, modifying the information that is visible to others, or adjusting the user's visibility within the virtual environment.

The privacy module 2003 also integrates with other systems to ensure that the user's privacy is maintained across the entire metaverse telehealth system. For example, it can interface with the healthcare module to ensure that the user's level of anonymity is respected during health consultations. It can also interface with the user device(s) to ensure that the user's privacy settings are applied consistently across all devices.

In alternative embodiments, the privacy module 2003 could offer additional features to enhance the user's control over their privacy. For instance, it could provide more granular privacy settings, allowing the user to control individual aspects of their avatar's visibility. It could also incorporate artificial intelligence to suggest optimal privacy settings based on the user's behavior and preferences. Alternatively, the privacy module 2003 could be designed to allow the user to create multiple avatars, each with its own level of anonymity, to use in different contexts within the virtual environment.

At a high level, the security module (2004) is designed to ensure the secure exchange and storage of health-related information during a health consultation within a virtual environment. In one embodiment, the security module (2004) is responsible for securing the exchange of health-related information between the user's avatar and the licensed medical practitioner's avatar during the health consultation. This may involve implementing encryption protocols, such as end-to-end encryption, to protect the confidentiality and integrity of the data being transmitted between the avatars. The security module may also establish secure communication channels, such as virtual private networks (VPNs) or secure sockets layer (SSL) connections, to prevent unauthorized access or interception of the health-related information.

The security module (2004) is further configured to authenticate the identities of the user and the medical practitioner through secure tokens without requiring the disclosure of sensitive personal information. This authentication process may involve generating and verifying unique digital tokens or certificates that are associated with the user's and medical practitioner's avatars. These tokens can be used to confirm the identity and credentials of the participants without the need to share sensitive data, such as social security numbers or personal identification details, within the virtual environment.

In addition to securing the exchange of information, the security module (2004) is also operable to securely store at least one of a diagnosis and a treatment associated with the healthcare consultation in the virtual environment. This may involve employing encryption techniques, such as symmetric or asymmetric encryption, to protect the stored data from unauthorized access or tampering. The security module may also implement access control mechanisms, such as role-based access control (RBAC) or attribute-based access control (ABAC), to ensure that only authorized parties, such as the user and the medical practitioner, can access the stored diagnosis and treatment information.

One embodiment of the security module (2004) may utilize digital ledger and/or blockchain and/or similar technology to enhance the security and integrity of the health-related information. Digital ledger and/or blockchain technology provides a decentralized and immutable ledger that can be used to record and verify transactions, such as the exchange of health data or the storage of diagnoses and treatments. By leveraging digital ledger and/or blockchain, the security module can create an auditable and tamper-proof record of the health consultation, ensuring the authenticity and traceability of the information.

In an alternative embodiment, the security module (2004) may employ multi-factor authentication (MFA) mechanisms to further strengthen the identity verification process. This may involve requiring the user and the medical practitioner to provide additional forms of authentication, such as biometric data (e.g., fingerprints or facial recognition) or possession of physical tokens (e.g., smart cards or USB keys), in addition to the secure digital tokens.

Another alternative approach may involve the use of homomorphic encryption techniques, which allow for computations to be performed on encrypted data without the need to decrypt it. This enables the security module (2004)

to process and analyze health-related information while it remains in an encrypted state, reducing the risk of data exposure during processing.

The security module (2004) may also incorporate mechanisms for secure key management, such as key generation, distribution, and revocation, to ensure the integrity and confidentiality of the encryption keys used for securing the health-related information. This may involve using hardware security modules (HSMs) or secure enclaves to store and manage the encryption keys in a tamper-proof manner.

In one embodiment, the avatar module 2005 is designed to adjust an avatar of the user based on the level of anonymity selected via the privacy module. This module enables a user to create a customizable avatar, which serves as a virtual representation of the user in the virtual environment. The avatar module 2005 works in conjunction with the privacy module to temporarily change the avatar's appearance for the duration of a health consultation, based on the user's selected level of anonymity, and then revert the avatar back to its original state upon the completion of the consultation.

The operation of the avatar module 2005 involves several steps. Initially, the user creates and customizes their avatar using a range of customization options provided by the avatar module. These options include the ability to make the avatar resemble the real-life appearance of the user or to not resemble the user at all, among other customization features. When the user selects a level of anonymity through the privacy module, the avatar module 2005 receives this selection and adjusts the avatar's appearance accordingly. This could involve altering the avatar's facial features, body shape, clothing, or other identifiable characteristics to match the desired level of anonymity. Once the health consultation is completed, the avatar module 2005 automatically reverts the avatar to its previous state, preserving the user's original customization preferences.

In alternative embodiments, the avatar module 2005 could offer more advanced customization and anonymity options. For example, it could use artificial intelligence to generate a completely new avatar that maintains no visual connection to the user's real-life appearance, providing a higher level of anonymity. Alternatively, the module could allow users to save multiple avatar profiles, each with different levels of anonymity, which could be selected based on the context of the virtual environment or the nature of the health consultation. Another alternative could involve dynamic customization features that automatically adjust the avatar's appearance based on the type of virtual environment the user enters, providing contextual anonymity or visibility.

Figure 21:
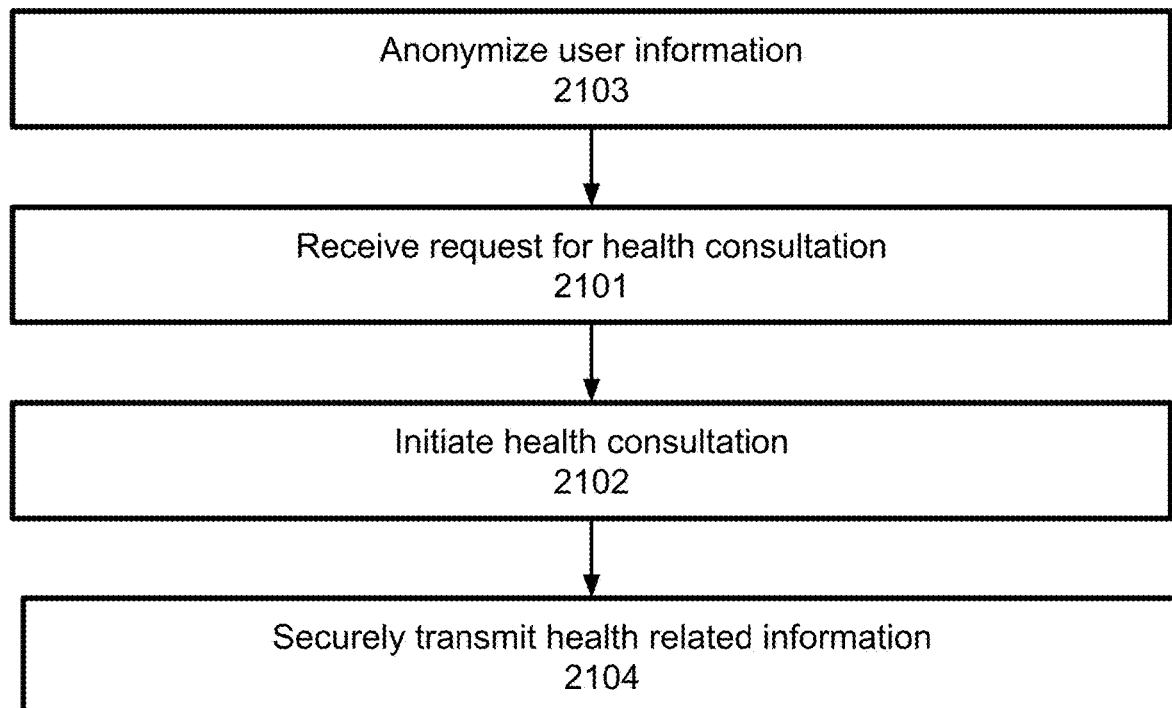
FIG. 21 illustrates an exemplary process for providing AI based warnings of potential health concerns.

FIG. 21 illustrates an exemplary process for providing secure healthcare consultation in a virtual environment. The process may comprise anonymizing user information 2103, receiving a request for a health consultation 2101, initiating a health consultation 2102, and securely transmitting health-related information 2104. The process steps described herein may be performed in association with a system such as that described in FIGS. 1-3 and/or FIG. 19-20 above or in association with a different system. The process may comprise additional steps, fewer steps, and/or a different order of steps without departing from the scope of the invention as would be apparent to one of ordinary skill in the art.

At a high level, the software process involves a health consultation within a virtual environment, such as the metaverse. The virtual environment is accessible by multiple users, and each user is represented by an avatar within the virtual environment.

The process may comprise anonymizing user information 2103 which may involve receiving a selection from a user regarding a desired level of anonymity to be used during the health consultation. This process allows the user to control how much personal information is shared during these consultations, including an option for complete anonymity where the user's avatar does not resemble the user's real-life appearance.

The process of anonymizing user information 2103 operates by providing a user interface where the user can select their desired level of anonymity. Once the user makes a selection, the process adjusts the user's avatar based on the selected level of anonymity. This adjustment changes the appearance of the avatar during the consultation, making it different from the appearance of the avatar prior to or after the consultation.

The operation of anonymizing user information 2103 involves several steps. First, the user accesses the privacy settings through the user interface and selects their desired level of anonymity. The system then processes this selection and adjusts the user's avatar accordingly. This adjustment can involve changing the avatar's physical features, clothing, or other attributes to make it less identifiable. The adjusted avatar is then used during the health consultation, providing the user with the selected level of anonymity.

In alternative embodiments, the process of anonymizing user information 2103 could incorporate additional features to enhance user privacy. For instance, it could provide more granular anonymity settings, allowing the user to control individual aspects of their avatar's appearance. It could also incorporate artificial intelligence to suggest optimal anonymity settings based on the user's behavior and preferences. Alternatively, the process could allow the user to create multiple avatars, each with its own level of anonymity, to use in different contexts within the virtual environment.

In one embodiment, the software process of securely transmitting health-related information 2104 involves the use of at least one of distributed ledger and/or blockchain technology and secure tokens to authenticate the identity of the user and/or medical practitioner without the need for disclosure of sensitive personal information. Additionally, this process includes securely storing at least one of a diagnosis and a treatment associated with the healthcare consultation in the virtual environment. Additionally, the process may comprise providing for secure export the at least one of a diagnosis, a treatment, and a recommendation.

The process operates by first authenticating the identities of the participants in the health consultation. This is achieved through the use of digital ledger and/or blockchain technology or secure tokens, which provide a secure and verifiable means of confirming identities without exposing personal information. Once authenticated, the health-related information exchanged during the consultation, such as diagnoses or treatment plans, is encrypted and stored securely within the virtual environment.

In one embodiment, the request for a health consultation (2101) is initiated by a user through their avatar within the metaverse. The user may interact with a designated virtual healthcare facility or a virtual healthcare provider's avatar to submit the request. The request may include information about the user's health concerns, symptoms, or specific medical needs.

The software process, upon receiving the request (2101), may verify the user's identity and authenticate their access to the virtual healthcare services. This authentication process may involve utilizing one or more of secure tokens, IP history, secure health records, driver's license information, social security number, location history, or behavioral analysis to ensure the user's identity without exposing sensitive personal information.

Once the user's identity is verified, the software process may generate a virtual consultation room or environment where the user's avatar can interact with a healthcare provider's avatar. The virtual consultation room may be designed to simulate a real-world healthcare setting, such as a doctor's office or examination room, to provide a more immersive and comfortable experience for the user.

During the virtual health consultation, the user's avatar may communicate with the healthcare provider's avatar through various means, such as voice chat, text chat, or virtual gestures. The healthcare provider's avatar may be controlled by a real healthcare professional who can provide medical advice, diagnoses, or treatment recommendations based on the user's health concerns.

In an alternative embodiment, the software process may utilize artificial intelligence (AI) or machine learning algorithms to analyze the user's health data and provide automated recommendations or guidance. In this case, the user's avatar may interact with an AI-powered virtual healthcare assistant rather than a human healthcare provider's avatar.

The software process may also include features for securely storing and managing the user's health data within the virtual environment. This may involve utilizing distributed ledger and/or blockchain technology to create an immutable and transparent record of the user's health information, ensuring privacy and data integrity.

Additionally, the software process may incorporate options for users to request and receive physical treatment items, such as medication, within the virtual environment. The user's avatar may interact with a virtual pharmacy or medication dispensary, and the requested items can be delivered to the user's real-world location.

At another step, the software process involves initiating a health consultation (2102) by connecting an avatar associated with a user and an avatar associated with a licensed medical practitioner within a virtual environment.

In one embodiment, once a request for a health consultation is received and the user's identity is verified, the software process initiates the health consultation (2102) by establishing a connection between the user's avatar and the avatar of a licensed medical practitioner within the virtual environment. This connection may be made through a secure virtual communication channel, ensuring the privacy and confidentiality of the consultation.

The user's avatar and the medical practitioner's avatar may interact within a designated virtual consultation room or environment that simulates a real-world healthcare setting. The avatars can communicate through various means, such as voice chat, text chat, or virtual gestures, allowing for a more immersive and interactive consultation experience.

During the health consultation, the medical practitioner's avatar may ask questions about the user's health concerns, symptoms, and medical history. The user's avatar can provide responses and share relevant health information with the medical practitioner's avatar. The medical practitioner's avatar may also perform virtual examinations or assessments, such as reviewing the user's virtual health records or analyzing virtual medical images or scans.

Based on the information gathered during the consultation, the medical practitioner's avatar can provide a diagnosis, treatment recommendations, or prescriptions to the user's avatar. The software process may incorporate secure mechanisms for transmitting and storing this information, such as encryption and/or digital ledger and/or blockchain technology, to maintain the privacy and integrity of the user's health data.

In an alternative embodiment, the software process may utilize artificial intelligence (AI) or machine learning algorithms to assist the medical practitioner's avatar in analyzing the user's health data and making more accurate diagnoses or treatment recommendations. The AI-powered system may process large amounts of medical data, research, and clinical guidelines to provide evidence-based suggestions to the medical practitioner's avatar.

Another alternative approach may involve connecting the user's avatar with a group of medical practitioners' avatars, enabling a multidisciplinary team approach to the health consultation. This may be particularly useful for complex medical cases that require expertise from multiple specialties.

The software process may also incorporate features for scheduling follow-up consultations or appointments within the virtual environment. The user's avatar may be able to view available time slots and book appointments with the medical practitioner's avatar or other healthcare providers' avatars, streamlining the continuity of care.

Additionally, the software process may include options for the user's avatar to grant temporary access to their virtual health records to the medical practitioner's avatar during the consultation. This allows for a more comprehensive evaluation of the user's health status while maintaining control over the privacy and sharing of personal health information.

The operation of securely transmitting health-related information 2104 involves several key steps. Initially, when a health consultation is initiated, the system generates a secure token or securely records the transaction (e.g. on a digital ledger and/or blockchain), depending on the method used. This serves to authenticate the participants. As the consultation proceeds and health-related information is exchanged, this data is encrypted and transmitted securely between the user and medical practitioner. Finally, the information is stored securely within the virtual environment, accessible only to authorized individuals.

In alternative embodiments, the process could incorporate additional security measures to enhance the protection of health-related information. For example, it could use end-to-end encryption for all communications during the health consultation, ensuring that the information remains private and secure. Alternatively, the process could employ multi-factor authentication for both users and medical practitioners, adding an extra layer of security to the identity verification process. Another alternative could involve the use of a permissioned digital ledger and/or blockchain, where only authorized participants can access the stored health-related information, providing controlled access while maintaining the benefits of digital ledger and/or blockchain's security and immutability.

Figure 23:
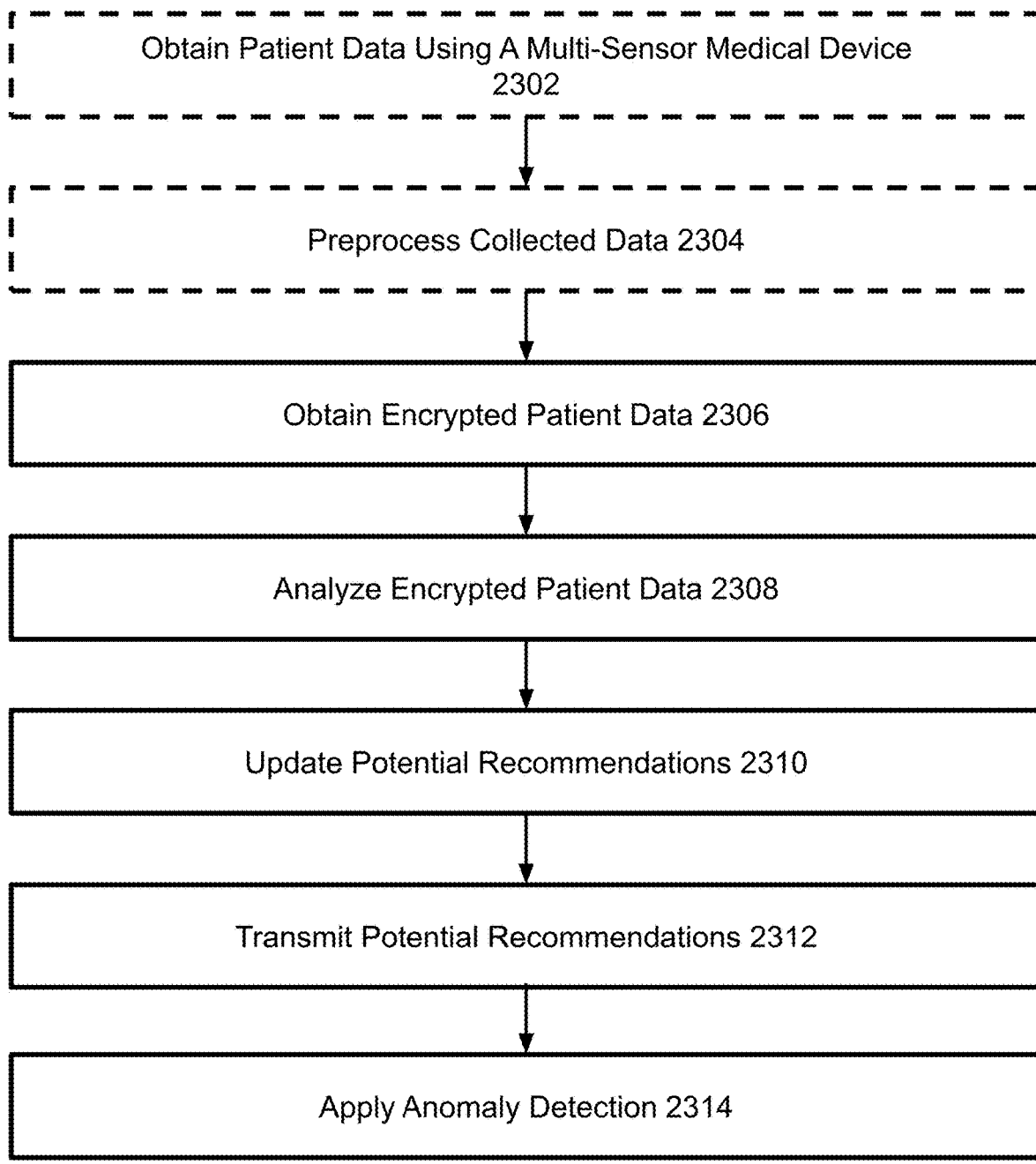
FIG. 23 illustrates an exemplary process for implementing the AI enabled multisensor connected telehealth system.

FIG. 23 illustrates an exemplary process for using handheld device with a cloud compute AI module within a telehealth ecosystem in accordance with an embodiment of the invention. At 2302, patient data is collected using a multi-sensor medical device (as describe above) that includes a plurality of sensors for monitoring various physiological parameters, such as heart rate, blood pressure, oxygen saturation, electrocardiogram (ECG), electroencephalogram (EEG), electromyogram (EMG), respiration rate, body temperature, blood glucose level, and physical activity. The sensors are arranged in a specific spatial configuration to optimize signal quality and minimize interference and optimize ergonomics (which affects data quality) and device profile/portability, and may include optical sensors, electrochemical sensors, piezoelectric sensors, and microelectromechanical systems (MEMS) sensors.

At 2304, the collected patient data is preprocessed using feature extraction techniques. The raw sensor data is processed using a feature extraction module that applies various signal processing and machine learning techniques to extract relevant features. The feature extraction techniques may include time-domain, frequency-domain, and time-frequency domain analysis methods, such as Fourier transform, wavelet transform, and short-time Fourier transform, as well as statistical methods, such as principal component analysis (PCA) and independent component analysis (ICA). The feature extraction module may also employ deep learning methods, such as convolutional neural networks (CNNs) and recurrent neural networks (RNNs), to learn hierarchical representations of the sensor data. Additionally, the module may apply a multi-scale decomposition technique, such as discrete wavelet transform (DWT) or empirical mode decomposition (EMD), to analyze the sensor data at different temporal and spatial resolutions, and may use a deep metric learning approach, such as siamese networks or triplet networks, to learn a compact and discriminative feature representation.

The preprocessed patient data is then securely transmitted using encryption at step 2306. The data is encrypted using a hybrid encryption scheme that combines symmetric and asymmetric encryption techniques to ensure secure transmission to a remote computing platform 2202. For real-time data transmission, a lightweight symmetric encryption algorithm, such as Advanced Encryption Standard (AES) or ChaCha20, is used to encrypt the data using a shared secret key, which is securely exchanged using a quantum key distribution (QKD) protocol. For privacy-preserving computation on the encrypted data, a homomorphic encryption scheme, such as Paillier cryptosystem or fully homomorphic encryption (FHE), is used to allow the remote computing platform to process the data without decrypting it. Additionally, a blockchain-based smart contract system is used to ensure secure and transparent data sharing among multiple stakeholders.

At step 2308, the encrypted patient data is analyzed using a hierarchical machine learning model to generate personalized diagnoses and treatment recommendations. The hierarchical model comprises multiple layers of abstraction to capture both low-level features and high-level semantic relationships in the data. At the lowest level, a convolutional neural network (CNN) is used to extract spatial features from image and video data. At the intermediate level, a recurrent neural network (RNN) is used to model the temporal dependencies in time-series data. At the highest level, a graph convolutional network (GCN) is used to integrate multimodal data from different sensors and sources. Transfer learning techniques are applied to leverage knowledge from related medical domains and improve the model's performance.

At step 2310, the potential recommendations are adapted based on provider feedback using reinforcement learning. A reinforcement learning module receives the provider feedback on the generated diagnoses and treatment recommendations and updates the hierarchical model to improve its performance. The reinforcement learning module formulates the problem as a Markov decision process (MDP) and employs a deep Q-network (DQN) algorithm to learn an optimal policy for generating personalized recommendations. The DQN algorithm uses a combination of supervised learning on the provider feedback and reinforcement learning on the patient outcomes, and incorporates delayed rewards to account for the long-term impact of the recommendations on the patient's health.

At step 2312, the potential recommendations are presented to the provider via an interactive user interface. The user interface employs a combination of natural language processing (NLP) and computer vision techniques to enable seamless and efficient interaction with the provider. The user interface generates a natural language explanation for each recommendation using a deep language model, and provides an immersive and interactive visualization of the patient's condition using a virtual reality (VR) or augmented reality (AR) system. The user interface (300) also provides personalized treatment simulations using a generative adversarial network (GAN), and employs a multimodal input system that combines voice, gesture, and touch input to capture the provider's feedback. A contextual bandit algorithm is used to adapt the display layout, information content, and interaction modality based on the provider's preferences and interaction patterns.

At step, 2314, anomalies in the patient's data are detected using a hybrid approach. A hybrid anomaly detection module continuously monitors the patient's data for any deviations from the normal patterns and generates alerts for the provider and/or patient/user when anomalies are detected. The hybrid module combines rule-based and data-driven approaches to identify both known and novel types of anomalies, and provides interpretable explanations for the detected anomalies. The rule-based approach uses a set of predefined rules and thresholds based on domain knowledge and clinical guidelines, while the data-driven approach uses machine learning algorithms, such as one-class support vector machines (SVMs) and deep autoencoder networks, to learn the normal patterns in the patient's data and detect any deviations. A Bayesian nonparametric model is used to adapt the anomaly detection thresholds to the patient's evolving condition and the provider's feedback.

The telehealth method of the present invention also includes several security and privacy features to protect the patient's data and ensure compliance with relevant regulations and standards. A federated learning framework is used to enable secure and privacy-preserving data storage and sharing, allowing multiple institutions to collaboratively train machine learning models without directly exchanging sensitive patient data. A differential privacy mechanism is used to protect the patient's identity and prevent unauthorized access to their data, by adding carefully calibrated noise to the data to guarantee a quantifiable level of privacy. A secure multi-party computation protocol is used to enable privacy-preserving analysis and decision-making on the patient's data, allowing multiple stakeholders to jointly compute a function on their respective inputs without revealing the inputs to each other.

Figure 24:
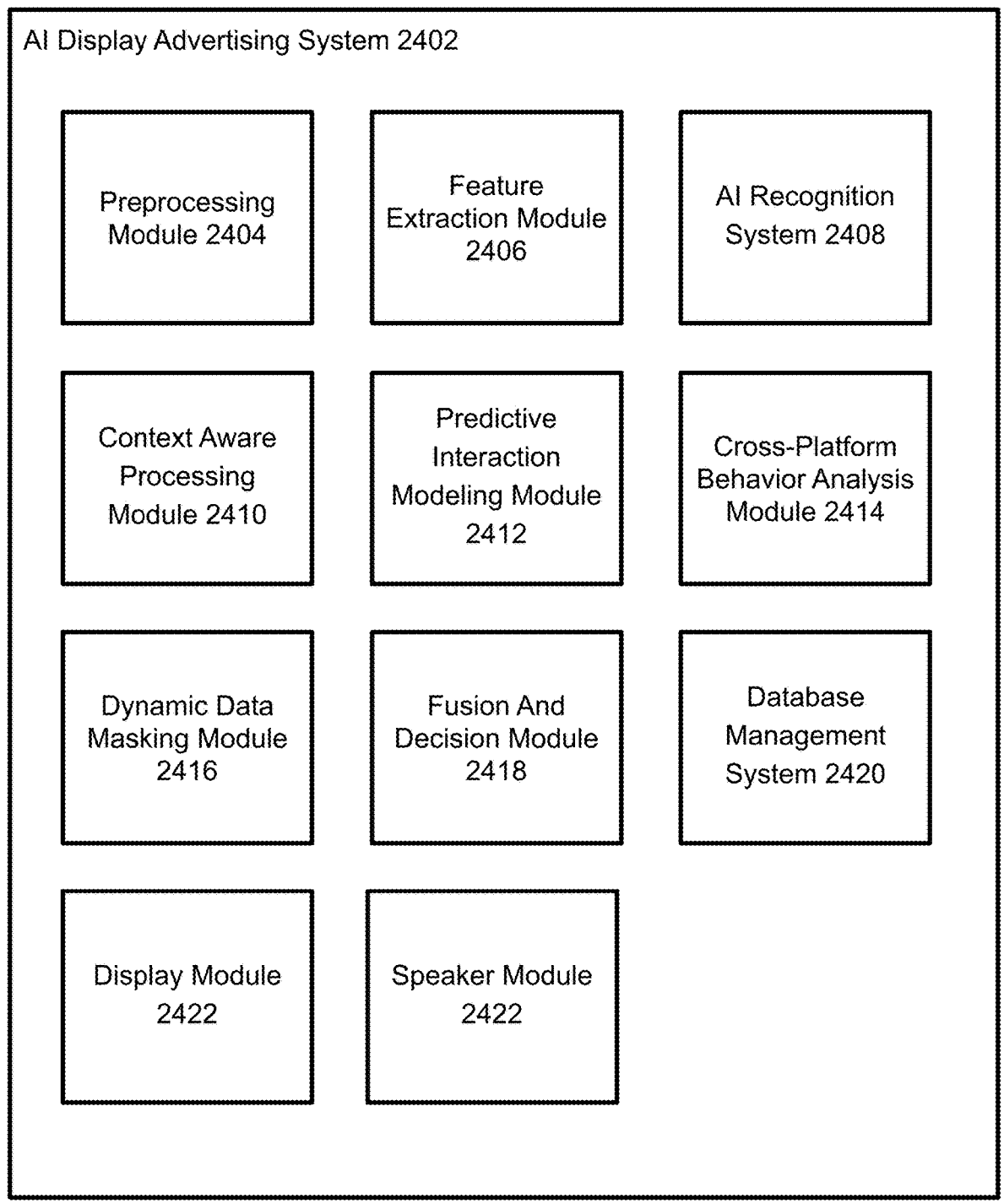
FIG. 24 illustrates an exemplary system for context aware data system using biometric and identifying data.

Now referring to FIG. 24, which illustrates a system for AI display advertisements 2402. The system is comprised of a biometric pre-processing module 2404, feature extraction module 2406, ai recognition system 2408, context aware processing module 2410, predictive interaction modeling module 2412, cross-platform behavior analysis module 2414, dynamic data masking module 2416, fusion and decision module 2418, and database management system 2420.

In one embodiment, the AI display advertisement system 2402 is embodied in a fixed or an installed device (i.e. it is not moveable or portable). In one embodiment, the AI audio and/or visual and/or audiovisual advertisement system based on biometric and/or other identifying data comprises a plurality of sensors configured to capture, including biometric data from individuals, including cameras for one of facial recognition, scleral microvasculature pattern detection, gait sensors, NIR cameras for vein and/or scleral microvasculature pattern detection, and microphones for voice capture. Other identification data from individuals, including license plate and/or mobile device identifying information (such as MAC addresses, location history, etc.), via previously mentioned cameras and antennas with numerous communication technologies (Bluetooth, WiFi, etc.).

The systems and processes for using sensors to identify individuals based scleral microvasculature pattern detection are disclosed herein in reference to FIGS. 11A, 11B, and 12 and associated text, supra. Those systems and processes for identifying an individual are used for identification in reference to the AI display advertisement system 2402 and hereby incorporated by reference. More specifically, the pattern and/or blood flow detection technologies alone or in combination may be used to identify an individual.

The system further comprising a pre-processing module 2204 configured to enhance captured biometric and/or other identifying data using image enhancement and signal processing techniques. A feature extraction module 2406 configured to extract features from the enhanced biometric and/or other identifying data. A recognition module 2408 including a plurality of neural network models, each configured to recognize individuals based on different biometric and/or other identification modalities. An aggregated context aware data module 2410 analyzing personally identifying information, location history, browsing history, and purchasing history acquired from data-sharing partners, for the purpose of: confirming the identity of the targeted individual, in combination with the data acquired, sending targeted notifications and/or advertisements to the targeted individual via audio and visual prompts. A context-aware processing module 2410 configured to adapt recognition strategies based on environmental data from sensors measuring physical parameters and ambient conditions. A display module 2422 configured to present personalized advertisements based on the identified individuals and the context-aware processing results, wherein the display module is pre-installed and not portable. A speaker module 2424 for audio advertising, which may or may not be used in conjunction with the display module in real time.

The pre-processing module 2404 is a component of the biometric identification system that enhances the quality of the captured biometric data to improve the accuracy and reliability of the recognition process. The module applies various image enhancement and signal processing techniques to the raw biometric data to reduce noise, normalize variations, and extract relevant features for subsequent analysis and matching.

In one embodiment, the pre-processing module 2404 uses the Contrast Limited Adaptive Histogram Equalization (CLAHE) algorithm to enhance the contrast of facial images. The CLAHE algorithm divides the image into small regions, called tiles, and applies histogram equalization to each tile separately. This helps to improve the local contrast of the image while avoiding the over-amplification of noise. Additionally, the module employs the Non-Local Means (NLM) denoising algorithm to reduce noise in the facial images. The NLM algorithm estimates the noise-free value of each pixel by computing a weighted average of the pixel values in a local neighborhood, where the weights are based on the similarity of the pixel intensities.

In another embodiment, the pre-processing module 2404 uses the Butterworth low-pass filter to remove high-frequency noise from gait data. The Butterworth filter is a type of signal processing filter that has a flat frequency response in the passband and a smooth roll-off in the stopband. The module also employs the Dynamic Time Warping (DTW) algorithm to normalize the temporal dimension of the gait data. The DTW algorithm aligns two temporal sequences by finding the optimal non-linear mapping between them, which helps to account for variations in the speed and duration of the gait cycles.

In yet another embodiment, the pre-processing module 2404 uses the Adaptive Gaussian Threshold (AGT) method for binarization of near-infrared (NIR) images of vein patterns. The AGT method computes a local threshold for each pixel based on the mean and standard deviation of the pixel intensities in a local neighborhood. This helps to adapt the binarization process to the local variations in the image contrast and brightness. The module also applies morphological opening and closing operations to the binarized images to remove small noise regions and fill in gaps in the vein patterns.

In still another embodiment, the pre-processing module 2404 uses the Spectral Subtraction algorithm for noise reduction in voice samples. The Spectral Subtraction algorithm estimates the noise spectrum from the non-speech regions of the voice sample and subtracts it from the overall spectrum to obtain the clean speech spectrum. The module also employs the Voice Activity Detection (VAD) algorithm based on the energy and zero-crossing rate to identify the speech segments in the voice sample. The VAD algorithm computes the short-time energy and zero-crossing rate of the voice sample and compares them to predefined thresholds to detect the presence or absence of speech.

After the pre-processing step, the feature extraction module 2406 applies various feature extraction techniques to the enhanced biometric data to obtain compact and discriminative representations for recognition. In one embodiment, the module uses the VGGFace2 model, which is a deep convolutional neural network (CNN) trained on a large dataset of face images, to extract a 512-dimensional feature vector for each face. The CNN comprises multiple layers of convolutional, pooling, and fully connected layers that learn hierarchical representations of the facial features. In another embodiment, the module employs the Gait Energy Image (GEI) method to generate a compact representation of gait by averaging silhouette images over a gait cycle. The GEI is a grayscale image that captures the spatio-temporal characteristics of gait, such as the shape and dynamics of the silhouettes. In yet another embodiment, the module uses the Maximum Curvature (MC) algorithm to extract the centerlines of veins from the NIR images and the Hessian Matrix-based approach to detect vein bifurcations and endings. The MC algorithm computes the maximum curvature of the vein profiles and connects the high curvature points to form the centerlines, while the Hessian Matrix-based approach analyzes the local second-order derivatives of the image intensities to detect the vein bifurcations and endings. In still another embodiment, the module extracts Mel-Frequency Cepstral Coefficients (MFCCs) from the voice samples using a window size of 25 ms and a step size of 10 ms, along with the fundamental frequency (F0) and formants (F1-F4) using the Praat software. The MFCCs are a set of coefficients that represent the short-term power spectrum of the voice signal, while the F0 and formants capture the pitch and resonance properties of the vocal tract.

Alternative embodiments of the pre-processing module 2406 may use different algorithms and techniques for image enhancement, noise reduction, and feature extraction. For example, the module may use the Histogram of Oriented Gradients (HOG) algorithm for facial feature extraction, the Gabor filter-based method for gait feature extraction, the Local Binary Patterns (LBP) algorithm for vein pattern feature extraction, or the Linear Predictive Coding (LPC) coefficients for voice feature extraction. The choice of the specific algorithms and techniques may depend on the characteristics of the biometric modality, the computational resources available, and the desired level of accuracy and robustness.

In one embodiment, the AI-driven recognition system 2408 uses deep learning models to accurately recognize individuals based on their facial features, gait patterns, vein patterns, and voice signatures. The system employs a suite of specialized neural network architectures that are trained on large-scale datasets to learn discriminative representations of the biometric modalities and achieve high recognition accuracy.

In one embodiment, the AI-driven recognition system uses the FaceNet model for facial recognition. FaceNet is a deep convolutional neural network (CNN) that is trained using the triplet loss function on the VGGFace2 dataset, which contains over 3.3 million face images from more than 9,000 identities. The triplet loss function encourages the network to learn embeddings that maximize the distance between different identities while minimizing the distance between images of the same identity. The resulting model achieves an impressive accuracy of 99.63% on the challenging Labeled Faces in the Wild (LFW) benchmark, which comprises unconstrained face images with variations in pose, illumination, and expression.

In another embodiment, the AI-driven recognition system employs a Siamese CNN architecture for gait analysis. The Siamese CNN comprises two identical CNNs that share the same set of weights and are trained to compare two input gait sequences and determine if they belong to the same person or not. The model is trained on the OU-ISIR Gait Database, which contains gait sequences of over 4,000 subjects captured from different viewpoints and under various conditions. The Siamese CNN learns to extract discriminative features from the gait sequences and compute a similarity score between them. The model achieves an equal error rate (EER) of 1.2% on the OU-ISIR dataset, indicating its ability to accurately distinguish between genuine and impostor gait pairs.

In yet another embodiment, the AI-driven recognition system uses a Deep Belief Network (DBN) model for vein pattern recognition. The DBN is a generative graphical model that comprises multiple layers of restricted Boltzmann machines (RBMs), which are stochastic neural networks that learn to model the probability distribution of the input data. The DBN is trained on the PUT Vein Database, which contains near-infrared (NIR) images of hand vein patterns from 50 subjects. The model learns to extract hierarchical features from the vein patterns and reconstruct them from a compressed representation. The DBN achieves a recognition accuracy of 98.7% on the PUT dataset, demonstrating its effectiveness in capturing the intricate details of the vein patterns.

In still another embodiment, the AI-driven recognition system employs a Long Short-Term Memory (LSTM) network for voice signature analysis. The LSTM is a type of recurrent neural network (RNN) that can model long-term dependencies in sequential data by maintaining a memory cell that can store information over extended time intervals. The LSTM is trained on the VoxCeleb2 dataset, which contains over 1 million utterances from 6,112 speakers in various languages and accents. The model learns to extract speaker-specific features from the voice samples and generate a compact representation of the speaker's identity. The LSTM achieves an EER of 1.8% on the VoxCeleb1 test set, which comprises voice samples from 40 speakers in unconstrained environments.

Alternative embodiments of the AI-driven recognition system may use different deep learning architectures and training strategies depending on the specific requirements and constraints of the application. For example, the system may employ a ResNet-based CNN for facial recognition, a 3D CNN for gait analysis, a Convolutional Autoencoder for vein pattern recognition, or a Time-Delay Neural Network (TDNN) for voice signature analysis. The choice of the specific models and hyperparameters may be based on factors such as the size and quality of the training data, the computational resources available, and the desired trade-off between accuracy and efficiency.

In addition to the main recognition models, the AI-driven recognition system may also incorporate various techniques to improve the robustness and generalization of the recognition process. For example, the system may use data augmentation techniques such as random cropping, flipping, and rotation to increase the diversity of the training data and reduce overfitting. The system may also employ transfer learning techniques to leverage pre-trained models from related domains and adapt them to the specific biometric modalities. Furthermore, the system may use ensemble learning techniques such as bagging, boosting, or stacking to combine the predictions of multiple models and improve the overall recognition accuracy.

The context-aware processing module 2410 enables the system to adapt its recognition strategies based on the environmental conditions and user context. The module uses a combination of sensors, machine learning algorithms, and adaptive techniques to accurately detect the context and optimize the recognition process accordingly.

In one embodiment, the context-aware processing module 2410 employs the Bosch BME680 environmental sensor to measure various physical parameters such as temperature, humidity, pressure, and air quality. These parameters provide valuable information about the ambient conditions that may affect the biometric data acquisition and recognition performance. For example, high humidity levels may degrade the quality of fingerprint images, while low air quality may impact the accuracy of voice recognition.

In another embodiment, the module uses the Maxim MAX44009 ambient light sensor to detect the light levels in the environment. The ambient light intensity can have a significant impact on the quality and usability of certain biometric modalities such as facial recognition and iris recognition. By measuring the light levels, the module can determine if the environment is suitable for capturing high-quality biometric data and adjust the recognition algorithms accordingly.

In yet another embodiment, the module employs the Knowles SPH0645LM4H microphone to measure the ambient noise levels. The presence of background noise can severely degrade the performance of voice recognition systems, as it can mask the relevant speech features and introduce variability in the audio data. By quantifying the noise levels, the module can assess the reliability of the voice recognition results and adapt the signal processing and feature extraction techniques to mitigate the impact of noise.

In addition to the environmental sensors, the context-aware processing module 2410 also incorporates a crowd density estimation component to determine the level of crowding in the surrounding area. In one embodiment, the module uses the YOLOv4 object detection model, which is a state-of-the-art deep learning architecture trained on the CrowdHuman dataset, to detect and count the number of people in the scene. The YOLOv4 model achieves an impressive average precision (AP) of 85.4% for person detection, making it highly reliable for crowd density estimation. The module uses the crowd density information to adjust the recognition algorithms and prioritize the biometric modalities that are less affected by occlusions and interactions in crowded scenarios.

To analyze the sensor data and make context-aware decisions, the module employs a context analysis algorithm based on a decision tree classifier. In one embodiment, the classifier is trained on a dataset of 10,000 samples, which includes various combinations of sensor readings and corresponding context labels such as indoor/outdoor, day/night, and crowded/solitary. The classifier learns to map the sensor data to the appropriate context categories and achieves an impressive accuracy of 96% on a held-out test set. The context analysis algorithm enables the module to accurately determine the current environmental conditions and user context, which forms the basis for adapting the recognition strategies.

Based on the detected context, the module employs adaptive recognition techniques to optimize the biometric identification process. In one embodiment, the module uses a rule-based system that adjusts the weights of different biometric modalities according to the context. For example, in low-light conditions, the module may increase the weight of vein pattern recognition while decreasing the weight of facial recognition, as vein patterns are less affected by illumination variations. Similarly, in crowded environments, the module may prioritize gait recognition and voice recognition over facial recognition, as the latter may be more susceptible to occlusions and interference from other individuals.

To further optimize the recognition performance, the context-aware processing module 2410 incorporates a dynamic parameter adjustment mechanism based on a genetic algorithm. In one embodiment, the genetic algorithm is designed to search for the optimal hyperparameters of the AI models used for biometric recognition, such as the learning rate, batch size, and network architecture. The fitness function of the genetic algorithm is carefully crafted to maximize the recognition accuracy while minimizing the computational overhead, ensuring that the system can adapt to the context in real-time without compromising efficiency.

Alternative embodiments of the context-aware processing module 2410 may utilize different sensors, machine learning algorithms, and adaptation techniques depending on the specific requirements and constraints of the application. For example, the module may incorporate additional sensors such as accelerometers, gyroscopes, and proximity sensors to capture more fine-grained context information. The module may also employ other machine learning algorithms such as support vector machines, random forests, or deep neural networks for context analysis and classification. Furthermore, the module may explore different adaptation strategies such as feature selection, score normalization, or multimodal fusion to optimize the recognition performance based on the context.

The predictive interaction modeling module 2412 enables personalized and context-aware user interactions. In one embodiment, the module leverages machine learning algorithms and data integration techniques to build comprehensive user profiles, predict user preferences and behaviors, and generate tailored content and recommendations.

At a high level, the predictive interaction modeling module 2412 is comprised of a user profile database, a context integration component, predictive modeling algorithms, a personalized interaction engine, and a feedback and refinement component. These components work together to collect, process, and analyze user data from various sources, build predictive models of user behavior, and deliver personalized experiences to users.

In one embodiment, the module uses a MongoDB database to store user profiles, which contain demographic information, preferences, and historical interaction data. MongoDB is a popular NoSQL database that provides high scalability, flexibility, and performance for handling large volumes of semi-structured data. To ensure the security and privacy of user data, the database is encrypted using the AES-256 algorithm, which is a strong symmetric encryption standard. Additionally, access to the database is controlled using role-based access control (RBAC) mechanisms, which restrict access to authorized users based on their roles and permissions.

In one embodiment, an Apache Kafka streaming platform may be employed to integrate real-time context data with the user profiles. Kafka is a distributed messaging system that enables real-time data ingestion, processing, and analysis. In one embodiment, the context integration component uses Kafka to consume real-time data streams from the context-aware processing module 2410, such as sensor readings and environmental conditions, and merge them with the corresponding user profiles. This allows the module to maintain up-to-date and context-rich user profiles that reflect the users' current situations and preferences. The Apache Kafka streaming platform is an exemplary implementation detail, but other systems may be used as would be apparent to a person of ordinary skill in the art.

In one embodiment, predictive modeling algorithm may be implemented using the TensorFlow 2.0 library. TensorFlow is an open-source machine learning framework that provides a wide range of tools and APIs for building and deploying deep learning models. In one embodiment, the module uses a combination of recurrent neural networks (RNNs) and convolutional neural networks (CNNs) to model sequential and spatial patterns in user behavior. RNNs, such as Long Short-Term Memory (LSTM) networks, are well-suited for modeling time-dependent data and capturing long-term dependencies in user interactions. CNNs, on the other hand, are effective in extracting local features and patterns from interaction data, such as user preferences and item characteristics.

To train the predictive models, the module relies on a large dataset of user profiles and interaction histories, which are collected from various sources such as e-commerce platforms, social media, and mobile apps. In one embodiment, the dataset comprises of 100,000 user profiles and their corresponding interaction histories, providing a rich and diverse set of examples for learning user behavior patterns. The models are trained using the Adam optimizer, which is a popular gradient-based optimization algorithm, with a learning rate of 0.001 and a batch size of 128. These hyperparameters are carefully tuned to achieve a balance between model convergence speed and generalization performance.

Once the predictive models are trained, the personalized interaction engine uses them to generate personalized content and recommendations for users. In one embodiment, the engine employs a combination of rule-based and machine learning techniques to tailor the user experience. The rule-based component uses a set of predefined rules to filter and prioritize content based on user preferences and context, ensuring that the most relevant and appropriate items are presented to the user. The machine learning component, on the other hand, uses collaborative filtering and content-based filtering algorithms to generate personalized recommendations. Collaborative filtering identifies similar users based on their interaction histories and recommends items that these users have liked, while content-based filtering recommends items that are similar to the ones the user has previously interacted with.

To continuously improve the accuracy and relevance of the personalized interactions, the module incorporates a feedback and refinement component. This component uses online learning algorithms, such as stochastic gradient descent (SGD), to update the predictive models in real-time based on user feedback and engagement metrics. For example, if a user clicks on a recommended item or provides a positive rating, the module treats this as a positive signal and adjusts the model parameters accordingly. Conversely, if a user ignores or dismisses a recommendation, the module considers this as a negative signal and updates the models to reduce the likelihood of similar recommendations in the future.

Alternative embodiments of the predictive interaction modeling module 2412 may employ different data storage technologies, such as PostgreSQL or Cassandra, depending on the specific requirements of the application. The module may also explore other machine learning algorithms and architectures, such as decision trees, random forests, or deep reinforcement learning, to capture different aspects of user behavior and optimize the personalization strategies. Additionally, the module may incorporate more advanced techniques for data integration, such as data fusion or multi-view learning, to leverage complementary information from multiple data sources and improve the accuracy of the predictive models.

The cross-platform behavior analysis module 2414 enables analysis of user behavior by integrating data from both offline and online sources. The module 2414 leverages various IoT sensors, tracking technologies, data fusion algorithms, and machine learning techniques to collect, process, and analyze user behavior data, and generate rich user profiles that capture the full spectrum of user activities and preferences.

At a high level, the cross-platform behavior analysis module 2414 is comprised of an offline behavior data collection component, an online behavior data collection component, data fusion algorithms, a behavior pattern analysis component, and a profile generation and updating component. These components work together to gather user behavior data from diverse sources, integrate and analyze the data to discover meaningful patterns and insights, and create and maintain comprehensive user profiles.

In one embodiment, the offline behavior data collection component utilizes a range of IoT sensors and tracking technologies to capture user interactions and movements in physical environments. For example, Bluetooth beacons are deployed in retail stores to track user movements and dwell times at different product sections, while RFID tags are attached to products to monitor user interactions, such as picking up or trying on items. The collected offline behavior data is anonymized using the SHA-256 hashing algorithm to protect user privacy, and then aggregated using the Apache Spark big data processing framework for efficient storage and analysis.

In one embodiment, to collect online behavior data, the module employs various web tracking technologies, such as cookies and pixel tags, which are embedded in websites to track user browsing activities, clicks, and page views. Additionally, the module leverages mobile app tracking SDKs, such as Google Analytics for Firebase, to capture user interactions and events within mobile applications. The collected online behavior data is encrypted using the SSL/TLS protocol to ensure secure transmission and then transferred to the server using secure APIs for further processing and integration.

In one embodiment, in order to combine the offline and online behavior data into a unified view of user behavior, the cross-platform behavior analysis module 2414 employs advanced data fusion algorithms. These algorithms, based on probabilistic graphical models such as Bayesian networks and Markov random fields, are designed to integrate data from multiple sources, handle missing or noisy data, and capture the dependencies and relationships between different data points. The data fusion algorithms use techniques such as expectation-maximization (EM) and Gibbs sampling to learn the model parameters from the available data and perform inference to estimate the missing or uncertain values.

In one embodiment, once the behavior data is integrated, the behavior pattern analysis component applies a combination of unsupervised and supervised machine learning algorithms to discover meaningful patterns and segments in user behavior. Unsupervised learning algorithms, such as k-means clustering and hierarchical clustering, are used to group users based on their behavior similarities, revealing distinct behavior segments or archetypes. Supervised learning algorithms, such as decision trees and random forests, are employed to predict user behavior based on historical data, enabling targeted marketing, personalized recommendations, and proactive customer support.

In one embodiment, to further uncover valuable insights from user behavior data, the module incorporates association rule mining algorithms, such as Apriori and FP-Growth. These algorithms identify frequent itemsets and association rules, revealing patterns like "users who bought product A also bought product B" or "users who visited page X also clicked on link Y." Such insights can inform cross-selling strategies, product bundling decisions, and website optimization efforts.

In one embodiment, the profile generation and updating component is responsible for creating and maintaining comprehensive user profiles based on the analyzed behavior data. In one embodiment, the component employs a combination of batch processing and real-time processing techniques to ensure both the depth and timeliness of the user profiles. The batch processing component, built on the Apache Hadoop framework, processes large volumes of historical behavior data to generate initial user profiles that capture long-term behavior patterns and preferences. The real-time processing component, powered by the Apache Flink framework, continuously updates the user profiles based on new behavior data as it arrives, ensuring that the profiles remain up-to-date and reflective of users' evolving interests and needs.

Alternative embodiments of the cross-platform behavior analysis module 2414 may leverage different IoT sensors and tracking technologies, such as Wi-Fi tracking, computer vision, or sentiment analysis, to capture a wider range of user behaviors and emotions. The module may also explore other data fusion techniques, such as multi-view learning or deep learning-based approaches, to improve the accuracy and robustness of the behavior data integration. Additionally, the module may incorporate more advanced machine learning algorithms, such as deep neural networks, reinforcement learning, or transfer learning, to enhance the behavior pattern analysis and prediction capabilities.

The dynamic data masking module 2416 helps improve the privacy and security of sensitive user data. The module employs various data masking techniques to protect user information while still allowing authorized users and systems to access and process the data as needed. The module's dynamic nature enables it to apply the appropriate masking techniques based on the specific data attributes, user roles, and access policies, providing a flexible and adaptable approach to data security.

At a high level, the dynamic data masking module 2416 is comprised of a data masking component, a masked data storage component, a data access and processing component, and a data unmasking and auditing component. These components work together to protect sensitive data at rest and in transit, control access to the masked data, and maintain a secure and auditable record of all data masking and unmasking operations.

In one embodiment, the data masking component employs format-preserving encryption (FPE) to encrypt sensitive fields, such as names and addresses, while preserving their original format and structure. FPE allows the encrypted data to maintain its compatibility with existing applications and databases that expect specific data formats, such as fixed-length strings or numeric values. This enables seamless integration of the dynamic data masking module 2416 into the biometric identification system without requiring extensive modifications to the underlying infrastructure.

Another data masking technique used by the module in one embodiment may be tokenization, which replaces sensitive data with randomly generated tokens. The tokens serve as references to the original data and can be mapped back to the sensitive values using a secure lookup table. Tokenization provides an additional layer of security by ensuring that the original sensitive data is never stored or processed in its raw form, reducing the risk of data breaches or unauthorized access.

In one embodiment, the masked data is stored in a separate database that is encrypted using the AES-256 algorithm, a robust symmetric encryption standard. The separation of the masked data from the original sensitive data adds an extra level of protection, as it prevents direct access to the sensitive information even if the primary database is compromised. The masked data is accessed through secure APIs that enforce strict authentication and authorization controls, ensuring that only authorized users and systems can retrieve the masked data.

In one embodiment, to control access to the masked data, the data access and processing component employs role-based access control (RBAC) mechanisms. RBAC allows the definition of granular access policies based on user roles and permissions, ensuring that users can only access the data they are authorized to see. This prevents unauthorized users from accessing sensitive information and helps maintain the principle of least privilege.

In one embodiment, the data access and processing component also utilizes secure multi-party computation (MPC) techniques, such as homomorphic encryption and secret sharing, to perform computations on the masked data without revealing the underlying sensitive information. Homomorphic encryption allows computations to be performed directly on encrypted data, producing encrypted results that can only be decrypted by authorized parties. Secret sharing involves splitting the sensitive data into multiple shares and distributing them among different parties, ensuring that no single party can reconstruct the original data without the cooperation of the others. These MPC techniques enable secure data processing and analysis while maintaining the privacy and confidentiality of the sensitive information.

The data unmasking and auditing component is responsible for controlling the unmasking of masked data when authorized users or systems require access to the original sensitive information. In one embodiment, the component utilizes hardware security modules (HSMs) and secure enclaves, such as Intel SGX, to perform the unmasking operations. HSMs are tamper-resistant devices that securely store and manage cryptographic keys, ensuring that the unmasking process is protected from unauthorized access or tampering. Secure enclaves, like Intel SGX, provide a trusted execution environment that isolates sensitive code and data from the rest of the system, preventing unauthorized access or modification.

In one embodiment, to maintain a secure and auditable record of all data masking and unmasking operations, the data unmasking and auditing component employs blockchain technology. Blockchain creates an immutable and tamper-evident ledger that records every masking and unmasking operation, along with the associated metadata, such as the user, timestamp, and purpose of the operation. This audit trail ensures that all data access and modifications are traceable and verifiable, enabling easy detection of unauthorized activities and facilitating compliance with data protection regulations.

Alternative embodiments of the dynamic data masking module 2416 may employ different encryption algorithms, such as RSA or Elliptic Curve Cryptography (ECC), depending on the specific security requirements and performance considerations. The module may also explore other data masking techniques, such as data shuffling, data perturbation, or synthetic data generation, to provide additional options for protecting sensitive information. Additionally, the module may incorporate more advanced access control mechanisms, such as attribute-based access control (ABAC) or risk-based access control (RBAC), to enable more fine-grained and dynamic access policies based on various attributes or risk factors.

The fusion and decision module 2418 combines the outputs of multiple biometric modalities and makes a recognition decision. The module employs various fusion techniques and decision-making algorithms to improve the accuracy, robustness, and adaptability of the recognition process, ensuring reliable and secure identification of individuals.

At a high level, the fusion and decision module 2418 takes the feature vectors, matching scores, or decision outputs generated by the individual biometric modalities as inputs and applies fusion algorithms to combine them into a unified representation. The fused data is then processed by decision-making algorithms to determine the final recognition result, which indicates whether the input biometric data belongs to a known individual or not. The module also incorporates mechanisms for setting decision thresholds, handling errors, and adapting to new data and user feedback.

In one embodiment, the fusion and decision module 2418 employs feature-level fusion to combine the feature vectors extracted from each biometric modality. Feature-level fusion involves concatenating the feature vectors into a single, high-dimensional feature vector that represents the combined biometric information. This fused feature vector is then used as input to the classification algorithms for recognition. Feature-level fusion allows the module to capture the correlations and dependencies between different biometric modalities at an early stage, enabling more accurate and discriminative recognition.

Another fusion technique used by the module in one embodiment is score-level fusion, which combines the matching scores generated by each biometric modality. Matching scores indicate the similarity between the input biometric data and the stored templates for each modality. The module applies techniques such as weighted averaging, product rule, or sum rule to fuse the matching scores. These techniques assign different weights or importance to each modality based on their reliability, discriminative power, or user-specific characteristics. Score-level fusion provides a flexible and effective way to combine the recognition results from multiple modalities while considering their individual strengths and weaknesses.

In one embodiment, the final recognition decision is made using a combination of classification algorithms, such as Support Vector Machines (SVMs), decision trees, and random forests. SVMs are discriminative classifiers that find the optimal hyperplane to separate different classes in a high-dimensional feature space. Decision trees and random forests are tree-based classifiers that learn hierarchical decision rules based on the input features. These algorithms are trained on labeled biometric data to learn the decision boundaries and classification rules that distinguish between different individuals.

To improve the accuracy and robustness of the recognition system, the fusion and decision module 2418 incorporates ensemble learning techniques, such as bagging and boosting. Bagging (Bootstrap Aggregating) involves creating multiple subsets of the training data by random sampling with replacement, training separate classifiers on each subset, and combining their predictions through majority voting or averaging. Boosting, such as AdaBoost or Gradient Boosting, iteratively trains weak classifiers on weighted versions of the training data, where the weights are adjusted based on the misclassified samples. The final prediction is obtained by weighted voting of the weak classifiers. Ensemble learning helps to reduce overfitting, improve generalization, and handle noisy or inconsistent biometric data.

The decision thresholds used by the module to determine the recognition outcome are set based on the desired False Acceptance Rate (FAR) and False Rejection Rate (FRR). FAR represents the probability of incorrectly accepting an impostor, while FRR represents the probability of incorrectly rejecting a genuine user. The decision thresholds are adjusted to achieve a trade-off between security and usability, depending on the specific requirements of the application. In one embodiment, the module uses statistical techniques, such as Receiver Operating Characteristic (ROC) curves or Equal Error Rate (EER), to determine the optimal decision thresholds that balance FAR and FRR.

To adapt to new biometric data and user feedback, the fusion and decision module 2418 employs incremental learning techniques. Incremental learning allows the module to update its decision models and fusion parameters dynamically as new data becomes available, without requiring a complete retraining of the system. In one embodiment, the module uses online learning algorithms, such as Stochastic Gradient Descent (SGD) or Passive-Aggressive algorithms, to update the classifiers based on the incoming data streams. The module also incorporates user feedback, such as manual corrections or confirmations, to refine the recognition results and improve the system's performance over time.

Alternative embodiments of the fusion and decision module 2418 may explore different fusion techniques, such as rank-level fusion or decision-level fusion, depending on the characteristics of the biometric modalities and the available computational resources. The module may also employ other classification algorithms, such as neural networks, logistic regression, or Gaussian Mixture Models (GMMs), to suit specific recognition tasks or data distributions. Additionally, the module may incorporate quality assessment and quality-based fusion techniques to dynamically adjust the fusion weights based on the quality and reliability of each biometric sample.

The database management system 2420 enables secure and scalable storage and management of biometric templates and user profiles. In one embodiment, the system employs a combination of relational and NoSQL databases to handle both structured and unstructured data, ensuring optimal performance and flexibility.

At a high level, the database management system 2420 is responsible for storing, organizing, and retrieving biometric templates and user profiles. Biometric templates are mathematical representations of the unique features extracted from an individual's biometric data, such as facial features, fingerprints, or voice patterns. User profiles contain demographic information, enrollment details, and other relevant data associated with each user. The system ensures the integrity, confidentiality, and availability of the stored data through various security measures and backup mechanisms.

In one embodiment, the database management system 2420 utilizes a relational database, such as MySQL or PostgreSQL, to store structured data. Relational databases organize data into tables with predefined schemas, enforcing data consistency and enabling efficient querying using SQL (Structured Query Language). The structured data stored in the relational database includes user demographics, enrollment information, and other tabular data related to the biometric identification system.

In one embodiment, to handle unstructured data, such as biometric templates and interaction histories, the database management system 2420 employs a NoSQL database, such as MongoDB or Cassandra. NoSQL databases provide a flexible and scalable solution for storing and retrieving large volumes of unstructured data. They allow for schema-less data models, enabling the storage of biometric templates in their native formats without the need for rigid predefined structures. NoSQL databases also offer high performance and horizontal scalability, making them suitable for handling the growing amounts of biometric data.

In one embodiment, the databases are partitioned and replicated across multiple nodes to ensure scalability and availability. Partitioning involves dividing the data into smaller, manageable chunks and distributing them across different database nodes. This allows for parallel processing and load balancing, improving the system's performance and capacity. Replication involves creating multiple copies of the data and storing them on different nodes, providing fault tolerance and high availability. If one node fails, the system can continue operating using the replicated data from other nodes.

To improve the security of the stored data, the database management system 2420 employs encryption techniques. In one embodiment, the data is encrypted using the Advanced Encryption Standard (AES) with a 256-bit key size (AES-256). AES-256 is a strong symmetric encryption algorithm that provides a high level of security for the stored data. The encryption keys are managed using a Key Management System (KMS), such as HashiCorp Vault, which securely stores, manages, and rotates the encryption keys. The KMS ensures that the keys are protected and accessible only to authorized components of the system.

In one embodiment, the system employs incremental and differential backup techniques. Incremental backups capture only the changes made since the last backup, while differential backups capture the changes made since the last full backup. These techniques optimize the backup process by reducing the amount of data that needs to be backed up each time. The backups are stored in a secure off-site location to ensure data recovery even in the event of a catastrophic failure at the primary site.

To track changes and enable version control, the database management system 2420 utilizes a version control system, such as Git. Git allows for tracking modifications made to the database schemas, stored procedures, and other database-related artifacts. It provides a history of changes, enables collaboration among developers, and facilitates rollbacks in case of errors or failures. Version control ensures the integrity and reproducibility of the database environment.

In one embodiment, access to the databases is strictly controlled using Role-Based Access Control (RBAC) mechanisms. RBAC allows for defining and enforcing access policies based on user roles and permissions. Each user is assigned a specific role, such as administrator, operator, or analyst, which determines their level of access to the database. RBAC ensures that users can only access the data and perform actions that are relevant to their roles, minimizing the risk of unauthorized access or data breaches.

In one embodiment, to monitor and detect any suspicious or unauthorized activities, the database management system 2420 employs Database Activity Monitoring (DAM) tools. DAM tools continuously monitor the database queries and transactions, looking for patterns or anomalies that may indicate potential security threats or data breaches. They can alert administrators in real-time and provide detailed audit trails for forensic analysis and compliance purposes.

Alternative embodiments of the database management system 2420 may utilize different database technologies or architectures based on the specific requirements and scalability needs of the biometric identification system. For example, the system may employ a fully NoSQL-based approach using databases like Apache Cassandra or Google Cloud Bigtable for handling both structured and unstructured data. Alternatively, the system may use a hybrid approach, combining relational databases with other storage technologies like object storage or file systems for storing large biometric datasets.

Figure 25:
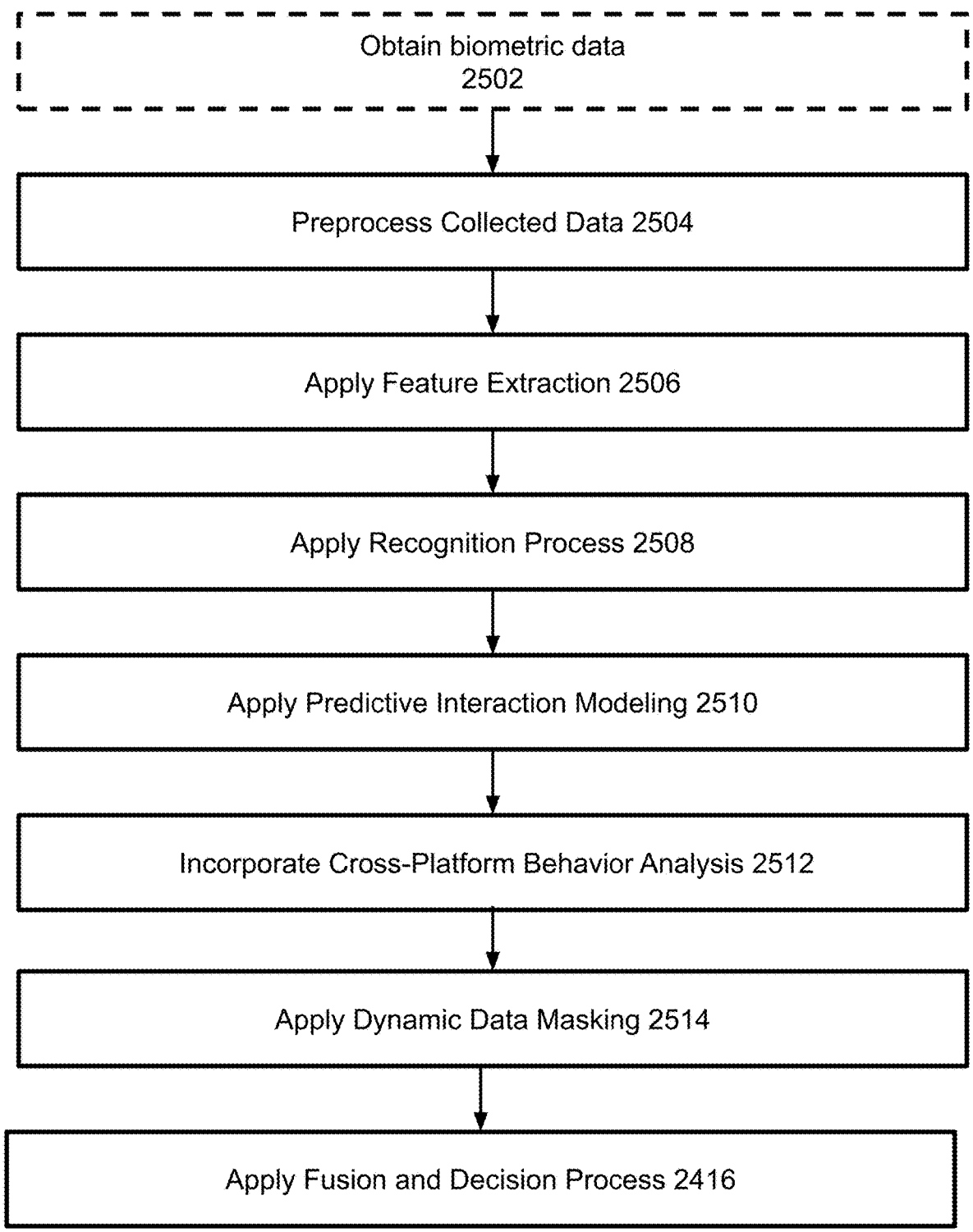
FIG. 25 illustrates an exemplary process for implementing a context aware data system using biometric and identifying data.

Now referring to FIG. 25, which illustrates the computer implemented process steps for serving personalized advertisements based on biometric data. The process employs a multi-modal biometric identification approach, combining facial recognition, gait analysis, vein pattern detection, and/or voice recognition to accurately identify individuals in real-time. The process further incorporates context-aware processing, predictive interaction modeling, cross-platform behavior analysis, dynamic data masking, and fusion and decision-making techniques to deliver highly targeted and privacy-preserving advertisements. Broadly, the method for serving personalized advertisements using biometric data comprises the steps of: capturing biometric and/or other identifying data from individuals via a plurality of sensors, enhancing the captured biometric and/or other identifying data using a pre-processing, extracting discriminative features from the enhanced biometric and/or other identifying data, recognizing individuals based on the extracted features using multiple neural network models tailored to each biometric and/or other identifying modality, adapting recognition and advertisement delivery strategies based on environmental conditions detected by physical and ambient sensors, and/or displaying personalized audio and/or visual and/or audiovisual advertisements on digital signage based on the recognition results and environmental context.

At step 2502, the process initiates when a plurality of sensors for capturing biometric data from individuals begin capturing data. These sensors include cameras for facial recognition, and/or cameras for scleral microvasculature pattern detection and/or microphones for capturing voice samples. The sensors are strategically placed in the target environment, such as retail stores, public spaces, or transportation hubs, to maximize the coverage and accuracy of biometric data acquisition. In one embodiment, the sensors are installed in place and not portable.

At step 2504, the captured biometric data is then processed by a pre-processing process 2504, which applies image enhancement and signal processing techniques to improve the quality and reliability of the data. In one embodiment, the pre-processing process 2504 employs Contrast Limited Adaptive Histogram Equalization (CLAHE) to enhance the contrast of facial images, making them more suitable for recognition. Additionally, the process 2504 uses Non-Local Means (NLM) denoising algorithms to reduce image noise and improve the signal-to-noise ratio.

After pre-processing, the enhanced biometric data is passed to a feature extraction step 2506, which extracts discriminative features from each biometric modality. For facial recognition, the process 2506 employs a VGGFace2 model, a deep convolutional neural network (CNN) trained on a large-scale face dataset, to extract high-level facial features. For gait analysis, the process 2506 uses a Gait Energy Image (GEI) method, which generates a compact representation of gait patterns by averaging silhouette images over a gait cycle. For voice recognition, the process 2506 extracts Mel-Frequency Cepstral Coefficients (MFCCs), which capture the spectral characteristics of the voice signal.

The extracted features are then fed into a recognition process 2508, which is comprised of a plurality of neural network models, each tailored to a specific biometric modality. For facial recognition, the process 2508 employs a FaceNet model, a state-of-the-art CNN architecture that learns to map facial features to a compact Euclidean space, where distances directly correspond to a measure of face similarity. For gait analysis, the process 2508 uses a Siamese CNN, which learns to compare two gait sequences and determine if they belong to the same individual. For voice recognition, the process 2508 employs a Long Short-Term Memory (LSTM) network, a type of recurrent neural network (RNN) that can effectively model the temporal dependencies in voice data.

The recognition process 2508 is comprised of context-aware processing, which adapts the recognition strategies based on environmental data from sensors measuring physical parameters and ambient conditions. The context-aware processing takes into account factors such as lighting conditions, temperature, humidity, and noise levels to dynamically adjust the recognition algorithms and optimize their performance. In one embodiment, the process 2508 includes a crowd density estimation component, which uses computer vision techniques to estimate the number and distribution of people in the target environment. Based on the crowd density information, the process 2508 can adapt the recognition strategies and advertisement targeting to ensure optimal performance and user experience.

Once the individuals are identified, the process leverages predictive interaction modeling 2510 to build user profiles, predict user preferences, and generate personalized advertisements. The predictive interaction modeling uses machine learning algorithms, such as collaborative filtering and content-based recommendation, to analyze user behavior, preferences, and historical interactions. The process 2510 integrates real-time context data with user profiles using a streaming platform, such as Apache Kafka, to generate dynamic and context-aware personalized advertisements. This enables the system to deliver highly relevant and timely advertisements based on the user's current context and predicted interests.

In one embodiment, to further enhance the accuracy and effectiveness of personalized advertising, the process incorporates a cross-platform behavior analysis 2512. This process analyzes user behavior across offline and online platforms, integrating data from various sources such as social media, e-commerce websites, and mobile applications. The process employs data fusion algorithms, such as probabilistic graphical models (e.g., Bayesian networks, Markov random fields), to effectively combine and integrate heterogeneous behavior data. By leveraging cross-platform behavior analysis, the system can gain a more comprehensive understanding of user preferences and interests, enabling more precise advertisement targeting.

To ensure the privacy and security of sensitive user data, the process includes a dynamic data masking process 2514. This process employs advanced data protection techniques, such as format-preserving encryption, tokenization, and secure multi-party computation, to safeguard user information while still allowing for personalized advertising. The process dynamically masks sensitive data fields, such as names, addresses, and biometric templates, replacing them with encrypted or tokenized values. This ensures that the original sensitive data is never exposed during the advertising process. Additionally, the process utilizes secure enclaves, such as Intel SGX, to perform privacy-preserving computations on the masked data, further enhancing the confidentiality of user information.

The process also incorporates a fusion and decision process 2516, which combines the outputs of multiple biometric modalities to improve the overall recognition accuracy and robustness. The process employs feature-level and score-level fusion techniques to effectively integrate the information from different biometric sources. Feature-level fusion concatenates the feature vectors extracted from each modality, while score-level fusion combines the individual recognition scores using weighted averaging or other combination rules. The fusion and decision process also employs machine learning algorithms, such as support vector machines (SVMs) or decision trees, to make the final recognition decision based on the fused biometric data.

Additional Considerations

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for remote and/or automated medical diagnosis through the disclosed principles herein. Thus, while particular embodiments and applications have been illustrated and described, it is to be understood that the disclosed embodiments are not limited to the precise construction and components disclosed herein. Various apparent modifications, changes and variations may be made in the arrangement, operation and details of the method and apparatus disclosed herein without departing from the spirit and scope defined in the appended claims.

What is claimed is:

1. A computing system for assisting a provider with differential diagnosis and standard of care, the computing system comprising:
   at least one computing processor; and
   memory comprising instructions that, when executed by the at least one computing processor, enable the computing system to:
   receive patient information including at least two of patient-reported symptoms, provider notes, patient records, or sensor data from a medical device;
   preprocess the patient information by extracting a set of features and storing the features in a standardized format;
   process the preprocessed patient information using at least one deep learning model to generate a ranked list of potential diagnoses and a likelihood score for each potential diagnosis;
   provide the ranked list of potential diagnoses, and the likelihood scores, to the provider via an interactive user interface;
   receive feedback from the provider indicating an appropriateness of the potential diagnoses and any additional insights;
   fine-tune the at least one deep learning model based on at least one of the received patient-reported symptoms, patient records, sensor data, provider notes, and received provider feedback using a reinforcement learning approach, wherein the reinforcement learning approach comprises: defining a reward function based on at least one of the appropriateness of the potential diagnoses and the efficiency of the diagnostic process, exploring alternative diagnostic strategies by perturbing the inputs to the at least one deep learning model, and updating the model parameters to maximize the expected cumulative reward over time; and update at least one of model parameters or training data for the at least one deep learning model based on at least one of the received patient-reported symptoms, patient records, sensor data, provider notes, and received provider feedback.

2. The system of claim 1, wherein the at least one deep learning model comprises at least one of a convolutional neural network, a recurrent neural network, or a transformer model.

3. The system of claim 1, wherein the instructions further cause the system to:
retrieve, for each potential diagnosis, a set of recommended next steps based on a dynamically updated standard of care knowledge base;
prioritize the recommended next steps based on patient-specific factors and the likelihood scores of the potential diagnoses; and
provide the prioritized recommended next steps to the provider via the interactive user interface.

4. The system of claim 1, wherein the sensor data includes at least one of electrocardiogram, heart rate, blood glucose, blood oxygen percentage/saturation, body temperature, blood pressure, respiratory rate, respiratory volume, heart/lung/abdominal sounds, body fat, muscle tone, images and/or video of the ear/nose/throat, images and/or video of the outer eye and skin, or body temperature data.

5. The system of claim 1, wherein preprocessing the patient information further includes:
identifying and correcting errors and inconsistencies in the patient information;
normalizing numerical values to a common scale; and
encoding categorical variables as binary vectors.

6. The system of claim 1, wherein the instructions further cause the system to:
securely transmit the patient information and provider feedback to a centralized server for aggregation with data from multiple healthcare providers and/or patients; and
periodically update the at least one deep learning model with the aggregated data.

7. The system of claim 1, wherein providing the ranked list of potential diagnoses comprises providing a visualization of key factors contributing to each diagnosis, wherein the visualization of the key factors contributing to each diagnosis includes an attention map highlighting the most relevant features of the patient information for each diagnosis.

8. The system of claim 1, wherein the interactive user interface allows the provider to adjust the likelihood score threshold for displaying potential diagnoses, and/or at least one of manually add, remove, upvote or downvote diagnoses from the ranked list.

9. The system of claim 1, wherein the instructions further cause the system to:
continuously monitor real-time sensor data for signs of patient deterioration; and
alert a provider if the patient's condition deviates from an expected trajectory based on the current diagnosis and treatment plan.

10. A computer implemented method for assisting a provider with differential diagnosis and standard of care, the computer implemented method comprising:
receiving patient information including at least two of patient-reported symptoms, provider notes, patient records, and sensor data from a medical device;
preprocessing the patient information by extracting a set of features and storing the features in a standardized format;
processing the preprocessed patient information using at least one deep learning model to generate a ranked list of potential diagnoses and a likelihood score for each potential diagnosis;
providing the ranked list of potential diagnoses, the likelihood scores, to the provider via an interactive user interface;
receiving feedback from the provider indicating an appropriateness of the potential diagnoses and any additional insights;
fine-tuning the at least one deep learning model based on at least one of the received patient-reported symptoms, patient records, sensor data, provider notes, and received provider feedback using a reinforcement learning approach, wherein the reinforcement learning approach comprises: defining a reward function based on at least one of the appropriateness of the potential diagnoses and the efficiency of the diagnostic process, exploring alternative diagnostic strategies by perturbing the inputs to the at least one deep learning model, and updating the model parameters to maximize the expected cumulative reward over time; and
updating at least one of model parameters or training data for the at least one deep learning model based on at least one of the received patient-reported symptoms, patient records, sensor data, provider notes, or received provider feedback.

11. The computer implemented method according to claim 10 wherein the at least one deep learning models includes at least one convolutional neural network for processing image data, at least one recurrent neural network for processing time-series data, and at least one transformer model for processing unstructured text data.

12. The computer implemented method of claim 10, wherein the instructions further cause the system to:
retrieve, for each potential diagnosis, a set of recommended next steps based on a dynamically updated standard of care knowledge base;
prioritize the recommended next steps based on patient-specific factors and the likelihood scores of the potential diagnoses; and
provide the prioritized recommended next steps to the provider via the interactive user interface.

13. The computer implemented method of claim 10, wherein the sensor data includes at least one of electrocardiogram, heart rate, blood glucose, blood oxygen percentage/saturation, body temperature, blood pressure, respiratory rate, respiratory volume, heart/lung/abdominal sounds, body fat, muscle tone, images and/or video of the ear/nose/throat, images and/or video of the outer eye and skin, or body temperature data.

14. The computer implemented method of claim 10, wherein preprocessing the patient information further includes:
identifying and correcting errors and inconsistencies in the patient information;
normalizing numerical values to a common scale; and
encoding categorical variables as binary vectors.

15. The computer implemented method of claim 10, further comprising:
 securely transmit the patient information and provider feedback to a centralized server for aggregation with data from multiple healthcare providers and/or patients; and
 periodically update the at least one deep learning model with the aggregated data.

16. The computer implemented method of claim 10, wherein providing the ranked list of potential diagnoses comprises providing a visualization of key factors contributing to each diagnosis, wherein the visualization of the key factors contributing to each diagnosis includes an attention map highlighting the most relevant features of the patient information for each diagnosis.

17. The computer implemented method of claim 10, wherein the interactive user interface allows the provider to adjust the likelihood score threshold for displaying potential diagnoses, and/or at least one of manually add, remove, upvote or downvote diagnoses from the ranked list.

18. The computer implemented method of claim 10, wherein the instructions further cause the system to:
 continuously monitor real-time sensor data for signs of patient deterioration; and
 alert a provider if the patient's condition deviates from an expected trajectory based on the current diagnosis and treatment plan.

19. A non-transitory computer readable medium comprising instructions that when executed by a processor enable the processor to:
 receive patient information including at least two of patient-reported symptoms, provider notes, patient records, and sensor data from a medical device;
 preprocess the patient information by extracting a set of features and storing the features in a standardized format;
 process the preprocessed patient information using at least one deep learning model to generate a ranked list of potential diagnoses and a likelihood score for each potential diagnosis;
 provide the ranked list of potential diagnoses, the likelihood scores, to the provider via an interactive user interface;
 receive feedback from the provider indicating an appropriateness of the potential diagnoses and any additional insights;
 fine-tune the at least one deep learning model based on at least one of the received patient-reported symptoms, patient records, sensor data, provider notes, and received provider feedback using a reinforcement learning approach, wherein the reinforcement learning approach comprises: defining a reward function based on at least one of the appropriateness of the potential diagnoses and the efficiency of the diagnostic process, exploring alternative diagnostic strategies by perturbing the inputs to the at least one deep learning model, and updating the model parameters to maximize the expected cumulative reward over time; and
 update at least one of model parameters or training data for the at least one deep learning model based on at least one of the received patient-reported symptoms, patient records, sensor data, provider notes, or received provider feedback.

\* \* \* \* \*